(12) United States Patent
Okada et al.

(10) Patent No.: US 9,840,359 B2
(45) Date of Patent: Dec. 12, 2017

(54) OXYGEN-ABSORBING RESIN COMPOSITION, AND MULTILAYER BODY, CONTAINER, INJECTION-MOLDED BODY, AND MEDICAL CONTAINER USING SAME

(71) Applicant: MITSUBISHI GAS CHEMICAL COMPANY, INC., Tokyo (JP)

(72) Inventors: Satoshi Okada, Kanagawa (JP); Toshiya Takagi, Tokyo (JP); Takashi Kashiba, Kanagawa (JP); Shinpei Iwamoto, Kanagawa (JP); Shinichi Ikeda, Kanagawa (JP); Fumihiro Ito, Kanagawa (JP); Shun Ogawa, Kanagawa (JP); Shota Arakawa, Kanagawa (JP); Kenichiro Usuda, Kanagawa (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 849 days.

(21) Appl. No.: 14/364,416

(22) PCT Filed: Dec. 17, 2012

(86) PCT No.: PCT/JP2012/082610
§ 371 (c)(1),
(2) Date: Jun. 11, 2014

(87) PCT Pub. No.: WO2013/089268
PCT Pub. Date: Jun. 20, 2013

(65) Prior Publication Data
US 2015/0298887 A1    Oct. 22, 2015

(30) Foreign Application Priority Data

Dec. 16, 2011  (JP) .................................. 2011-275861
Aug. 10, 2012  (JP) .................................. 2012/178270
Dec. 3, 2012   (JP) .................................. 2012-264590
Dec. 4, 2012   (JP) .................................. 2012-265119
Dec. 4, 2012   (JP) .................................. 2012-265120
Dec. 6, 2012   (JP) .................................. 2012-267218
Dec. 7, 2012   (JP) .................................. 2012-268338
Dec. 10, 2012  (JP) .................................. 2012-269379
Dec. 10, 2012  (JP) .................................. 2012-269380
Dec. 11, 2012  (JP) .................................. 2012-270356

(51) Int. Cl.
*B65D 81/26* (2006.01)
*B32B 27/34* (2006.01)
(Continued)

(52) U.S. Cl.
CPC ............. *B65D 81/266* (2013.01); *B32B 1/02* (2013.01); *B32B 27/08* (2013.01); *B32B 27/18* (2013.01); *B32B 27/32* (2013.01); *B32B 27/325* (2013.01); *B32B 27/327* (2013.01); *B32B 27/34* (2013.01); *B32B 27/36* (2013.01); *B65D 65/40* (2013.01); *C08G 69/26* (2013.01); *C08G 69/36* (2013.01); *C08K 7/14* (2013.01); *C08L 77/06* (2013.01); *A61J 1/05* (2013.01); *A61M 5/31* (2013.01);
(Continued)

(58) Field of Classification Search
CPC ...... B65D 81/266; B65D 65/40; B32B 27/34; B32B 27/08; B32B 2307/74; B32B 27/18; B32B 27/32; B32B 27/325; B32B 27/327; B32B 27/36; B32B 2307/7244; B32B 2439/70; B32B 2553/00; B32B 1/02; B32B 2250/03; B32B 2250/24; B32B 2307/7242; B32B 2439/00; B32B 2307/724; C08G 69/26; C08G 69/36; C08K 7/14; C08L 77/06; A61J 1/05; A61M 5/31
See application file for complete search history.

(56) References Cited

U.S. PATENT DOCUMENTS 3,534,002 A    10/1970  Gibbons et al.
4,966,699 A    10/1990  Sasaki et al.
(Continued)

FOREIGN PATENT DOCUMENTS

JP    51-136845    11/1976
JP    1-259870     10/1989
(Continued)

OTHER PUBLICATIONS

International Search Report issued Mar. 19, 2013 in PCT/JP2012/082610 and English language translation thereof.
(Continued)

*Primary Examiner* — Michael C Miggins
(74) *Attorney, Agent, or Firm* — Greenblum & Bernstein, P.L.C.

(57) ABSTRACT

Provided are a novel oxygen-absorbing resin composition not responsive to a metal detector, producing no odor after absorption of oxygen and having excellent oxygen-absorbing performance, and a multilayer body, container, injection-molded article and medical container using these. Further provided are an oxygen-absorbing resin composition etc. having excellent oxygen-absorbing performance in a wide range of humidity conditions from low humidity to high humidity. The oxygen-absorbing resin composition of the present invention is an oxygen-absorbing resin composition containing a polyamide compound and a transition metal catalyst, wherein the polyamide compound has at least one constituent unit having a tetralin ring. Moreover, the multilayer body, container, injection-molded article, medical container, etc. of the present invention are obtained by using the oxygen-absorbing resin composition of the present invention.

14 Claims, No Drawings

(51) Int. Cl.

| | | |
|---|---|---|
| *C08G 69/26* | (2006.01) | |
| *C08G 69/36* | (2006.01) | |
| *C08K 7/14* | (2006.01) | |
| *C08L 77/06* | (2006.01) | |
| *B32B 27/08* | (2006.01) | |
| *B32B 27/18* | (2006.01) | |
| *B32B 27/32* | (2006.01) | |
| *B32B 27/36* | (2006.01) | |
| *B65D 65/40* | (2006.01) | |
| *B32B 1/02* | (2006.01) | |
| *A61J 1/05* | (2006.01) | |
| *A61M 5/31* | (2006.01) | |

(52) U.S. Cl.
  CPC ....... *B32B 2250/03* (2013.01); *B32B 2250/24* (2013.01); *B32B 2307/724* (2013.01); *B32B 2307/7242* (2013.01); *B32B 2307/7244* (2013.01); *B32B 2307/74* (2013.01); *B32B 2439/00* (2013.01); *B32B 2439/70* (2013.01); *B32B 2553/00* (2013.01)

(56) References Cited

U.S. PATENT DOCUMENTS

| 5,346,644 | A | 9/1994 | Speer et al. |
|---|---|---|---|
| 5,700,554 | A | 12/1997 | Speer et al. |
| 6,063,503 | A | 5/2000 | Hatakeyama et al. |
| 6,124,043 | A | 9/2000 | Tsukamoto et al. |
| 2004/0267194 | A1 | 12/2004 | Sano et al. |
| 2005/0228122 | A1 | 10/2005 | Kannan et al. |
| 2012/0128532 | A1 | 5/2012 | Kashiba et al. |

FOREIGN PATENT DOCUMENTS

| JP | 2-500846 | 3/1990 |
|---|---|---|
| JP | 5-115776 | 5/1993 |
| JP | 07-112949 | 5/1995 |
| JP | 8-127641 | 5/1996 |
| JP | 9-234832 | 9/1997 |
| JP | 11-255913 | 9/1999 |
| JP | 2001-105540 | 4/2001 |
| JP | 2001-252560 | 9/2001 |
| JP | 2003-521552 | 7/2003 |
| JP | 2004-229750 | 8/2004 |
| JP | 2009-108153 | 5/2009 |
| JP | 2009-248983 | 10/2009 |
| JP | 2010-105318 | 5/2010 |
| JP | 2011-225638 | 11/2011 |
| JP | 2012-124428 | 6/2012 |
| WO | 89/08557 | 9/1989 |
| WO | 99/48963 | 9/1999 |
| WO | 2010/147097 | 12/2010 |

OTHER PUBLICATIONS

International Preliminary Report on Patentability issued Jun. 17, 2014 in English in PCT/JP2012/082610.

OXYGEN-ABSORBING RESIN COMPOSITION, AND MULTILAYER BODY, CONTAINER, INJECTION-MOLDED BODY, AND MEDICAL CONTAINER USING SAME

TECHNICAL FIELD

The present invention relates to an oxygen-absorbing resin composition, and particularly, to an oxygen-absorbing resin composition at least containing a polyamide compound having a tetralin ring and a transition metal catalyst. The present invention also relates to e.g., a multilayer body and a container excellent in oxygen barrier performance and oxygen-absorbing performance in a wide range of humidity conditions from low humidity to high humidity. The present invention further relates to a multilayer injection-molded article having oxygen-absorbing function, a medical multilayer container having oxygen barrier performance, oxygen-absorbing function and water vapor barrier performance, a container obtained by processing the multilayer injection-molded article, and a method for storing a biopharmaceutical in the above medical multilayer container.

BACKGROUND ART

In order to prevent oxygen oxidation and store various types of articles, represented by foods, beverages, medicinal products, cosmetics, etc., which easily deteriorate or degrade under the effect of oxygen for a long time, oxygen absorbents are used for removing oxygen within packaging bodies storing these articles.

As the oxygen absorbent, an oxygen absorbent containing an iron powder as a reactive main component is generally used in view of oxygen-absorbing ability, handling and safety. However, the iron-based oxygen absorbent is responsive to a metal detector and thus it is difficult to use a metal detector in inspecting foreign matter. Furthermore, packaging bodies containing an iron-based oxygen absorbent have a risk of ignition, and thus, they cannot be heated by a microwave oven. Moreover, the oxidation reaction of an iron powder requires water, and thus, an oxygen-absorbing effect is exerted only on an article to be packed rich in moisture content.

Packaging containers are developed by making the container of a multilayer material having an oxygen-absorbing layer formed of an oxygen-absorbing resin composition containing a thermoplastic resin and an iron-based oxygen absorbent, thereby improving a gas barrier property of the container and providing an oxygen-absorbing function to the container itself (see, Patent Document 1). Specifically, the multilayer material is an oxygen-absorbing multilayer film having an oxygen-absorbing layer, which is formed by providing an oxygen-absorbing layer formed of a thermoplastic resin having an iron-based oxygen absorbent dispersed therein, between layers of a gas barrier multilayer film, which is formed by laminating a heat sealing layer and a gas barrier layer in a conventional manner, thereby imparting not only a function of preventing oxygen transmission from outside but also a function of absorbing oxygen within a container, and which is manufactured by use of a conventional manufacturing method known in the art, such as extrusion lamination, coextrusion lamination and dry lamination. However, such an oxygen-absorbing multilayer film has the same problems: the container is detected by a metal detector for inspecting foreign matter for foods etc.; and the effect is only exerted on an article to be packed rich in moisture content. In addition, the multilayer film has a problem of opacity, leading to insufficient visibility of content.

In the aforementioned circumstances, it has been desired to develop an oxygen absorbent containing an organic substance as a reactive main component. As the oxygen absorbent containing an organic substance as a reactive main component, an oxygen absorbent containing ascorbic acid as a main component is known (see, Patent Document 2).

In the meantime, an oxygen-absorbing resin composition composed of a resin and a transition metal catalyst is known. For example, a resin composition composed of a polyamide as an oxidizable organic component (in particular, a xylylene group-containing polyamide) and a transition metal catalyst, is known (see, Patent Documents 3 and 4). In Patent Documents 3 and 4, articles obtained by molding such a resin composition, such as an oxygen absorbent, a packaging material and a multilayer laminated film for packaging are further exemplified.

As an oxygen-absorbing resin composition requiring no moisture content for absorbing oxygen, an oxygen-absorbing resin composition composed of a resin having a carbon-carbon unsaturated bond and a transition metal catalyst, is known (see, Patent Document 5).

As a composition for trapping oxygen, a composition composed of a polymer containing a substituted cyclohexene functional group or a low molecular-weight substance bound with the cyclohexene ring and a transition metal is known (see, Patent Document 6).

In the meantime, injection molding, by which molded articles having a complicate-shape can be manufactured in a high yield, has been used for manufacturing a wide variety of products including machine parts, automotive parts, electric/electronic parts, containers for foods or medical products, etc. Recently, as packaging containers, variety types of plastic containers have been widely used because they have advantages of light-weight, transparency, moldability, etc. As a typical plastic container for a beverage, an injection-molded article having a screw thread cutting on the bottle neck designed to sufficiently screw the lid, has been frequently used.

As a material for use in injection-molded articles, general thermoplastic resins such as a polyolefin (polyethylene, polypropylene, etc.), a polyester and a polystyrene are mentioned. Particularly, injection-molded articles mainly formed of a polyester such as polyethylene terephthalate (PET) are used in a wide variety of plastic containers for beverages such as tea, fruit juice beverages, carbonated beverages and alcohol beverages. However, although an injection-molded article mainly formed of a thermoplastic resin is excellent as a packaging article, oxygen tends to easily transmit from the outside, unlike glass bottles and metal containers. Thus, even if a content is packed and hermetically closed therein, the storage stability of the content is still questioned. Accordingly, multilayer injection-molded articles having a gas barrier layer as an intermediate layer in order to provide a gas barrier property to such injection-molded articles composed of a general resin have been put into practical use.

In the meantime, as medical packaging containers for packaging and storing a drug solution in a sealed condition, glass ampoules, vials, prefilled syringes, etc. have been conventionally used. However, these glass containers have problems: sodium ion etc. elute off from the container to a liquid content stored therein; and micro substances called flakes generate; when a light-blocking glass container colored with a metal is used, the content is contaminated with the coloring metal; and the container is easily broken by drop impact. In addition to these problems, since glass containers have a relatively large specific gravity, medical packaging containers become heavy. For these reasons, development of alternate materials has been desired. To be more specific, materials lighter than glass, such as a polyester, a polycarbonate, a polypropylene and a cycloolefin polymer, have been investigated as glass alternatives.

For example, a medical container formed of a polyester resin material is proposed (see, Patent Document 7).

In the meantime, a multilayer container having a gas barrier layer as an intermediate layer in order to provide a gas barrier property to a container made of plastic, has been investigated. Specifically, a prefilled syringe improved in oxygen barrier property by constituting the innermost layer and the outermost layer formed of a polyolefin resin and an intermediate layer formed of a resin composition excellent in oxygen barrier property is proposed (see, Patent Document 8). Other than this, multilayer containers obtained by laminating a gas barrier layer formed of e.g., a polyamide (hereinafter, sometimes referred to as "nylon MXD6"), which is obtained from metaxylylenediamine and adipic acid, an ethylene-vinyl alcohol copolymer, a polyacrylonitrile, a poly(vinylidene chloride), an aluminum foil, a carbon coat or a vapor-deposited inorganic oxide, on a resin layer, have been investigated.

In recent years, it has been proposed that a small amount of transition metal compound is added to nylon MXD6 and mixed to provide an oxygen-absorbing function and the resultant material is used as an oxygen barrier material constituting containers and packaging materials (see, Patent Document 9).

Examples of the medical containers include ampoules, vials and syringes. Other than these, examples of the medical containers include an artificial kidney hemodialyzer (dialyzer). As the housing of such a dialyzer, a transparent (easy-to-see) plastic such as a polystyrene and a polycarbonate is used. To avoid breakage caused by dropping and other impact, a polycarbonate having satisfactory impact resistance is more preferably used (see Patent Document 10).

CITATION LIST

Patent Document

Patent Document 1: Japanese Patent Application Laid-Open No. 9-234832
Patent Document 2: Japanese Patent Application Laid-Open No. 51-136845
Patent Document 3: Japanese Patent Application Laid-Open No. 2001-252560
Patent Document 4: Japanese Patent Application Laid-Open No. 2009-108153
Patent Document 5: Japanese Patent Application Laid-Open No. 5-115776
Patent Document 6: National Publication of International Patent Application No. 2003-521552
Patent Document 7: Japanese Patent Application Laid-Open No. 8-127641
Patent Document 8: Japanese Patent Application Laid-Open No. 2004-229750
Patent Document 9: Japanese Patent Application Laid-Open No. 2-500846
Patent Document 10: Japanese Patent Application Laid-Open No. 1-259870

SUMMARY OF INVENTION

Technical Problem

However, the oxygen absorbent of Patent Document 2 has problems in that the oxygen-absorbing performance is primarily low; an effect is exerted only on an article to be packed rich in moisture content; and the cost is relatively high.

The resin composition of Patent Document 3 has the following problem. Since an oxygen-absorbing function is exerted by oxidizing a xylylene group-containing polyamide resin in the presence of a transition metal catalyst being included in the composition, the polymer chain of the resin is cut by oxidation degradation after absorption of oxygen, with the result that the strength of the packaging container itself decreases. In addition, the oxygen-absorbing performance of the resin composition described therein is still insufficient and the oxygen-absorbing effect is exerted only on an article to be packed rich in moisture content. In Patent Document 4, a method of improving interlayer peeling is described; however, the effect is limited. In addition to this problem, the oxygen-absorbing performance of the resin composition described therein is still insufficient and the effect is exerted only on an article to be packed rich in moisture content.

The oxygen-absorbing resin composition of Patent Document 5 has the same problem as mentioned above, that is, the polymer chain of the resin is cut by oxidation to produce low molecular-weight organic compounds serving as odor-producing components, with the result that odor is produced after absorption of oxygen.

In the composition of Patent Document 6, a special material containing a cyclohexene functional group must be used. This material still has a problem in relatively easily producing odor.

In the meantime, in the conventional gas barrier multilayer container and medical multilayer container mentioned above, the basic performance including oxygen barrier property, water vapor barrier property, drug solution adsorptivity, durability, etc. is not sufficient. Because of this, in view of storage stability of a content such as a drug solution and a food, improvement is required.

In particular, when foods, drug solutions, etc. are stored in conventional gas barrier multilayer containers, as a matter of fact, it is difficult or economically extremely unfavorable to completely remove oxygen in a packaging container no matter how gas displacement operation is performed. In other words, it is difficult to completely eliminate oxygen such as oxygen dissolved in a liquid content, oxygen contained in air bubbles generated and introduced in mixing contents, and oxygen dissolved in water when water is added. It is possible to remove oxygen as much as possible by highly strictly controlling conditions for selecting and preparing raw materials and manufacturing conditions; however, such an operation ignores an economic aspect and thus unrealistic. In addition, since the oxygen barrier property of the gas barrier multilayer containers as mentioned above is not sufficient, a small amount of oxygen entering through the wall of containers from the outside cannot be completely eliminated.

A medical container formed of a polyester resin, for example, disclosed in Patent Document 7, has relatively excellent oxygen barrier property; however, the oxygen barrier property is insufficient to completely block oxygen. Such a medical container is inferior also in water vapor barrier property, compared to a container formed of a polyolefin resin. In addition, the polyester resin has no oxygen-absorbing performance. Because of this, when oxygen enters a container from the outside or when oxygen remains in the head space above the content (drug solution) in a container, degradation of the drug solution within the container cannot be prevented. The medical container has such a problem.

Furthermore, the prefilled syringe of Patent Document 8 has relatively excellent oxygen barrier property and water vapor barrier property; however, the oxygen barrier property is insufficient to completely block oxygen. In addition, the oxygen barrier resin composition used in an intermediate layer does not have oxygen-absorbing performance. Therefore, when oxygen enters the container from the outside or when oxygen remains in the head space above the content in the container, degradation of the drug solution within the container cannot be prevented. The prefilled syringe has such a problem.

The resin composition of Patent Document 9 has the same problem as in Patent Documents 3 and 4. The strength of a resin decreases due to oxidation degradation after oxidation absorption and the strength of a packaging container itself decreases. In addition, the resin composition has problems in that oxygen-absorbing performance is still insufficient and an effect is exerted only on an article to be packed rich in moisture content.

The housing of the dialyzer described in Patent Document 10 has excellent transparency and impact resistance. However, a polycarbonate is insufficient in oxygen barrier property and water vapor barrier property for use in a container housing and storing a drug solution, and has a problem in view of long-term storage property of a content.

The present invention was made in consideration of the problems mentioned above. An object of the invention is to provide a novel oxygen-absorbing resin composition not responding to a metal detector, producing no odor after absorption of oxygen and having excellent oxygen-absorbing performance. Another object of the present invention is to provide an oxygen-absorbing resin composition having excellent oxygen-absorbing performance in a wide range of humidity conditions from low humidity to high humidity.

Another object of the present invention is to provide a novel oxygen-absorbing multilayer body not responding to a metal detector, producing no odor after absorption of oxygen and having excellent oxygen-absorbing performance, and provide an oxygen-absorbing multilayer container using the multilayer body. Yet another object of the present invention is to provide an oxygen-absorbing multilayer body having excellent oxygen-absorbing performance in a wide range of humidity conditions from low humidity to high humidity and provide an oxygen-absorbing multilayer container using the multilayer body.

Another object of the present invention is to provide a novel oxygen-absorbing multilayer injection-molded article not responding to a metal detector, producing no odor after absorption of oxygen, and having excellent oxygen-absorbing performance, and provide an oxygen-absorbing container using the multilayer injection-molded article. Another object of the present invention is to provide an oxygen-absorbing multilayer injection-molded article having excellent oxygen-absorbing performance in a wide range of humidity conditions from low humidity to high humidity, and provide an oxygen-absorbing container using the multilayer injection-molded article.

Another object of the present invention is to provide a novel oxygen-absorbing medical multilayer molded container and an oxygen-absorbing prefilled syringe significantly suppressed in production of low molecular weight compounds after absorption of oxygen and having excellent oxygen barrier performance, preferably, also having excellent water vapor barrier performance, maintaining strength even in long-term storage and eluting a small amount of impurities. Another object of the present invention is to provide an oxygen-absorbing medical multilayer molded container and an oxygen-absorbing prefilled syringe having excellent oxygen-absorbing performance in a wide range of humidity conditions from low humidity to high humidity.

Another object of the present invention is to provide a method for storing a biopharmaceutical for a long term while suppressing deterioration and efficacy reduction of the biopharmaceutical, without contamination of impurities.

Solution to Problem

The present inventors conducted intensive studies on an oxygen-absorbing resin composition. As a result, they found that the aforementioned problems are solved by using a polyamide compound having a predetermined tetralin ring and a transition metal catalyst, and accomplished the present invention.

More specifically, the present invention provides the following <1-1> to <1-14>.

<1-1> An oxygen-absorbing resin composition containing a polyamide compound and a transition metal catalyst, wherein the polyamide compound has at least one constituent unit having a tetralin ring selected from the group consisting of constituent units represented by the following general formulas (1) to (2):

[Formula 1]

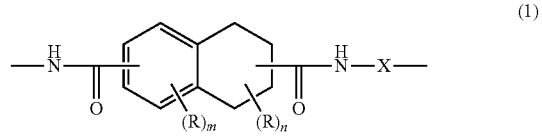

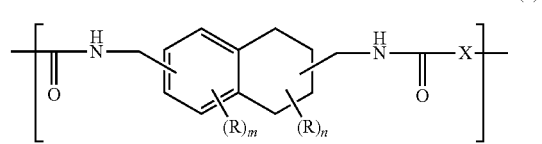

where R each independently represents a monovalent substituent, the monovalent substituent being at least one selected from the group consisting of a halogen atom, an alkyl group, an alkenyl group, an alkynyl group, an aryl group, a heterocyclic group, a cyano group, a hydroxy group, a carboxyl group, an ester group, an amido group, a nitro group, an alkoxy group, an aryloxy group, an acyl group, an amino group, a mercapto group, an alkylthio group, an arylthio group, a heterocyclic thio group and an imido group, these of which may further have a substituent; where m each independently represents an integer of 0 to 3; where n each independently represents an integer of 0 to 6, and at least one hydrogen atom is bound to a benzyl position of the tetralin ring; where X each independently represents a divalent group containing at least one group selected from the group consisting of an aromatic hydrocarbon group, a saturated or unsaturated alicyclic hydrocarbon group and a linear or branched, saturated or unsaturated aliphatic hydrocarbon group, and a heterocyclic group.

<1-2> The oxygen-absorbing resin composition according to the above <1-1>, wherein the transition metal catalyst contains at least one transition metal selected from the group consisting of manganese, iron, cobalt, nickel and copper.

<1-3> The oxygen-absorbing resin composition according to the above <1-1> or <1-2>, wherein the transition metal catalyst is contained in an amount of 0.001 to 10 parts by mass in terms of a transition metal based on 100 parts by mass of the polyamide compound.

<1-4> The oxygen-absorbing resin composition according to any one of the above <1-1> to <1-3>, wherein the constituent unit represented by the general formula (1) is at least one selected from the group consisting of the constituent units represented by following formulas (3) to (6):

[Formula 2]

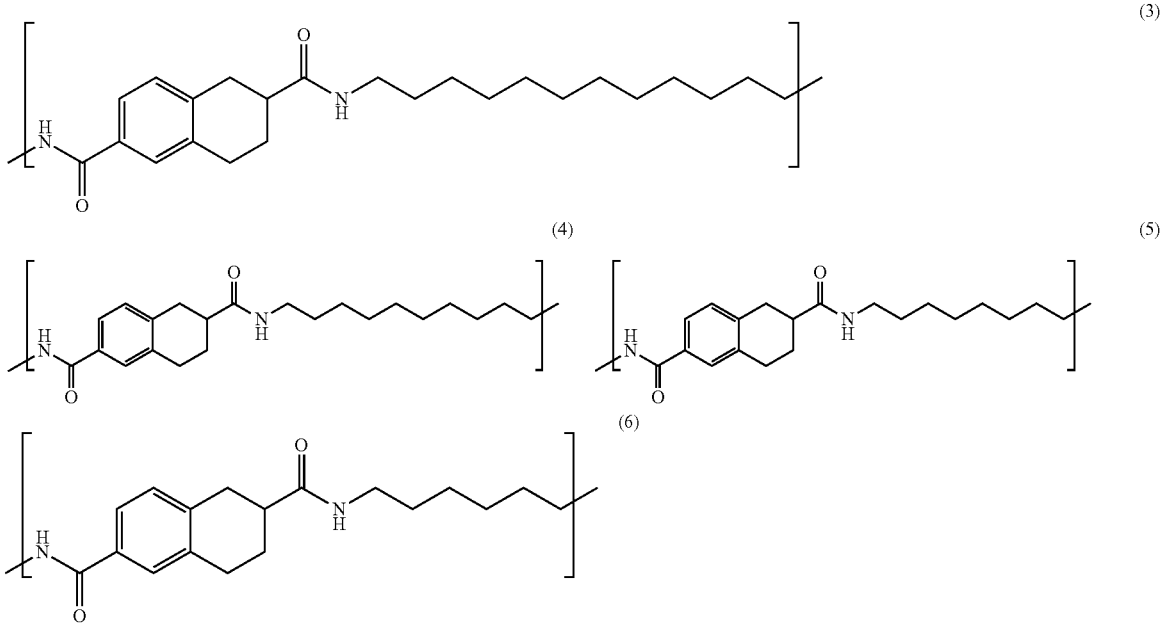

<1-5> An oxygen-absorbing multilayer body having at least three layers including a sealant layer containing a thermoplastic resin, an oxygen-absorbing layer formed of the oxygen-absorbing resin composition according to any one of the above <1-1> to <1-4> and a gas barrier layer containing a gas barrier substance, these of which are laminated in this order.

<1-6> An oxygen-absorbing multilayer container comprising the oxygen-absorbing multilayer body according to the above <1-5>.

<1-7> An oxygen-absorbing multilayer injection-molded article comprising an oxygen-absorbing layer formed of the oxygen-absorbing resin composition according to any one of the above <1-1> to <1-4> and a resin layer containing a thermoplastic resin.

<1-8> An oxygen-absorbing multilayer container obtained by molding the oxygen-absorbing multilayer injection-molded article according to the above <1-7> into a cup or bottle form.

<1-9> The oxygen-absorbing multilayer container according to the above <1-8>, wherein the molding is stretch blow molding.

<1-10> An oxygen-absorbing medical multilayer molded container having at least three layers including a first resin layer at least containing a thermoplastic resin, an oxygen-absorbing layer formed of the oxygen-absorbing resin composition according to any one of the above <1-1> to <1-4> and a second resin layer at least containing a thermoplastic resin in this order.

<1-11> The oxygen-absorbing medical multilayer molded container according to <1-10>, wherein the thermoplastic resin of each of the first resin layer and the thermoplastic resin of the second resin layer is a polyolefin.

<1-12> The oxygen-absorbing medical multilayer molded container according to the above <1-10>, wherein each of the thermoplastic resin of the first resin layer and the thermoplastic resin of the second resin layer is a polyester.

<1-13> An oxygen-absorbing prefilled syringe made capable of storing a medicinal agent in advance in a sealed condition, and releasing the sealed condition to eject the medical agent at the time of use, wherein the prefilled syringe is formed of a multilayer structure having at least three layers including a first resin layer containing a thermoplastic resin, an oxygen-absorbing layer formed of the oxygen-absorbing resin composition according to any one of the above <1-1> to <1-4> and a second resin layer containing a thermoplastic resin in this order.

<1-14> A method for storing a biopharmaceutical, comprising storing the biopharmaceutical in the oxygen-absorbing medical multilayer molded container according to any one of <1-10> to <1-12> or in the oxygen-absorbing prefilled syringe according to <1-13>.

The present inventors further conducted intensive studies on an oxygen-absorbing multilayer body. As a result, they found that the aforementioned problems are solved by using a polyamide compound having a predetermined tetralin ring and a transition metal catalyst, and accomplished the present invention.

More specifically, the present invention provides the following <2-1> to <2-5>.

<2-1> An oxygen-absorbing multilayer body having at least three layers including a sealant layer containing a thermoplastic resin, an oxygen-absorbing layer formed of an oxygen-absorbing resin composition containing a polyamide compound and a transition metal catalyst, and a gas barrier layer containing a gas barrier substance, these of which are laminated in this order, wherein
the polyamide compound has at least one constituent unit having a tetralin ring selected from the group consisting of constituent units represented by the above general formulas (1) and (2).

<2-2> The oxygen-absorbing multilayer body according to the above <2-1>, wherein the transition metal catalyst contains at least one transition metal selected from the group consisting of manganese, iron, cobalt, nickel and copper.

<2-3> The oxygen-absorbing multilayer body according to the above <2-1> or <2-2>, wherein the transition metal catalyst is contained in an amount of 0.001 to 10 parts by mass in terms of a transition metal based on 100 parts by mass of the polyamide compound.

<2-4> The oxygen-absorbing multilayer body according to any one of the above <2-1> to <2-3>, wherein the constituent unit represented by the general formula (1) is at least one selected from the group consisting of the constituent units represented by the above formulas (3) to (6).

<2-5> An oxygen-absorbing multilayer container having the oxygen-absorbing multilayer body according to any one of the above <2-1> to <2-4>.

Further, the present inventors conducted intensive studies on an oxygen-absorbing multilayer injection-molded article. As a result, they found that the aforementioned problems are solved by using a polyamide compound having a predetermined tetralin ring and a transition metal catalyst, and accomplished the present invention.

More specifically, the present invention provides the following <3-1> to <3-6>.

<3-1> An oxygen-absorbing multilayer injection-molded article having an oxygen-absorbing layer formed of an oxygen-absorbing resin composition containing a polyamide compound and a transition metal catalyst, and a resin layer containing a thermoplastic resin, wherein
the polyamide compound has at least one constituent unit having a tetralin ring selected from the group consisting of constituent units represented by the above general formulas (1) and (2).

<3-2> The oxygen-absorbing multilayer injection-molded article according to the above <3-1>, wherein the transition metal catalyst contains at least one transition metal selected from the group consisting of manganese, iron, cobalt, nickel and copper.

<3-3> The oxygen-absorbing multilayer injection-molded article according to the above <3-1> or <3-2>, wherein the transition metal catalyst is contained in an amount of 0.001 to 10 parts by mass in terms of a transition metal based on 100 parts by mass of the polyamide compound.

<3-4> The oxygen-absorbing multilayer injection-molded article according to any one of the above <3-1> to <3-3>, wherein the constituent unit represented by the general formula (1) is at least one selected from the group consisting of the constituent units represented by the above formulas (3) to (6).

<3-5> An oxygen-absorbing multilayer container obtained by molding the oxygen-absorbing multilayer injection-molded article according to any one of the above <3-1> to <3-4> into a cup or a bottle form.

<3-6> The oxygen-absorbing multilayer container according to the above <3-5>, wherein the molding is stretch blow molding.

Further, the present inventors conducted intensive studies on an oxygen-absorbing medical multilayer molded container. As a result, they found that the aforementioned problems are solved by using a polyamide compound having a predetermined tetralin ring and a transition metal catalyst, and accomplished the present invention.

More specifically, the present invention provides the following <4-1> to <4-4>.

<4-1> An oxygen-absorbing medical multilayer molded container having at least three layers including a first resin layer at least containing a thermoplastic resin, an oxygen-absorbing layer formed of an oxygen-absorbing resin composition containing a polyamide compound and a transition metal catalyst, and a second resin layer at least containing a thermoplastic resin, these of which are laminated in this order, wherein the polyamide compound contains at least one constituent unit having a tetralin ring selected from the group consisting of constituent units represented by the above general formulas (1) and (2).

<4-2> The oxygen-absorbing medical multilayer molded container according to the above <4-1>, wherein the transition metal catalyst contains at least one transition metal selected from the group consisting of manganese, iron, cobalt, nickel and copper.

<4-3> The oxygen-absorbing medical multilayer molded container according to the above <4-1> or <4-2>, wherein the transition metal catalyst is contained in an amount of 0.001 to 10 parts by mass in terms of a transition metal based on 100 parts by mass of the polyamide compound.

<4-4> The oxygen-absorbing medical multilayer molded container according to any one of the above <4-1> to <4-3>, wherein the constituent unit represented by the general formula (1) is at least one selected from the group consisting of the constituent units represented by the above formulas (3) to (6).

Further, the present inventors conducted intensive studies on an oxygen-absorbing medical multilayer molded container. As a result, they found that the aforementioned problems are solved by using a polyamide compound having a predetermined tetralin ring and a transition metal catalyst, and accomplished the present invention.

More specifically, the present invention provides the following <5-1> to <5-4>.

<5-1> An oxygen-absorbing medical multilayer molded container having at least three layers including a first resin layer at least containing a polyolefin, an oxygen-absorbing layer formed of an oxygen-absorbing resin composition containing a polyamide compound and a transition metal catalyst, and a second resin layer at least containing a polyolefin, these of which are laminated in this order, wherein the polyamide compound contains at least one constituent unit having a tetralin ring selected from the group consisting of constituent units represented by the above general formulas (1) and (2).

<5-2> The oxygen-absorbing medical multilayer molded container according to the above <5-1>, wherein the transition metal catalyst contains at least one transition metal selected from the group consisting of manganese, iron, cobalt, nickel and copper.

<5-3> The oxygen-absorbing medical multilayer molded container according to the above <5-1> or <5-2>, wherein the transition metal catalyst is contained in an amount of 0.001 to 10 parts by mass in terms of a transition metal based on 100 parts by mass of the polyamide compound.

<5-4> The oxygen-absorbing medical multilayer molded container according to any one of the above <5-1> to <5-3>, wherein the constituent unit represented by the general formula (1) is at least one selected from the group consisting of the constituent units represented by the above formulas (3) to (6).

Further, the present inventors further conducted intensive studies on an oxygen-absorbing medical multilayer molded container. As a result, they found that the aforementioned problems are solved by using a polyamide compound having a predetermined tetralin ring and a transition metal catalyst, and accomplished the present invention.

More specifically, the present invention provides the following <6-1> to <6-9>.

<6-1> An oxygen-absorbing medical multilayer molded container having at least three layers including a first resin layer at least containing a polyester, an oxygen-absorbing layer formed of an oxygen-absorbing resin composition containing a polyamide compound and a transition metal catalyst, and a second resin layer at least containing a polyester, these of which are laminated in this order, wherein the polyamide compound contains at least one constituent unit having a tetralin ring selected from the group consisting of constituent units represented by the above general formulas (1) and (2).

<6-2> The oxygen-absorbing medical multilayer molded container according to the above <6-1>, wherein the transition metal catalyst contains at least one transition metal selected from the group consisting of manganese, iron, cobalt, nickel and copper.

<6-3> The oxygen-absorbing medical multilayer molded container according to the above <6-1> or <6-2>, wherein the transition metal catalyst is contained in an amount of 0.001 to 10 parts by mass in terms of a transition metal based on 100 parts by mass of the polyamide compound.

<6-4> The oxygen-absorbing medical multilayer molded container according to any one of the above <6-1> to <6-3>, wherein the constituent unit represented by the general formula (1) is at least one selected from the group consisting of the constituent units represented by the above formulas (3) to (6).

<6-5> The oxygen-absorbing medical multilayer molded container according to any one of the above <6-1> to <6-4>, wherein the polyester contains a dicarboxylic acid unit, 70 mole % or more of which is derived from at least one dicarboxylic acid selected from the group consisting of terephthalic acid, isophthalic acid, 1,3-naphthalenedicarboxylic acid, 1,4-naphthalenedicarboxylic acid, 1,5-naphthalenedicarboxylic acid, 2,6-naphthalenedicarboxylic acid, and 2,7-naphthalenedicarboxylic acid.

<6-6> The oxygen-absorbing medical multilayer molded container according to any one of the above <6-1> to <6-4>, wherein the polyester contains a dicarboxylic acid unit, 70 mole % or more of which is derived from terephthalic acid.

<6-7> The oxygen-absorbing medical multilayer molded container according to any one of the above <6-1> to <6-4>, wherein the polyester contains a dicarboxylic acid unit, 90 mole % or more of which is derived from terephthalic acid.

<6-8> The oxygen-absorbing medical multilayer molded container according to any one of the above <6-1> to <6-4>, wherein the polyester contains a dicarboxylic acid unit, 70 mole % or more of which is derived from 2,6-naphthalenedicarboxylic acid.

<6-9> The oxygen-absorbing medical multilayer molded container according to any one of the above <6-1> to <6-4>, wherein the polyester contains a dicarboxylic acid unit, 90 mole % or more of which has a 2,6-naphthalenedicarboxylic acid skeleton.

Further, the present inventors conducted intensive studies on an oxygen-absorbing prefilled syringe. As a result, they found that the aforementioned problems are solved by using a polyamide compound having a predetermined tetralin ring and a transition metal catalyst, and accomplished the present invention.

More specifically, the present invention provides the following <7-1> to <7-4>.

<7-1> An oxygen-absorbing prefilled syringe made capable of storing a medicinal agent in advance in a sealed condition, and releasing the sealed condition to eject the medicinal agent at the time of use, wherein the prefilled syringe is formed of a multilayer structure having at least three layers, including a first resin layer at least containing a thermoplastic resin, an oxygen-absorbing layer formed of the oxygen-absorbing resin composition containing a polyamide compound and a transition metal catalyst and a second resin layer at least containing a thermoplastic resin, these of which are laminated in this order, and the polyamide compound contains at least one constituent unit having a tetralin ring selected from the group consisting of constituent units represented by the above general formulas (1) and (2).

<7-2> The oxygen-absorbing prefilled syringe according to the above <7-1>, wherein the transition metal catalyst contains at least one transition metal selected from the group consisting of manganese, iron, cobalt, nickel and copper.

<7-3> The oxygen-absorbing prefilled syringe according to the above <7-1> or <7-2>, wherein the transition metal catalyst is contained in an amount of 0.001 to 10 parts by mass in terms of a transition metal based on 100 parts by mass of the polyamide compound.

<7-4> The oxygen-absorbing prefilled syringe according to any one of the above <7-1> to <7-3>, wherein the constituent unit represented by the general formula (1) is at least one selected from the group consisting of the constituent units represented by the above formulas (3) to (6).

The present inventors conducted intensive studies on a method for storing a biopharmaceutical. As a result, they found that the aforementioned problems are solved by storing the biopharmaceutical in an oxygen-absorbing medical multilayer molded container using a polyamide compound having a predetermined tetralin ring and a transition metal catalyst, and accomplished the present invention.

More specifically, the present invention provides the following <8-1> to <8-4>.

<8-1> A method for storing a biopharmaceutical in an oxygen-absorbing medical multilayer molded container having at least three layers including a first resin layer at least containing a thermoplastic resin, an oxygen-absorbing layer formed of an oxygen-absorbing resin composition containing a polyamide compound and a transition metal catalyst, and a second resin layer at least containing a thermoplastic resin, these of which are laminated in this order, wherein the polyamide compound contains at least one constituent unit having a tetralin ring selected from the group consisting of constituent units represented by the above general formulas (1) and (2).

<8-2> The method for storing a biopharmaceutical according to the above <8-1>, wherein the transition metal catalyst contains at least one transition metal selected from the group consisting of manganese, iron, cobalt, nickel and copper.

<8-3> The method for storing a biopharmaceutical according to the above <8-1> or <8-2>, wherein the transition metal catalyst is contained in an amount of 0.001 to 10 parts by mass in terms of a transition metal based on 100 parts by mass of the polyamide compound.

<8-4> The method for storing a biopharmaceutical according to any one of the above <8-1> to <8-3>, wherein the constituent unit represented by the general formula (1) is at least one selected from the group consisting of the constituent units represented by the above formulas (3) to (6).

Advantageous Effects of Invention

According to one aspect of the present invention, it is possible to provide an oxygen-absorbing resin composition having excellent oxygen-absorbing performance in a wide range of humidity conditions from low humidity to high humidity, an oxygen-absorbing multilayer body using the composition, and an oxygen-absorbing multilayer container, etc. The oxygen-absorbing resin composition etc., since they can absorb oxygen regardless of the presence or absence of the moisture content of an article to be packed and produce no odor after absorption of oxygen, can be applied to a wide variety of uses including foods, cooking foods, beverages, medicinal products and health foods, no matter what products they are. Furthermore, it is also possible to provide an oxygen-absorbing resin composition etc. not responsive to a metal detector. In addition, according to a preferable aspect of the present invention, since a reduction in strength of the polyamide compound having a tetralin ring by oxidation is extremely low even after absorption of oxygen and the strength of the oxygen-absorbing layer can be maintained even in long-term use, it is also possible to provide an oxygen-absorbing multilayer body rarely having interlayer peeling, an oxygen-absorbing multilayer container, etc. using the multilayer body.

According to another aspect of the present invention, it is possible to provide an oxygen-absorbing multilayer injection-molded article having excellent oxygen-absorbing performance in a wide range of humidity conditions from low humidity to high humidity as well as oxygen-absorbing multilayer containers using these. These oxygen-absorbing multilayer injection-molded articles, oxygen-absorbing multilayer containers, etc., since they can absorb oxygen regardless of the presence or absence of a moisture content of an article to be packed and produce no odor after absorption of oxygen, can be applied to a wide variety of uses including foods, cooking foods, beverages, medicinal products, health foods, etc., no matter what products they are. Furthermore, it is also possible to provide an oxygen-absorbing multilayer injection-molded article, an oxygen-absorbing multilayer container, etc. not responsive to a metal detector. In addition, according to a preferable aspect of the present invention, since a reduction in strength of the polyamide compound by oxidation is extremely low even after absorption of oxygen and the strength of the oxygen-absorbing layer can be maintained even in long-term use, it is also possible to provide an oxygen-absorbing multilayer injection-molded article, an oxygen-absorbing multilayer container, etc. rarely having interlayer peeling.

According to another aspect of the present invention, it is possible to provide an oxygen-absorbing medical multilayer molded container, such as a vial and a prefilled syringe, having excellent oxygen-absorbing performance in a wide range of humidity conditions from low humidity to high humidity and satisfactory oxygen barrier property and, in a preferable aspect, further excellent water vapor barrier property. Such an oxygen-absorbing medical multilayer molded container, since it can absorb oxygen regardless of the presence or absence of the moisture content of an article to be packed, a reduction in strength of the polyamide compound having a tetralin ring by oxidation is extremely low even after absorption of oxygen, and the strength of the oxygen-absorbing layer is maintained even in long-term use, can also provide an oxygen-absorbing medical multilayer molded container rarely having interlayer peeling. Moreover, since generation of a low molecular weight organic compound is suppressed after absorption of oxygen, it is also possible to provide an oxygen-absorbing medical multilayer molded container less contaminating the content with low molecular weight organic compound. Because of this, the oxygen-absorbing medical multilayer molded container of the present invention is particularly useful in storing medicinal products, biopharmaceuticals, medical supplies, and the like requiring storage under a low oxygen concentration.

According to another aspect of the present invention, it is possible to suppress deterioration and an efficacy reduction of a biopharmaceutical since the biopharmaceutical can be stored under a low oxygen concentration. Furthermore, it is possible for the medical multilayer container to be used in the present invention to store a biopharmaceutical for a long term since degradation of a polyamide compound by oxidation is extremely low even after oxygen absorption and the strength of the container is maintained during a long-term use.

DESCRIPTION OF EMBODIMENTS

Now, embodiments of the present invention will be described below. Note that the following embodiments are examples for explaining the present invention and the present invention is not limited to the embodiments alone.
(First Embodiment)
[Oxygen-Absorbing Resin Composition]

The oxygen-absorbing resin composition of the embodiment at least contains a polyamide compound (hereinafter, simply referred also to a "tetralin ring-containing polyamide compound") containing at least one constituent unit having a tetralin ring selected from the group consisting of constituent units represented by the above general formulas (1) and (2) and a transition metal catalyst.
<Tetralin Ring-Containing Polyamide Compound>

The tetralin ring-containing polyamide compound to be used in the oxygen-absorbing resin composition of the embodiment contains at least one of the constituent units represented by the above general formulas (1) and (2). It is preferable that the constituent unit represented by the above general formula (1) is at least one selected from the group consisting of constituent units represented by the above formulas (3) to (6). The phrase of "contains . . . a constituent unit" herein means that one or more constituent units are contained in a compound. It is preferable that such a constituent unit is contained as a repeat unit in a tetralin ring-containing polyamide compound. Likewise, if a tetralin ring-containing polyamide compound is a polymer, the compound may be any one of a homopolymer of the above constituent unit, a random copolymer of the above constituent unit and another constituent unit, and a block copolymer of the above constituent unit and another constituent unit.

In the constituent units represented by the above general formulas (1) and (2), examples of the monovalent substituent represented by R include, but not particularly limited to, a halogen atom (for example, a chlorine atom, a bromine atom, an iodine atom), an alkyl group (a linear, branched or cyclic alkyl group having preferably 1 to 15 carbon atoms and more preferably 1 to 6 carbon atoms, such as a methyl group, an ethyl group, a n-propyl group, an isopropyl group, a t-butyl group, a n-octyl group, a 2-ethylhexyl group, a cyclopropyl group, and a cyclopentyl group), an alkenyl group (a linear, branched or cyclic alkenyl group having preferably 2 to 10 carbon atoms and more preferably 2 to 6 carbon atoms, such as a vinyl group and an allyl group), an alkynyl group (an alkynyl group having preferably 2 to 10 carbon atoms and more preferably 2 to 6 carbon atoms, such as an ethynyl group and a propargyl group), an aryl group (an aryl group having preferably 6 to 16 carbon atoms and more preferably 6 to 10 carbon atoms, such as a phenyl group and a naphthyl group), a heterocyclic group (a monovalent group obtained by removing a single hydrogen atom from a 5-member or 6-member aromatic or non-aromatic heterocyclic compound having preferably 1 to 12 carbon atoms and more preferable 2 to 6 carbon atoms, such as a 1-pyrazolyl group, a 1-imidazolyl group and a 2-furyl group), a cyano group, a hydroxy group, a carboxyl group, an ester group, an amido group, a nitro group, an alkoxy group (linear, branched or cyclic alkoxy group having preferably 1 to 10 carbon atoms and more preferably 1 to 6 carbon atoms, such as a methoxy group and an ethoxy group), an aryloxy group (an aryloxy group having preferably 6 to 12 carbon atoms and more preferably 6 to 8 carbon atoms, such as a phenoxy group), an acyl group (including a formyl group. An alkyl carbonyl group having preferably 2 to 10 carbon atoms and more preferably 2 to 6 carbon atoms, and an arylcarbonyl group having preferably 7 to 12 carbon atoms and more preferably 7 to 9 carbon atoms, such as an acetyl group, a pivaloyl group and a benzoyl group), an amino group (an alkylamino group having preferably 1 to 10 carbon atoms and more preferably 1 to 6 carbon atoms, an anilino group having preferably 6 to 12 carbon atoms and more preferably 6 to 8 carbon atoms, a heterocyclic amino group having preferably 1 to 12 carbon atoms and more preferably 2 to 6 carbon atoms, such as an amino group, a methylamino group and an anilino group), a mercapto group, an alkylthio group (an alkylthio group having preferably 1 to 10 carbon atoms and more preferably 1 to 6 carbon atoms, such as a methylthio group and an ethylthio group), an arylthio group (an arylthio group having preferably 6 to 12 carbon atoms and more preferably 6 to 8 carbon atoms, such as a phenylthio group), a heterocyclic thio group (a heterocyclic thio group having preferably 2 to 10 carbon atoms and more preferably 1 to 6 carbon atoms, such as a 2-benzothiazolylthio group), an imido group (an imido group having preferably 2 to 10 carbon atoms and more preferably 4 to 8 carbon atoms, such as a N-succinimido group and a N-phthalimido group).

Note that when the above monovalent substituent R has a hydrogen atom, the hydrogen atom may be further substituted with a substituent T (herein, substituent T is the same as defined in the above monovalent substituent R). Specific examples thereof include, but not particularly limited to, an alkyl group substituted with a hydroxy group (for example, a hydroxyethyl group), an alkyl group substituted with an alkoxy group (for example, a methoxyethyl group), an alkyl group substituted with an aryl group (for example, a benzyl group), an alkyl group substituted with a primary or secondary amino group (for example, an aminoethyl group), an aryl group substituted with an alkyl group (for example, a p-tolyl group) and an aryloxy group substituted with an alkyl group (for example, a 2-methylphenoxy group). Note that when the monovalent substituent R has a monovalent substituent T, the number of carbon atoms of the substituent T is not included in the number of carbon atoms mentioned above. For example, a benzyl group is regarded as an alkyl group having a single carbon atom substituted with a phenyl group and not regarded as an alkyl group having 7 carbon atoms substituted with a phenyl group. Furthermore, when the above monovalent substituent R has a substituent T, the substituent T may be plural.

In the constituent units represented by the above general formulas (1) and (2), X represents a divalent group containing at least one group selected from the group consisting of an aromatic hydrocarbon group, a saturated or unsaturated alicyclic hydrocarbon group, a linear or branched, saturated or unsaturated aliphatic hydrocarbon group, and a heterocyclic group. The aromatic hydrocarbon group, saturated or unsaturated alicyclic hydrocarbon group, linear or branched, saturated or unsaturated aliphatic hydrocarbon group, and heterocyclic group may be substituted or unsubstituted. X may contain a hetero atom or an ether group, a sulfide group, a carbonyl group, a hydroxy group, an amino group, a sulfoxide group or a sulfone group.

Herein, examples of the aromatic hydrocarbon group include, but not particularly limited to, an o-phenylene group, a m-phenylene group, a p-phenylene group, a methylphenylene group, an o-xylylene group, a m-xylylene group, a p-xylylene group, a naphthylene group, an anthracenylene group, a phenanthrylene group, a biphenylene group and a fluonylene group. Examples of the alicyclic hydrocarbon group include, but not particularly limited to, cycloalkenylene groups such as a cyclopentylene group, a cyclohexylene group, a methylcyclohexylene group, a cycloheptylene group and a cyclooctylene group; and cycloalkenylene groups such as a cyclohexycenylene group. Examples of the aliphatic hydrocarbon group include, but not particularly limited to, linear or branched alkylene groups such as a methylene group, an ethylene group, a trimethylene group, a propylene group, an isopropylidene group, a tetramethylene group, an isobutylidene group, a sec-butylidene group, a pentamethylene group, a hexamethylene group, a heptamethylene group, an octamethylene group, a nonamethylene group and a dacamethylene group; and alkenylene groups such as a vinylene group, a propenylene group, a 1-butenylene group, a 2-butenylene group, a 1,3-butadienylene group, a 1-pentenylene group, a 2-pentenylene group, a 1-hexenylene group, a 2-hexenylene group and a 3-hexenylene group. These may further have a substituent. Specific examples thereof include, but not particularly limited to, a halogen, an alkoxy group, a hydroxy group, a carboxyl group, a carboalkoxy group, an amino group, an acyl group, a thio group (for example, an alkylthio group, a phenylthio group, a tolylthio group and a pyridylthio group), an amino group (for example, an unsubstituted amino group, a methylamino group, a dimethylamino group and a phenylamino group), a cyano group and a nitro group.

The tetralin ring-containing polyamide compound having the constituent unit represented by the above general formula (1) can be obtained, for example, by polycondensation of a dicarboxylic acid having a tetralin ring or a derivative (I) thereof and a diamine or a derivative (II) thereof.

Examples of the dicarboxylic acid having a tetralin ring or a derivative (I) thereof include compounds represented by the following general formula (7). The dicarboxylic acids having a tetralin ring or derivatives (I) thereof can be used alone or in combination with two or more.

[Formula 3]

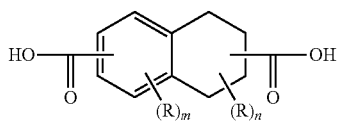

(7)

where R each independently represents a monovalent substituent, which is at least one selected from the group consisting of a halogen atom, an alkyl group, an alkenyl group, an alkynyl group, an aryl group, a heterocyclic group, a cyano group, a hydroxy group, a carboxyl group, an ester group, an amido group, a nitro group, an alkoxy group, an aryloxy group, an acyl group, an amino group, a mercapto group, an alkylthio group, an arylthio group, an heterocyclic thio group and an imido group, these of which may further have a substituent; m represents an integer of 0 to 3; n represents an integer of 0 to 6, and at least one hydrogen atom is bound to the benzyl position of the tetralin ring.

Note that a compound represented by the above general formula (7) can be obtained by reacting, for example, a dicarboxylic acid having a naphthalene ring represented by the following general formula (8) or a derivative thereof with hydrogen.

[Formula 4]

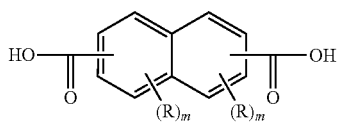

(8)

where R each independently represents a monovalent substituent, which is at least one selected from the group consisting of a halogen atom, an alkyl group, an alkenyl group, an alkynyl group, an aryl group, a heterocyclic group, a cyano group, a hydroxy group, a carboxyl group, an ester group, an amido group, a nitro group, an alkoxy group, an aryloxy group, an acyl group, an amino group, a mercapto group, an alkylthio group, an arylthio group, an heterocyclic thio group and an imido group, these of which may further have a substituent; and m each independently represents an integer of 0 to 3.

Examples of the diamine or a derivative thereof (II) include linear saturated aliphatic diamines such as ethylenediamine, trimethylenediamine, tetramethylenediamine, pentamethylenediamine, hexamethylenediamine, heptamethylenediamine, octamethylenediamine, nonamethylenediamine, decamethylenediamine, undecamethylenediamine, dodecamethylenediamine and tridecamethylenediamine; branched saturated aliphatic amines such as 2-methylpentamethylenediamine, 2,2,4-trimethylhexamethylenediamine, 2-methyloctamethylenediamine and 2,4-dimethyloctamethylenediamine; alicyclic amines such as 1,3-cyclohexanediamine, 1,4-cyclohexanediamine, 1,3-bis (aminomethyl)cyclohexane and 1,4-bis (aminomethyl)cyclohexane; and aromatic amines such as metaxylylenediamine, para-xylylenediamine, metaphenylenediamine and paraphenylenediamine; or these derivatives. These diamines or derivatives thereof (II) can be used alone or in combination with two or more.

A tetralin ring-containing polyamide compound containing a constituent unit represented by the above general formula (2) can be obtained, for example, by polycondensation of a diamine having a tetralin ring or a derivative (III) thereof and a dicarboxylic acid or a derivative (IV) thereof.

Examples of the diamine having a tetralin ring or a derivative (III) thereof include compounds represented by the following general formula (9). The diamine having a tetralin ring or derivatives (III) thereof can be used alone or in combination with two or more.

[Formula 5]

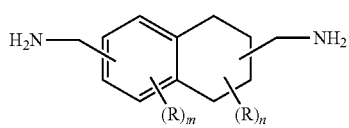

(9)

where R each independently represents a monovalent substituent, which is at least one selected from the group consisting of a halogen atom, an alkyl group, an alkenyl group, an alkynyl group, an aryl group, a heterocyclic group, a cyano group, a hydroxy group, a carboxyl group, an ester group, an amido group, a nitro group, an alkoxy group, an aryloxy group, an acyl group, an amino group, a mercapto group, an alkylthio group, an arylthio group, a heterocyclic thio group and an imido group, these of which may further have a substituent; m represents an integer of 0 to 3; n represents an integer of 0 to 6, and at least one hydrogen atom is bound to the benzyl position of the tetralin ring.

Note that a compound represented by the above general formula (9) can be obtained by reacting, for example, a diamine having a naphthalene ring represented by the following general formula (10) or a derivative thereof with hydrogen.

[Formula 6]

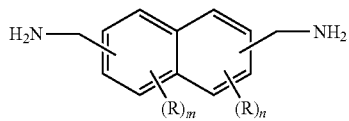

(10)

where R each independently represents a monovalent substituent, which is at least one selected from the group consisting of a halogen atom, an alkyl group, an alkenyl group, an alkynyl group, an aryl group, a heterocyclic group, a cyano group, a hydroxy group, a carboxyl group, an ester group, an amido group, a nitro group, an alkoxy group, an aryloxy group, an acyl group, an amino group, a mercapto group, an alkylthio group, an arylthio group, a heterocyclic thio group and an imido group, these of which may further have a substituent; m each independently represents an integer of 0 to 3.

Examples of the dicarboxylic acid or a derivative (IV) thereof include benzene dicarboxylic acids such as oxalic acid, adipic acid, pimelic acid, suberic acid, azelaic acid, sebacic acid, undecane diacid, dodecane diacid, 3,3-dimethylpentane diacid, phthalic acid, isophthalic acid and terephthalic acid, and naphthalene dicarboxylic acids such as 2,6-naphthalene dicarboxylic acid, anthracene dicarboxylic acid, phenyl malonic acid, phenylene diacetic acid, phenylene dibutyric acid, 4,4-diphenyletherdicarboxylic acid and p-phenylene dicarboxylic acid or derivatives of these. Dicarboxylic acids or derivatives (IV) thereof can be used alone or in combination with two or more.

A tetralin ring-containing polyamide compound containing a constituent unit represented by the above general formula (1) or (2) can be also obtained, for example, by reacting a polyamide compound containing a constituent unit represented by the following general formula (11) or (12) with hydrogen.

[Formula 7]

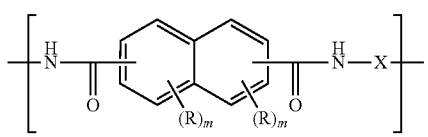

(11)

where R each independently represents a monovalent substituent, which is at least one selected from the group consisting of a halogen atom, an alkyl group, an alkenyl group, an alkynyl group, an aryl group, a heterocyclic group, a cyano group, a hydroxy group, a carboxyl group, an ester group, an amido group, a nitro group, an alkoxy group, an aryloxy group, an acyl group, an amino group, a mercapto group, an alkylthio group, an arylthio group, a heterocyclic thio group and an imido group, these of which may further have a substituent; m each independently represents an integer of 0 to 3; X represents a divalent group containing at least one group selected from the group consisting of an aromatic hydrocarbon group, a saturated or unsaturated alicyclic hydrocarbon group, a linear or branched, saturated or unsaturated aliphatic hydrocarbon group, and a heterocyclic group.

[Formula 8]

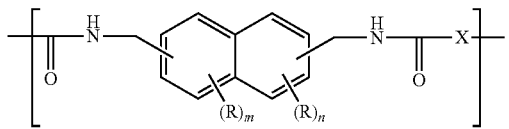

(12)

where R each independently represents a monovalent substituent, which is at least one selected from the group consisting of a halogen atom, an alkyl group, an alkenyl group, an alkynyl group, an aryl group, a heterocyclic group, a cyano group, a hydroxy group, a carboxyl group, an ester group, an amido group, a nitro group, an alkoxy group, an aryloxy group, an acyl group, an amino group, a mercapto group, an alkylthio group, an arylthio group, a heterocyclic thio group and an imido group, these of which may further have a substituent; m each independently represents an integer of 0 to 3; X represents a divalent group containing at least one group selected from the group consisting of an aromatic hydrocarbon group, a saturated or unsaturated alicyclic hydrocarbon group, a linear or branched, saturated or unsaturated aliphatic hydrocarbon group, and a heterocyclic group.

Specific examples of the monovalent substituents represented by R and the divalent group represented by X in the constituent units represented by the above general formulas (7) to (12) are the same as those described in the constituent units represented by the above general formulas (1) and (2). Thus, repetition of explanation is avoided herein.

The tetralin ring-containing polyamide compound to be used in the oxygen-absorbing resin composition of the embodiment may contain another constituent unit having a tetralin ring other than the constituent units represented by the above general formulas (1) and (2) and/or a constituent unit having no tetralin ring as a copolymerization component(s). Specifically, the compounds mentioned above as a diamine or a derivative (II) thereof and a dicarboxylic acid or a derivative (IV) thereof can be used as the copolymerization component(s). Furthermore, an ω-aminocarboxylic acid unit represented by the following general formula (13) may be further contained.

[Formula 9]

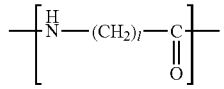

(13)

where l represents an integer of 2 to 18.

Examples of a compound that can constitute an ω-aminocarboxylic acid unit represented by the above general formula (13) include an ω-aminocarboxylic acid having 3 to 19 carbon atoms and a lactam having 3 to 19 carbon atoms. Examples of the ω-aminocarboxylic acid having 3 to 19 carbon atoms include 6-amino hexanonic acid and 12-aminododecanoic acid. Examples of the lactam having 3 to 19 carbon atoms include ε-caprolactum and laurolactam. They are not limited to these. These can be used alone or in combination with two or more.

As more preferable compounds among the tetralin ring-containing polyamide compounds containing a constituent unit represented by the above general formula (1), tetralin ring-containing polyamide compounds containing constituent units represented by the above formulas (3) to (6) are mentioned.

The molecular weight of the above tetralin ring-containing polyamide compounds, which can be appropriately specified in consideration of desired performance, handling property, and the like, is not particularly limited. Generally, the weight average molecular weight (Mw) is preferably $1.0 \times 10^3$ to $8.0 \times 10^6$ and more preferably $5.0 \times 10^3$ to $5.0 \times 10^6$. Similarly, the number average molecular weight (Mn) thereof is preferably $1.0 \times 10^3$ to $1.0 \times 10^6$ and more preferably $5.0 \times 10^3$ to $5.0 \times 10^4$. Note that the molecular weights used herein each refer to a polystyrene equivalent value. Note that the above tetralin ring-containing polyamide compounds can be used alone or in combination with two or more.

The glass transition temperature (Tg) of a tetralin ring-containing polyamide compound as mentioned above, which is not particularly limited, is preferably 0 to 150° C. and more preferably 10 to 130° C. Note that the glass transition temperature herein refers to a value measured by differential scanning calorimetry.

A method for producing the above tetralin ring-containing polyamide compound is not particularly limited and any conventional method for producing a polyamide can be applied. Examples of the method for producing a polyamide include a pressurized salt method, an atmospheric dropping method and a pressurized dropping method. Of them, a pressurized salt method is preferred.

The pressurized salt method is a polycondensation method of raw materials, i.e., a dicarboxylic acid and a diamine salt under pressure. To describe more specifically, an aqueous solution containing a salt of a dicarboxylic acid and a diamine in a predetermined molar ratio is prepared and concentrated. Subsequently, the temperature of the aqueous solution is raised under pressure and a polycondensation is performed while removing condensation water.

The atmospheric dropping method is a method including melting a dicarboxylic acid by heating, continuously adding a diamine dropwise under normal pressure, and performing polycondensation while removing condensation water. At this time, the polycondensation reaction is performed while raising the temperature in such a manner that the reaction temperature is not lowered than the melting point of the tetralin ring-containing polyamide compound to be produced. When the predetermined molar ratio is satisfied, addition of the diamine is terminated, the temperature of the reaction mixture is raised to a temperature, which is about 10° C. as high as the melting point of the tetralin ring-containing polyamide compound. While the reaction mixture is maintained at the temperature for a predetermined time, polycondensation is continued to obtain the polyamide compound.

The pressurized dropping method is a method including melting a dicarboxylic acid by heating, continuously adding a diamine dropwise under pressure, preferably about 0.3 to 0.4 MPaG, and performing polycondensation while removing condensation water. At this time, the polycondensation reaction is performed while raising the temperature in such a manner that the reaction temperature is not lowered than the melting point of the tetralin ring-containing polyamide compound to be produced. When the predetermined molar ratio is satisfied, addition of the diamine is terminated. While gradually returning the pressure to normal pressure, the temperature of the reaction mixture is raised to a temperature, which is about 10° C. as high as the melting point of the tetralin ring-containing polyamide compound and maintained at the temperature for a predetermined time. In this manner, polycondensation is continued to obtain the polyamide compound.

The tetralin ring-containing polyamide compound produced by the above polycondensation method can be used as it is; however, the compound may be further subjected to a step for increasing a polymerization degree. As the step of further increasing a polymerization degree, for example, a reaction and extrusion within an extruder and solid-phase polymerization are mentioned. As a heating apparatus for use in the solid-phase polymerization, for example, a continuous heating/drying apparatus; a rotary-drum heating apparatus called a tumble dryer, a conical dryer and a rotary dryer; and a conical heating apparatus having a rotary screw therein, called a nauta mixer can be preferably used. However, the heating apparatus is not limited to these and methods and apparatuses known in the art can be used. When solid-phase polymerization of a tetralin ring-containing polyamide compound is performed, the rotary-drum heating apparatus of the aforementioned apparatuses is particularly preferably used since the system can be hermetically closed and polycondensation can be easily performed while eliminating oxygen causing coloration.

In producing a tetralin ring-containing polyamide compound, a conventional stabilizer such as a heat stabilizer and a photo stabilizer, a conventional polymerization moderator, and the like may be used. The types and use amounts of these may be appropriately selected depending upon the reaction rate, the molecular weight of a tetralin ring-containing polyamide compound, glass transition temperature, viscosity, color tone, safety, heat stability, weather resistance, elution properties themselves, and the like and are not particularly limited.

Note that, the relative viscosity of a tetralin ring-containing polyamide compound, in view of the strength and appearance of a molded article and molding processability, is preferably 1.8 to 4.2, more preferably, 1.9 to 4.0 and further preferably 2.0 to 3.8. The "relative viscosity" used herein refers to the ratio of dropping time (t) of a tetralin ring-containing polyamide compound (1 g) dissolved in a 96% sulfuric acid (100 mL) and measured at 25° C., by a Cannon Fenske viscometer, based on the dropping time (t0) of 96% sulfuric acid itself, measured in the same manner, and expressed by the following expression.

$$\text{Relative viscosity} = t/t0$$

The above tetralin ring-containing polyamide compounds all have hydrogen at the benzyl position of the tetralin ring. Since the hydrogen at the benzyl position is removed by using a tetralin ring-containing polyamide compound in combination with a transition metal catalyst as mentioned above, more excellent oxygen absorptivity is exhibited.

The oxygen-absorbing resin composition of the embodiment is significantly suppressed in odor generation after absorption of oxygen. The reason is not elucidated; however, for example, the following oxidation reaction mechanism is presumable. In the tetralin ring-containing polyamide compound as mentioned above, first hydrogen at the benzyl position of the tetralin ring is removed to produce a radical. The radical then reacts with oxygen to oxidize carbon at the benzyl position. In this manner, a hydroxy group or a ketone group is considered to be produced. Because of this, it is presumed that, in the oxygen-absorbing resin composition of the embodiment, a molecular chain of a main oxygen-absorbing component is not cut by an oxidation reaction as is in the prior art and the structure of a tetralin ring-containing polyamide compound is maintained, with the result that a low molecular weight organic compound serving as a cause of odor is rarely produced after absorption of oxygen.

<Transition Metal Catalyst>

As the transition metal catalyst to be used in the oxygen-absorbing resin composition of the embodiment, any catalyst known in the art can be appropriately selected and used as long as it can serve as a catalyst for the oxidation reaction of a tetralin ring-containing polyamide compound as mentioned above. The transition metal catalyst is not particularly limited.

Specific examples of such a transition metal catalyst include organic acid salts, halides, phosphates, phosphites, hypophosphites, nitrates, sulfates, oxides and hydroxides of transition metals. Examples of the transition metal to be contained in the transition metal catalyst include, but not limited to, titanium, vanadium, chromium, manganese, iron, cobalt, nickel, copper, zinc, ruthenium and rhodium. Of them, manganese, iron, cobalt, nickel and copper are preferable. Examples of the organic acids include, but not limited to, acetic acid, propionic acid, octanoic acid, lauric acid, stearic acid, acetylacetone, dimethyldithiocarbamic acid, palmitic acid, 2-ethylhexanoic acid, neodecanoic acid, linoleic acid, tall acid, oleic acid, capric acid and naphthenic acid. The transition metal catalyst is preferably a combination of a transition metal as mentioned above and an organic acid, and more preferably a combination of a transition metal such as manganese, iron, cobalt, nickel or copper and an organic acid such as acetic acid, stearic acid, 2-ethylhexanoic acid, oleic acid or naphthenic acid. Note that transition metal catalysts can be used alone or in combination with two or more.

In the oxygen-absorbing resin composition of the embodiment, the content rate of a tetralin ring-containing polyamide compound and a transition metal catalyst, which can be appropriately specified depending upon the types of tetralin ring-containing polyamide compound and transition metal catalyst to be used and the desired performances thereof, is not particularly limited. In view of the amount of oxygen absorbed of oxygen-absorbing resin composition, the content of a transition metal catalyst is preferably 0.001 to 10 parts by mass in terms of transition metal based on 100 parts by mass of a tetralin ring-containing polyamide compound, and more preferably 0.002 to 2 parts by mass, and further preferably 0.005 to 1 part by mass.

<Other Thermoplastic Resin>

The oxygen-absorbing resin composition of the embodiment, if necessary, may further contain another thermoplastic resin other than a tetralin ring-containing polyamide compound as mentioned above. If another thermoplastic resin is used in combination, moldability and handling property can be enhanced.

As another thermoplastic resin, those known in the art can be appropriately used. Examples thereof include, but not limited to, polyolefins such as random or block copolymers of α-olefins such as a low-density polyethylene, a medium-density polyethylene, a high-density polyethylene, a linear and low-density polyethylene, a linear and extremely low-density polyethylene, a polypropylene, poly-1-butene, poly-4-methyl-1-pentene or ethylene, propylene, 1-butene, and 4-methyl-1-pentene; acid-modified polyolefins such as maleic anhydride-grafted polyethylene and maleic anhydride-grafted polypropylene; ethylene-vinyl compound copolymers such as an ethylene-vinyl acetate copolymer, an ethylene-vinyl chloride copolymer, an ethylene-(meth)acrylate copolymer, an ion crosslinked product (ionomer) thereof and an ethylene-methyl methacrylate copolymer; styrene resins such as polystyrene, an acrylonitrile-styrene copolymer and an α-methylstyrene-styrene copolymer; polyvinyl compounds such as poly(methyl acrylate) and poly(methyl methacrylate); polyamides such as nylon 6, nylon 66, nylon 610, nylon 12, poly(metaxylylene adipamide) (MXD6); polyesters such as poly(ethylene terephthalate) (PET), poly (butylene terephthalate) (PBT), poly(trimethylene terephthalate) (PTT), poly(ethylene naphthalate) (PEN), glycol-modified poly(ethylene terephthalate) (PETG), poly (ethylene succinate) (PES), poly(butylene succinate) (PBS), polylactate, polyglycolate, polycaprolactone and polyhydroxyalkanoate; polycarbonates; polyethers such as polyethylene oxide; and mixtures of these. These thermoplastic resins can be used alone or in combination with two or more.

The thermoplastic resin to be added, if necessary, to a tetralin ring-containing polyamide compound and a transition metal catalyst can be mixed in accordance with a method known in the art. If these are kneaded by use of an extruder, an oxygen-absorbing resin composition having higher dispersibility can be obtained.

<Additives>

The oxygen-absorbing resin composition of the embodiment herein may contain additives known in the art other than the aforementioned components, as long as the effect of the embodiment is not excessively damaged. Examples of such optional additives include, but not particularly limited to, additives such as a drying agent, a pigment such as titanium oxide, a dye, an antioxidant, a slipping agent, an antistatic agent and a stabilizer; fillers such as calcium carbonate, clay, mica and silica; and a deodorant.

The oxygen-absorbing resin composition of the embodiment may further contain a radical generator and a photo initiator, if necessary, in order to facilitate an oxygen absorption reaction. Specific examples of the radical generator include various types of N-hydroxy imide compounds. Specific examples thereof include, but not particularly limited to, N-hydroxysuccinimide, N-hydroxymaleimide, N,N'-dihydroxycyclohexanetetracarboxydiimide, N-hydroxyphthalimide, N-hydroxytetrachlorophthalimide, N-hydroxytetrabromophthalimide, N-hydroxyhexahydrophthalimide, 3-sulfonyl-N-hydroxyphthalimide, 3-methoxycarbonyl-N-hydroxyphthalimide, 3-methyl-N-hydroxyphthalimide, 3-hydroxy-N-hydroxyphthalimide, 4-nitro-N-hydroxyphthalimide, 4-chloro-N-hydroxyphthalimide, 4-methoxy-N-hydroxyphthalimide, 4-dimethylamino-N-hydroxyphthalimide, 4-carboxy-N-hydroxyhexahydrophthalimide, 4-methyl-N-hydroxyhexahydrophthalimide, N-hydroxyhetimide, N-hydroxyhimimide, N-hydroxytrimellitimide and N,N-dihydroxypyromellitdiimide. Specific examples of the photo initiator include, but not particularly limited to, benzophenone and a derivative thereof, a thiazine dye, a metal porphyrin derivative and an anthraquinone derivative. Note that these radical generators and photo initiators can be used alone or in combination with two or more.

<Usage>

To the oxygen-absorbing resin composition of the embodiment, a known granulation method or a known molding method such as an extrusion molding can be applied. The composition is molded into, for example, powdery, granular, pellet, film or sheet-forms or other small-piece forms. The oxygen-absorbing resin molded article thus obtained can be used directly as an oxygen absorbent. Alternatively, if the obtained oxygen-absorbing resin molded article is packed in an air-permeable packaging material, the molded article can also be used as an oxygen absorbent packaging body. Furthermore, if the oxygen-absorbing resin composition of the embodiment is molded into film-form or sheet-form, the molded article can also be used in the form of a label, a card, a packing, and the like. Note that a molded article having a thickness of 0.1 to 500 μm is specified as a film, whereas a molded article having a thickness exceeding 500 μm is specified as a sheet.

It is preferable that a pellet-form oxygen-absorbing resin molded article herein is further ground into powdery grains when used in order to increase the contact area with oxygen to thereby effectively deliver oxygen-absorbing performance.

Note that as the air-permeable packaging material, which is not particularly limited, a known packaging material having air permeability can be applied. In view of sufficiently exerting the oxygen absorption effect, an air-permeable packaging material having high air permeability is preferred. Specific examples of the air-permeable packaging material include, but not particularly limited to, highly air-permeable packaging materials used in various usages, including paper sheets such as Japanese paper, machine-made paper and rayon paper; non-woven clothes using various types of fibers obtained from pulp, cellulose and a synthetic resin; a plastic film or a porous plastic film; or a microporous film obtained by adding calcium carbonate etc., followed by drawing it; and a laminate obtained by stacking two types or more selected from these. As the plastic film, laminate films, each formed by laminating and attaching a film of e.g., a polyethylene terephthalate, a polyamide, a polypropylene or a polycarbonate film and a film serving as a sealing film and formed of a polyethylene, an ionomer, a polybutadiene, an ethylene acrylate copolymer, an ethylene methacrylate copolymer or an ethylene vinyl acetate copolymer, can be used.

Note that if the oxygen-absorbing resin composition of the embodiment is molded into a film form or a sheet form and put in use, it is preferable to form micro voids in the film or the sheet, for example, by drawing. Owing to this operation, the oxygen permeability of the film or sheet molded can be enhanced, with the result that the oxygen-absorbing performance of the tetralin ring-containing polyamide compound mentioned above tends to be extremely effectively delivered. Furthermore, if an oxygen-absorbing resin composition contains a polyolefin resin, the polyolefin resin and a tetralin ring-containing polyamide compound may possibly form an island structure in a film or a sheet. In this case, it is preferable to form voids in the interface between them, for example, by drawing. As the polyolefin resin that is used in drawing a film or a sheet in this way, a high-density polyethylene is preferable.

The oxygen-absorbing resin composition of the embodiment molded into a film form or a sheet form can be not only used as a packaging material or a packaging container in the form of a single-layer form but also used in combination with another substrate in the form of a laminate. Typical example of such a laminate is a laminate obtained by stacking at least one layer formed of the oxygen-absorbing resin composition of the embodiment and at least one layer selected from other resin layers, paper substrate layers or metal foil layers. This laminate can be used as an oxygen-absorbing multi-layer packaging material and an oxygen-absorbing multi-layer packaging container. Note that, the oxygen-absorbing resin composition of the embodiment molded into film-form or sheet form and an oxygen-absorbing layer formed of the composition are generally preferably provided to an interior side rather than the outer surface of a container etc. so as not to be exposed at the outer surface of the container etc. In view of avoiding direct contact with the content of a container, the oxygen-absorbing resin composition of the embodiment molded into a film form or a sheet form and an oxygen-absorbing layer formed of the composition are preferably provided outer than the inner surface of the container etc. Likewise, in using the oxygen-absorbing resin composition of the embodiment and the oxygen-absorbing layer formed of the composition in a multilayer body, it is preferable that the composition is molded into a film form or a sheet form and arranged as at least one intermediate layer.

Examples of one preferable aspect of the laminate mentioned above include an oxygen-absorbing multilayer body having at least three layers, i.e., a sealant layer containing a thermoplastic resin, an oxygen-absorbing layer containing the oxygen-absorbing resin composition of the embodiment and a gas barrier layer containing a gas barrier substance, in this order. The phrase "having at least three layers . . . in this order" means that the sealant layer, oxygen-absorbing layer and gas barrier layer are arranged in this order; and is a concept including not only an aspect where a sealant layer, an oxygen-absorbing layer and a gas barrier layer are directly stacked (hereinafter, expressed as a "sealant layer/oxygen-absorbing layer/gas barrier layer") but also an aspect where one or more other layers such as a resin layer, a metal foil layer or an adhesive layer are interposed between a sealant layer and an oxygen-absorbing layer or between an oxygen-absorbing layer and a gas barrier layer (hereinafter, referred to as an "intermediate layer") (for example, "sealant layer/resin layer/oxygen-absorbing layer/adhesion layer/gas barrier layer", and "sealant layer/resin layer/adhesion layer/oxygen-absorbing layer/adhesion layer/resin layer/adhesion layer/gas barrier layer/adhesion layer/support") (the same applied hereinafter without an exception).

Examples of another preferable aspect of the laminate mentioned above include an oxygen-absorbing multilayer body having at least three layers, i.e., a sealant layer having a polyolefin resin, an oxygen-absorbing layer containing the oxygen-absorbing resin composition of the embodiment and a gas barrier layer containing a gas barrier substance in this order.

As the thermoplastic resin and polyolefin resin used in the sealant layer, the same thermoplastic resins and polyolefin resins described in the oxygen-absorbing resin composition of the embodiment can be used. It is preferable that the thermoplastic resin and polyolefin resin to be used in the sealant layer are appropriately selected in consideration of compatibility with other layers (oxygen-absorbing layer, gas barrier layer, resin layer, adhesive layer, support, etc.) in adjacent to the sealant layer.

As the gas barrier substance to be used as a gas barrier layer, a gas barrier thermoplastic resin, a gas barrier thermosetting resin, silica, alumina, aluminum, etc., (as vapor deposition films) and a metal (as aluminum in the form of foil) can be used. Examples of the gas barrier thermoplastic resin include an ethylene-vinyl alcohol copolymer, MXD6 and poly(vinylidene chloride). As the gas barrier thermosetting resin, a gas barrier epoxy resin, for example, "MAXIVE" manufactured by Mitsubishi Gas Chemical Company, Inc., can be mentioned.

As a method for manufacturing an oxygen-absorbing multilayer body as mentioned above, which is not particularly limited, known methods such as a coextrusion method, a laminating method and a coating method can be applied depending upon e.g., the properties of the material, purpose of processing and processing step. For example, a film or a sheet can be formed by a manufacturing method of extruding a molten resin composition from an extruder provided with e.g., a T die and a circular die or by a method of applying an adhesive to an oxygen-absorbing film or a sheet and adhering it to another film or sheet. Also, if molten resins are simultaneously injected or sequentially injected through multi-layered multiple dies into an injection mold by use of an injector, a multilayer container or a preform for manufacturing a container having a predetermined shape can be formed. The preform is heated to a drawing temperature and stretched in the axis direction and simultaneously stretched in the circumferential direction in accordance with stretch blow-molding by hydrostatic pressure to obtain a bottle.

For example, a film-form oxygen-absorbing multilayer body can be further processed into a bag-form or a cover material. For example, a sheet-form oxygen-absorbing multilayer body is thermoformed into an oxygen-absorbing multilayer container of a predetermined shape such as a tray, a cup, a bottle and a tube by a molding method such as vacuum molding, air-pressure forming and plug assist molding. The bag-form container, if it is filled with stuff such as food and an open hole is provided, can be preferably used as a pouch for microwave cooking provided with a hole for easily releasing water vapor during microwave cooking.

In using the oxygen-absorbing resin composition of the embodiment and various types of moldings such as laminates using the composition, initiation of an oxygen absorption reaction can be facilitated and an oxygen-absorbing rate can be increased by irradiation of an energy beam. Examples of the usable energy beam include visible ray, UV ray, X-ray, electron ray and γ ray. The amount of irradiation energy can be appropriately selected depending upon the type of energy line to be used.

The oxygen-absorbing resin composition of the embodiment and various types of moldings such as laminates and containers using the composition do not require a moisture content for absorbing oxygen. In other words, oxygen can be absorbed regardless of the presence or absence of the moisture content of an article to be packed. Thus, the composition and moldings can be used in a wide variety of uses no matter which type of the article to be packed is contained. In particular, no odor is produced after absorption of oxygen, the composition and moldings can be particularly preferably used in e.g., foods, cooking foods, beverages, health foods and medicinal products. More specifically, since the oxygen-absorbing resin composition of the embodiment and various types of moldings such as laminates using the composition are excellent in oxygen-absorbing performance in a wide range of humidity conditions from low humidity to high humidity (relative humidity 0% to 100%) and excellent in taste and flavor retention property of a content, they are suitable for packaging various articles. In addition, unlike a conventional oxygen-absorbing resin composition using iron powder, the oxygen-absorbing resin composition of the embodiment can be suitably used for storing an article to be packed (for example, alcohol beverages and carbonate beverages) which cannot be stored because of the presence of iron.

Specific examples of the article to be packed include, but not particularly limited to, beverages such as cow milk, juice, coffee, tea and alcohol beverage; liquid seasonings such as source, soy sauce, noodle broth and dressing; cooking foods such as soup, stew and curry; paste foods such as jam and mayonnaise; seafood products such as tuna and fish and shellfish; processed milk products or processed egg products such as cheese, butter and egg; processed livestock products such as meat, salami sausage, sausage and ham; vegetables such as carrot, potato, asparagus and shiitake mushroom; fruits; egg; noodles; rices such as rice and polished rice; cereals such as beans; processed rice foods or processed cereal foods such as steamed rice, festive red rice, rice cake and rice gruel; confectioneries such as adzuki-bean jelly, pudding, cake and steamed bean-jam buns; dry foods (food having a low water activity) such as powdered seasoning, powdered coffee, coffee bean, tea, powdered milk for infants, cooking food for infants, powdered dietary food, nursing care cooking food, dry vegetable, Japanese cracker and rice cracker; chemical products such as an adhesive, a gluing agent, an agrochemical and a pesticide; medicinal products; health foods such as a vitamin supplement; pet foods; sundry articles such as a cosmetic, a shampoo, a conditioner and a detergent; and other various articles. Particularly, the oxygen-absorbing resin composition of the embodiment is suitable for packaging materials for an article to be packed easily degrading in the presence of oxygen. Examples of such an article to be packed include beverages such as beer, wine, Japanese sake, shochu, fruit juice beverage, fruit juice, vegetable juice, carbonate soft drink and tea; foods such as fruit, nut, vegetable, meat products, infant food, coffee, jam, mayonnaise, ketchup, edible oil, dressing, source, food boiled in soy sauce and milk products; and others such as medicinal products and cosmetics. Note that the term "water activity" refers to a scale showing the content of free water in an article and represented by a numeral from 0 to 1. The article containing no water is represented by 0 and pure water is represented by 1. More specifically, the water activity Aw of an article is defined as follows:

$$Aw=P/P0=RH/100$$

where P represents a water vapor pressure of a space where an article is sealed and the state of the space reaches equivalent, P0 represents the water vapor pressure of pure water and RH (%) represents the relative humidity of the space.

Note that before and after filling (packaging) of an article to be packed, the container and the article to be packed can be sterilized by a method suitable for the article to be packed. Examples of the sterilization method include heat treatment such as a hot water treatment performed at 100° C. or less and a hot water treatment under pressure performed at 100° C. or more and a heat treatment performed at an ultra-high temperature of 130° C. or more; a sterilization with an electromagnetic wave such as UV rays, microwave and gamma ray; a gas treatment performed with ethylene oxide etc.; and sterilization with a chemical agent such as hydrogen peroxide and hypochlorite.

More specific embodiment using the oxygen-absorbing resin composition of the first embodiment will be described in detail below.

(Second Embodiment)

Now, the second embodiment of the present invention will be described below. Note that repetition of explanation with respect to the same content as in the first embodiment is avoided herein.

[Oxygen-Absorbing Multilayer Body]

The oxygen-absorbing multilayer body of the embodiment is obtained by laminating at least three layers, i.e., a sealant layer (layer C) containing a thermoplastic resin, an oxygen-absorbing layer (layer A) formed of an oxygen-absorbing resin composition containing a tetralin ring-containing polyamide compound and a transition metal catalyst, and a gas barrier layer (layer D) containing a gas barrier substance, in this order. Similarly to the first embodiment, the oxygen-absorbing multilayer body of the embodiment may have a layer other than these three layers in any position, if necessary.

By using the oxygen-absorbing multilayer body of the embodiment in part or in whole of a packaging container for sealing such that layer C faces inside, oxygen within the container can be absorbed (even if the amount of oxygen transmitting or coming into the container from the outside through the wall of the container is small, transmitting or incoming oxygen is also absorbed) to prevent deterioration etc. of the content (the article to be packed) stored therein by oxygen.

[Sealant Layer (Layer C)]

The sealant layer (layer C) of the oxygen-absorbing multilayer body of the embodiment contains a thermoplastic resin. Layer C has, in addition to a role as a sealant, a role in transmitting oxygen in the container up to an oxygen-absorbing layer; at the same time, isolating the content (the article to be packed) from the oxygen-absorbing layer (layer A) (inhibiting physical contact between layer A and the article to be packed). The oxygen transmission rate of layer C measured in the case of a film having a thickness of 20 μm at 23° C. under the conditions of a relative humidity of 60% is preferably 300 mL/(m²·day·atm) or more, more preferably 400 mL/(m²·day·atm) or more and further preferably 500 mL/(m²·day·atm) or more. If the oxygen transmission rate satisfies the aforementioned preferable values or more, the oxygen-absorbing rate of layer A can be more enhanced, compared to the case where the oxygen transmission rate does not satisfy the above values.

Examples of the thermoplastic resin to be used in layer C of the oxygen-absorbing multilayer body of the embodiment include polyethylenes such as a high-density polyethylene, a medium-density polyethylene, a low-density polyethylene, linear and low-density polyethylene, a linear and extremely low-density polyethylene and a polyethylene obtained in the presence of a metallocene catalyst; polystyrenes; polymethylpentenes; polypropylenes such as a propylene homo polymer, a propylene-ethylene block copolymer and a propylene-ethylene random copolymer; polyesters having a heat sealing property such as PET, A-PET, PETG and PBT; and amorphous nylon. These can be used alone or in a combination. To these thermoplastic resins, if necessary, an ethylene-vinyl acetate copolymer, an ethylene-methyl acrylate copolymer, an ethylene-ethyl acrylate copolymer, an ethylene-acrylate copolymer, an ethylene-methacrylate copolymer, an ethylene-methyl methacrylate copolymer and a thermoplastic elastomer may be added. As the thermoplastic resin to be used in layer C of the oxygen-absorbing multilayer body of the embodiment, a thermoplastic resin having a melt-flow rate (hereinafter referred to as an "MFR") at 200° C. of 1 to 35 g/10 minutes or an MFR at 240° C. of 2 to 45 g/10 minutes is preferably used in consideration of moldability and processability of the multilayer body.

Furthermore, layer C of the oxygen-absorbing multilayer body of the embodiment may contain additives known in the art other than a thermoplastic resin as mentioned above. Examples of such optional components include, but not particularly limited to, additives such as a drying agent, a pigment such as titanium oxide, a dye, an antioxidant, a slipping agent, an antistatic agent, a plasticizer, a stabilizer and a lubricant; fillers such as calcium carbonate, clay, mica and silica; and a deodorant. Particularly, in view of recycling and reprocessing offcuts generated during manufacturing, it is preferable to add an antioxidant to layer C.

The content rate of the thermoplastic resin in layer C, which can be appropriately specified, is not particularly limited; however the content rate is preferably 70 to 100 mass % based on the total amount of layer C, more preferably 80 to 100 mass % and further preferably 90 to 100 mass %. The thermoplastic resin to be used in layer C of the embodiment preferably contains a thermoplastic resin other than a tetralin ring-containing polyamide compound as described in the first embodiment, in an amount of 50 to 100 mass % based on the total amount of the thermoplastic resin contained in the layer C, more preferably 70 to 100 mass % and further preferably 90 to 100 mass %.

[Oxygen-Absorbing Layer (Layer A)]

The oxygen-absorbing layer (layer A) of the oxygen-absorbing multilayer body of the embodiment is formed of an oxygen-absorbing resin composition containing at least one tetralin ring-containing polyamide compound having at least one selected from the group consisting of the constituent units represented by the above general formulas (1) and (2) and a transition metal catalyst. The oxygen-absorbing resin composition used herein is the same as described in the first embodiment.

The content rate of the tetralin ring-containing polyamide compound in layer A, which is not particularly limited, is preferably 50 mass % or more based on the total amount of layer A, more preferably 70 mass % or more and further preferably 90 mass % or more. If the content rate of a tetralin ring-containing polyamide compound is the preferable value or more, the oxygen-absorbing performance can be more enhanced, compared to the case where the content rate does not satisfy the above value.

In the oxygen-absorbing multilayer body of the embodiment, the thickness of the oxygen-absorbing layer (layer A), which can be appropriately specified depending upon use and desired performance, is not particularly limited. The thickness is preferably 5 to 200 μm and more preferably 10 to 100 μm. If the thickness falls within the preferable range mentioned above, the performance of layer A to absorb oxygen can be more enhanced; at the same time, the processability and economic aspect can be maintained at high levels, compared to the case where the thickness does not fall the above range. The thickness of the sealant layer (layer C), which can be also appropriately specified depending upon use and desired performance, is not particularly limited. The thickness is preferably 5 to 200 μm and more preferably 10 to 80 μm. If thickness falls within the preferable range mentioned above, the oxygen-absorbing rate of layer A can be more enhanced; at the same time, the processability and economic aspect can be maintained at high levels, compared to the case where the thickness does not fall within the above range. In consideration of processability of the resultant oxygen-absorbing multilayer body, the thickness ratio of layer C and layer A is preferably 1:0.5 to 1:3 and more preferably 1:1.5 to 1:2.5.

[Gas Barrier Layer (Layer D)]

The gas barrier layer (layer D) of the oxygen-absorbing multilayer body of the embodiment contains a gas barrier substance. The oxygen transmission rate of layer D measured in the case of a film having a thickness of 20 μm at 23° C. under the conditions of a relative humidity of 60% is preferably 100 mL/($m^2$·day·atm) or less, more preferably 80 mL/($m^2$·day·atm) or less and further preferably 50 mL/($m^2$·day·atm) or less.

As the gas barrier substance to be used in layer D of the oxygen-absorbing multilayer body of the embodiment, a gas barrier thermoplastic resin, a gas barrier thermosetting resin, a silica, alumina, aluminum, etc. (used in the form of a vapor deposition film) and a metal such as aluminum (used in the form of foil) can be used. Examples of the gas barrier thermoplastic resin include an ethylene-vinyl alcohol copolymer, MXD6 and a poly(vinylidene chloride). Examples of the gas barrier thermosetting resin include gas barrier epoxy resin such as "MAXIVE" manufactured by Mitsubishi Gas Chemical Company, Inc.

When a thermoplastic resin is used as a gas barrier substance, the thickness of the gas barrier layer (layer D) is preferably 5 to 200 μm and more preferably 10 to 100 μm. When a thermosetting resin such as an amine-epoxy hardening agent is used as a gas barrier substance or in a gas barrier adhesive layer, the thickness of layer D is preferably 0.1 to 100 μm and more preferably 0.5 to 20 μm. If the thickness falls within the preferable range mentioned above, the gas barrier property tends to be more enhanced; at the same time, the processability and economic aspect can be maintained at high levels, compared to the case where the thickness does not fall within the aforementioned range.

Note that the oxygen-absorbing multilayer body of the embodiment may have one or more other layers such as a resin layer, a metal foil layer or an adhesive layer between layer C and layer A, between layer A and layer D or as an outer layer of layer C or as an outer layer of layer D. For example, to prevent breakage of layer D and formation of a pin hole, a protecting layer formed of a thermoplastic resin can be provided inside or outside layer D. Examples of the resin to be used in the protecting layer include polyethylenes such as a high-density polyethylene; polypropylenes such as a propylene homo polymer, a propylene-ethylene random copolymer and a propylene-ethylene block copolymer; polyamides such as nylon 6 and nylon 6,6; polyesters such as PET; and combinations of these.

In consideration of processability, the oxygen-absorbing multilayer body of the embodiment preferably has an intermediate layer formed of a polyolefin resin interposed between layer D and layer A. The thickness of the intermediate layer is preferably substantially the same as the thickness of layer C in view of processability. Note that herein, in consideration of variation by processing, if a thickness ratio of the layers falls within±10%, the thicknesses of the layers are regarded as being substantially same.

The oxygen-absorbing multilayer body of the embodiment can be manufactured by using a known method such as a coextrusion method, a laminating method and a coating method, which varies depending upon e.g., the properties of the material, processing purpose and processing step. The manufacturing method is not particularly limited. For example, a general method for laminating packaging materials such as a wet lamination process, a dry lamination process, a dry lamination process in the absence of a solvent, an extrusion lamination process, a T die coextrusion molding method, a coextrusion lamination process and an inflation process can be applied. For example, for molding a film or a sheet, a method of extruding a molten resin composition from an extruder provided with a T die, a circular die, etc., and a method of applying an adhesive to an oxygen-absorbing film or sheet separately formed and attaching it to another film or sheet are known. If necessary, for example, a pretreatment such as a corona treatment and an ozone treatment can be applied to a film etc. Furthermore, a known anchor coating agent, an adhesive, etc. can also be used. Examples of the anchor coating agent include isocyanate (urethane), polyethylene imine, polybutadiene and organic titanium. Examples of the adhesive include polyurethane, polyacrylate, polyester, epoxy, poly(vinyl acetate), cellulose and other adhesives for lamination.

Usage of the oxygen-absorbing multilayer body of the embodiment and the shape thereof are not particularly limited and can be appropriately specified depending upon the article to be contained and stored. For example, the multilayer body is manufactured as a film, which is further processed into a bag-form and a cover material and then put in use. Alternatively, a paper base material is laminated as an outer layer of layer D and the resultant laminate can be used as an oxygen-absorbing paper base material or as an oxygen-absorbing paper container. In view of maintaining processability in manufacturing a paper container by laminating with a paper base material at a high level, the total thickness of the layers present inside layer D is preferably 100 µm or less and more preferably 80 µm or less.

[Oxygen-Absorbing Multilayer Container]

The oxygen-absorbing multilayer container of the embodiment is a packaging container which has an oxygen-absorbing multilayer body as mentioned above in whole or in part thereof. The oxygen-absorbing multilayer container of the embodiment can absorb oxygen within the container (even if the amount of oxygen coming into the container from the outside is small, the incoming oxygen is also absorbed) to prevent e.g., deterioration due to oxygen of the content (the article to be packed) stored therein.

Usage of the oxygen-absorbing multilayer container of the embodiment and the shape thereof are not particularly limited and can be appropriately specified depending upon the article to be contained and stored. For example, a film-form or sheet-form oxygen-absorbing multilayer body as mentioned above can be formed into a bag such as a three-side sealed flat bag, a standing pouch, a gusset packaging bag, a pillow packaging bag, a multi-chamber pouch, which contains a main chamber and a sub chamber with an easy-to-peel wall between the main chamber and the sub chamber, and a shrink film package; and can be also formed into a container having an arbitrary shape by thermoforming.

More specifically, a film-form or sheet-form oxygen-absorbing multilayer body as mentioned above is subjected to molding such as vacuum molding, air-pressure forming and plug assist molding, if necessary, while applying heat to manufacture an oxygen-absorbing multilayer container having a predetermined shape such as a tray, a cup, a bottle, a tube and PTP (press-through pack). Furthermore, if molten resins are simultaneously injected or sequentially injected through multi-layered multiple dies into an injection mold by use of an injector, a multilayer container having a predetermined shape can be formed at a time. Moreover, the oxygen-absorbing multilayer body and container of the embodiment, if an open hole for releasing vapor during microwave cooking is provided, can be preferably used as a pouch for microwave cooking provided with a hole for easily releasing water vapor during microwave cooking.

Note that when a container having a flange portion is manufactured by thermoforming, a special process for imparting an easy-peeling function may be applied to the flange portion. If an oxygen-absorbing multilayer body as mentioned above is used as a material for a cover of a container, top seal, etc., an oxygen-absorbing function can be imparted to these containers.

(Third Embodiment)

Now, the third embodiment of the present invention will be described below. Note that repetition of explanation with respect to the same content as in the first and second embodiments is avoided herein.

[Oxygen-Absorbing Multilayer Injection-Molded Article]

The oxygen-absorbing multilayer injection-molded article of the embodiment at least has an oxygen-absorbing layer (layer A) formed of an oxygen-absorbing resin composition and a resin layer (layer B) containing a thermoplastic resin.

By using the oxygen-absorbing multilayer injection-molded article of the embodiment as a part of the structure of a sealing container, oxygen within the container can be absorbed (even if the amount of oxygen transmitting or coming into the container from the outside through the wall of the container is small, transmitting or incoming oxygen is also absorbed) to prevent e.g., deterioration due to oxygen of the content (the article to be packed) stored. At this time, the multilayer injection-molded article of the embodiment itself may be molded in the shape of the container. In consideration that the oxygen-absorbing multilayer injection-molded article of the embodiment delivers oxygen-absorbing performance, the molded article is preferably a preservation container such as a cup container (injection cup) and a bottle container.

In the oxygen-absorbing multilayer injection-molded article of the embodiment, the layer constitution is not particularly limited and the numbers and types of oxygen-absorbing layers (layer A) and resin layers (layer B) are not particularly limited. For example, an A/B, constitution, which is formed of one layer A and one layer B and a three-layer (B/A/B) constitution, which is formed of one layer A and two layers B, are acceptable. A five-layer (B1/B2/A/B2/B1) constitution, which is formed of one layer A and two layers B1 and two layers B2 is acceptable. The multilayer injection-molded article of the embodiment may have an optional layer such as an adhesion layer (layer AD), if necessary, and may be constituted of a seven-layers (e.g., B1/AD/B2/A/B2/AD/B1).

[Oxygen-Absorbing Layer (Layer A)]

In the oxygen-absorbing multilayer injection-molded article of the embodiment, the oxygen-absorbing layer (layer A) is formed of an oxygen-absorbing resin composition containing at least one tetralin ring-containing polyamide compound selected from the group consisting of the constituent units represented by the above general formulas (1) and (2) and a transition metal catalyst.

In the oxygen-absorbing multilayer injection-molded article of the embodiment, the thickness of the oxygen-absorbing layer (layer A), which can be appropriately specified depending upon the use and desired performance and is not particularly limited, is preferably 1 to 1000 μm, more preferably 2 to 800 μm and further preferably 5 to 700 μm. If the thickness falls within the preferable range mentioned above, the performance of layer A to absorb oxygen can be more enhanced and processability and economic aspect can be maintained at high levels, compared to the case where the thickness does not satisfy the above condition.

[Resin Layer (Layer B) Containing Thermoplastic Resin]

In the oxygen-absorbing multilayer injection-molded article of the embodiment, the resin layer (layer B) is a layer containing a thermoplastic resin. The content rate of the thermoplastic resin in layer B, which can be appropriately specified, is not particularly limited; however, the content rate is preferably 70 to 100 mass % based on the total amount of layer B, more preferably 80 to 100 mass % and further preferably 90 to 100 mass %.

The oxygen-absorbing multilayer injection-molded article of the embodiment may have a plurality of layers B. The constitution of the plural layers B may be the same or different. In the oxygen-absorbing multilayer injection-molded article of the embodiment, the thickness of layer B, which can be appropriately determined depending upon the use, is not particularly limited. In view of ensuring physical properties required for a multilayer injection-molded article such as strength including drop resistance and flexibility, the thickness is preferably 5 to 1000 μm, more preferably 10 to 800 μm and further preferably 20 to 500 μm.

As the thermoplastic resin to be used in layer B of the oxygen-absorbing multilayer injection-molded article of the embodiment, any thermoplastic resin can be used, in other words, the thermoplastic resin of layer B is not particularly limited. In particular, layer B of the embodiment preferably contains at least one type of thermoplastic resin selected from the group consisting of a polyolefin, a polyester, a polyamide, an ethylene-vinyl alcohol copolymer, a plant-derived resin and a chlorine resin. The thermoplastic resin to be used in layer B of the embodiment preferably contains a thermoplastic resin other than a tetralin ring-containing polyamide compound in an amount of 50 to 100 mass % based on the total amount of thermoplastic resins, more preferably 70 to 100 mass % and further preferably 90 to 100 mass %.

Now, examples of the thermoplastic resin preferably used in layer B of the oxygen-absorbing multilayer injection-molded article of the embodiment will be mentioned below.

<Polyolefin>

Specific examples of the polyolefin to be used in layer B of the oxygen-absorbing multilayer injection-molded article of the embodiment include polyethylenes such as a low-density polyethylene, a medium-density polyethylene, a high-density polyethylene, a linear and low-density polyethylene, and a linear and extremely low-density polyethylene; olefin homopolymers such as a polypropylene, polybutene-1 and poly-4-methylpentene-1; ethylene and α-olefin copolymers such as an ethylene-propylene random copolymer, an ethylene-propylene block copolymer, an ethylene-propylene-polybutene-1 copolymer and an ethylene-cyclic olefin copolymer; other ethylene copolymers such as an ethylene-α, β-unsaturated carboxylic acid copolymer such as ethylene-(meth)acrylate copolymer, an ethylene-α, β-unsaturated carboxylic acid ester copolymer such as an ethylene-ethyl(meth)acrylate copolymer, ion crosslinked compound of ethylene-α, β-unsaturated carboxylic acid copolymer and an ethylene-vinyl acetate copolymer; open-ring polymers of a cyclic olefin and hydrogenated compounds thereof; cyclic olefin-ethylene copolymers; and graft-modified polyolefins obtained by modifying these polyolefins with an acid anhydride such as maleic anhydride.

<Polyester>

As specific examples of the polyester to be used in layer B of the oxygen-absorbing multilayer injection-molded article of the embodiment, those formed of one or two or more compounds selected from polyvalent carboxylic acids containing a dicarboxylic acid and ester-forming derivatives of these and one or two or more compounds selected from polyhydric alcohols including a glycol; those formed of hydroxy carboxylic acids and ester-forming derivative of these; and those formed of cyclic esters are mentioned. Ethylene terephthalate thermoplastic polyester is preferably a polyester in which a most part of ester repeat units, generally 70 mole % or more thereof, is occupied by an ethylene terephthalate unit and having a glass transition point (Tg) within the range of 50 to 90° C. and a melting point (Tm) within the range of 200 to 275° C. As an ethylene terephthalate thermoplastic polyester, a polyethylene terephthalate is particularly excellent in pressure resistance, heat resistance, thermal pressure resistance, etc. However, a polyester copolymer containing small amounts of ethylene terephthalate unit and an ester unit formed of a dicarboxylic acid such as isophthalic acid and naphthalene dicarboxylic acid and a diol such as propylene glycol, can also be used.

Specific examples of the dicarboxylic acid include saturated aliphatic dicarboxylic acids such as oxalic acid, malonic acid, succinic acid, glutaric acid, adipic acid, pimelic acid, suberic acid, azelaic acid, sebacic acid, decanedicarboxylic acid, dodecanedicarboxylic acid, tetradecanedicarboxylic acid, hexadecanedicarboxylic acid, 3-cyclobutanedicarboxylic acid, 1,3-cyclopentanedicarboxylic acid, 1,2-cyclohexanedicarboxylic acid, 1,3-cyclohexanedicarboxylic acid, 1,4-cyclohexanedicarboxylic acid, 2,5-norbornanedicarboxylic acid and dimer acid or ester-forming derivatives of these; unsaturated aliphatic dicarboxylic acids such as fumaric acid, maleic acid and itaconic acid or ester-forming derivatives of these; naphthalenedicarboxylic acids such as orthophthalic acid, isophthalic acid, terephthalic acid, 1,3-naphthalenedicarboxylic acid, 1,4-naphthalenedicarboxylic acid, 1,5-naphthalenedicarboxylic acid, 2,6-naphthalenedicarboxylic acid and 2,7-naphthalenedicarboxylic acid; aromatic dicarboxylic acids such as 4,4'-biphenyldicarboxylic acid, 4,4'-biphenylsulfonedicarboxylic acid, 4,4'-biphenyletherdicarboxylic acid, 1,2-bis(phenoxy)ethane-p,p'-dicarboxylic acid and anthracenedicarboxylic acid or ester-forming derivatives of these; and metal sulfonate group-containing aromatic dicarboxylic acids such as 5-sodium sulfo-isophthalic acid, 2-sodium sulfo-terephthalic acid, 5-lithium sulfo-isophthalic acid, 2-lithium sulfo-terephthalic acid, 5-potassium sulfo-isophthalic acid and 2-potassium sulfo-terephthalic acid or lower alkyl ester derivatives of these.

Of the aforementioned dicarboxylic acids, particularly, terephthalic acid, isophthalic acid and naphthalene dicarboxylic acid are preferably used in view of the physical properties etc. of the polyesters to be obtained. Note that, if necessary, other dicarboxylic acids may be copolymerized.

Specific examples of the polyvalent carboxylic acids other than these dicarboxylic acids include ethane tricarboxylic acid, propane tricarboxylic acid, butane tetracarboxylic acid, pyromellitic acid, trimellitic acid, trimesic acid, 3,4,3',4'-biphenyltetracarboxylic acid and ester-forming derivatives of these.

Specific examples of the glycol include aliphatic glycols such as ethylene glycol, 1,2-propylene glycol, 1,3-propylene glycol, diethylene glycol, triethylene glycol, 1,2-butylene glycol, 1,3-butylene glycol, 2,3-butylene glycol, 1,4-butylene glycol, 1,5-pentanediol, neopentyl glycol, 1,6-hexanediol, 1,2-cyclohexanediol, 1,3-cyclohexanediol, 1,4-cyclohexanediol, 1,2-cyclohexane dimethanol, 1,3-cyclohexane dimethanol, 1,4-cyclohexane dimethanol, 1,4-cyclohexane diethanol, 1,10-dacamethylene glycol, 1,12-dodecane diol, polyethylene glycol, poly(trimethylene glycol) and poly (tetramethylene glycol); and aromatic glycols such as hydroquinone, 4,4'-dihydrox bisphenol, 1,4-bis(β-hydroxyethoxy)benzene, 1,4-bis(β-hydroxyethoxyphenyl)sulfone, bis(p-hydroxyphenyl)ether, bis(p-hydroxyphenyl)sulfone, bis(p-hydroxyphenyl)methane, 1,2-bis(p-hydroxyphenyl)ethane, bisphenol A, bisphenol C, 2,5-naphthalene diol and glycols formed by adding an ethylene oxide to these glycols.

Of the glycols mentioned above, particularly, ethylene glycol, 1,3-propylene glycol, 1,4-butylene glycol, and 1,4-cyclohexane dimethanol are preferably used as a main component.

Specific examples of the polyhydric alcohols other than these glycols include trimethylol methane, trimethylol ethane, trimethylol propane, pentaerythritol, glycerol and hexane triol.

Specific examples of the hydroxy carboxylic acid include, lactic acid, citric acid, malic acid, tartaric acid, hydroxyacetic acid, 3-hydroxybutyrate, p-hydroxybenzoate, p-(2-hydroxyethoxyl)benzoate, 4-hydroxycyclohexanecarboxylic acid and ester-forming derivatives of these.

Specific examples of the cyclic esters include ε-caprolactone, β-propiolactone, β-methyl-β-propiolactone, δ-valerolactone, glycolide and lactide.

Specific examples of the ester-forming derivatives of a polyvalent carboxylic acid and a hydroxy carboxylic acid include alkyl esters, acid chlorides and acid anhydrides of these.

Of the aforementioned ones, a polyester containing terephthalic acid or an ester-forming derivative thereof, or a naphthalene dicarboxylic acid or an ester-forming derivative thereof as a main acid component and an alkylene glycol as a main glycol component is preferable.

Note that the polyester containing terephthalic acid or an ester-forming derivative thereof as a main acid component is a polyester preferably containing the terephthalic acids or ester-forming derivatives thereof in total in an amount of 70 mole % or more based on the total amount (mole) of the acid components, more preferably in an amount of 80 mole % or more and further preferably in an amount of 90 mole % or more. Similarly, the polyester containing naphthalene dicarboxylic acids or ester-forming derivatives thereof as a main acid component is a polyester preferably containing the naphthalene dicarboxylic acids or ester-forming derivatives thereof in total in an amount of 70 mole % or more, more preferably in an amount of 80 mole % or more and further preferably in an amount of 90 mole % or more.

Of the aforementioned naphthalene dicarboxylic acids or ester-forming derivatives of these, dicarboxylic acids exemplified above such as 1,3-naphthalene dicarboxylic acid, 1,4-naphthalene dicarboxylic acid, 1,5-naphthalene dicarboxylic acid, 2,6-naphthalene dicarboxylic acid and 2,7-naphthalene dicarboxylic acid or ester-forming derivatives of these are preferable.

The aforementioned polyester, in which the main glycol component is an alkylene glycol, is a polyester containing alkylene glycols in total preferably in an amount of 70 mole % or more based on the total of the glycol components, more preferably in an amount of 80 mole % or more and further preferably in an amount of 90 mole % or more. Note that the alkylene glycols herein may contain a substituent and an alicyclic structure in the molecular chain.

A copolymerization component other than the aforementioned terephthalic acid/ethylene glycol, in view of attaining transparency and moldability at the same time, is preferably at least one selected from the group consisting of isophthalic acid, 2,6-naphthalene dicarboxylic acid, diethylene glycol, neopentyl glycol, 1,4-cyclohexanedimethanol, 1,2-propanediol, 1,3-propanediol and 2-methyl-1,3-propanediol, and more preferably at least one selected from the group consisting of isophthalic acid, diethylene glycol, neopentyl glycol and 1,4-cyclohexane dimethanol.

A preferable example of the polyester to be used in layer B of the oxygen-absorbing multilayer injection-molded article of the embodiment is a polyester having a main repeat unit constituted of ethylene terephthalate, more preferably a linear polyester containing an ethylene terephthalate unit in an amount of 70 mole % or more, further preferably a linear polyester containing an ethylene terephthalate unit in an amount of 80 mole % or more and particularly preferably a linear polyester containing an ethylene terephthalate unit in an amount of 90 mole % or more.

Another preferable example of the polyester to be used in layer B of the oxygen-absorbing multilayer injection-molded article of the embodiment is a polyester having a main repeat unit constituted of ethylene-2,6-naphthalate, more preferably a linear polyester containing ethylene-2,6-naphthalate unit in an amount of 70 mole % or more, further preferably a linear polyester containing ethylene-2,6-naphthalate unit in an amount of 80 mole % or more and particularly preferably a linear polyester containing ethylene-2,6-naphthalate unit in an amount of 90 mole % or more.

Another preferable example of the polyester to be used in layer B of the oxygen-absorbing multilayer injection-molded article of the embodiment is a linear polyester containing a propylene terephthalate unit in an amount of 70 mole % or more, a linear polyester containing a propylene naphthalate unit in an amount of 70 mole % or more, a linear polyester containing a 1,4-cyclohexanedimethylene terephthalate unit in an amount of 70 mole % or more, a linear polyester containing a butylene naphthalate unit in an amount of 70 mole % or more or a linear polyester containing a butylene terephthalate unit in an amount of 70 mole % or more.

In view of attaining transparency and moldability at the same time, a particularly preferable polyester, in other words, a particularly preferable combination of components constituting a total polyester, includes a combination of terephthalic acid/isophthalic acid/ethylene glycol, a combination of terephthalic acid/ethylene glycol/1,4-cyclohexane dimethanol and a combination of terephthalic acid/ethylene glycol/neopentyl glycol. Note that, needless to say, the polyesters mentioned above may inevitably contain diethylene glycol, which is produced by dimerization of ethylene glycols during an esterification (transesterification) reaction and a polycondensation reaction, in a small amount (5 mole % or less).

Another preferable example of the polyester to be used in layer B of the oxygen-absorbing multilayer injection-molded article of the embodiment is poly(glycolic acid), which is obtained through polycondensation of a glycolic acid and methyl glycolate or ring-opening polycondensation of glycolide. Note that the poly(glycolic acid) may be copolymerized with another component such as lactide.

<Polyamide>

The polyamide that will be described below is a polyamide exemplified as the thermoplastic resin of layer B and does not contain a tetralin ring-containing polyamide compound of the embodiment. Specific examples of the polyamide to be used in layer B of the oxygen-absorbing multilayer injection-molded article of the embodiment include polyamides containing a unit derived from a lactam or an aminocarboxylic acid as a main constituent unit; aliphatic polyamides containing a unit derived from an aliphatic diamine and an aliphatic dicarboxylic acid as a main constituent unit; partially aromatic polyamides containing a unit derived from an aliphatic diamine and an aromatic dicarboxylic acid as a main constituent unit; and partially aromatic polyamides containing a unit derived from an aromatic diamine and an aliphatic dicarboxylic acid as a main constituent unit. Note that the polyamides herein may be, if necessary, copolymerized with a monomer unit other than a main constituent unit.

Specific examples of the lactam or aminocarboxylic acid include lactams such as ε-caprolactam and laurolactam; aminocarboxylic acids such as aminocaproic acid and aminoundecanoic acid; and aromatic aminocarboxylic acids such as para-aminomethylbenzoic acid.

Specific examples of the aliphatic diamine include aliphatic diamines having 2 to 12 carbon atoms or functional derivatives thereof and alicyclic diamines. Note that the aliphatic diamines may be linear aliphatic diamines or branched aliphatic diamines. Specific examples of the linear aliphatic diamines include aliphatic diamines such as ethylenediamine, 1-methylethylenediamine, 1,3-propylenediamine, tetramethylenediamine, pentamethylenediamine, hexamethylenediamine, heptamethylenediamine, octamethylenediamine, nonamethylenediamine, dacamethylenediamine, undecamethylenediamine and dodecamethylenediamine. Specific examples of the alicyclic diamines include cyclohexanediamine, 1,3-bis(aminomethyl)cyclohexane and 1,4-bis(aminomethyl)cyclohexane.

Specific examples of the aliphatic dicarboxylic acid include linear aliphatic dicarboxylic acids and alicyclic dicarboxylic acids. In particular, linear aliphatic dicarboxylic acids having an alkylene group of 4 to 12 carbon atoms are preferable. Examples of the linear aliphatic dicarboxylic acids include adipic acid, sebacic acid, pimelic acid, suberic acid, azelaic acid, undecanoic acid, undecadioic acid, dodecanedioic acid, dimeric acid and functional derivatives of these. Examples of the alicyclic dicarboxylic acids include 1,4-cyclohexane dicarboxylic acid, hexahydroterephthalic acid and hexahydroisophthalic acid.

Specific examples of the aromatic diamines include metaxylylenediamine, paraxylylenediamine and para-bis(2-aminoethyl)benzene.

Specific examples of the aromatic dicarboxylic acids include terephthalic acid, isophthalic acid, phthalic acid, 2,6-naphthalene dicarboxylic acid, diphenyl-4,4'-dicarboxylic acid, diphenoxyethane dicarboxylic acid and functional derivatives thereof.

Specific examples of the polyamide include polyamide 4, polyamide 6, polyamide 10, polyamide 11, polyamide 12, polyamide 4,6, polyamide 6,6, polyamide 6,10, polyamide 6T, polyamide 9T, polyamide 6IT, poly(metaxylylene adipamide) (polyamide MXD6), isophthalic acid copolymerized poly(metaxylylene adipamide) (polyamide MXD6I), poly(metaxylylene sebacamide) (polyamide MXD10), poly(metaxylylene dodecanamide) (polyamide MXD12), poly(1,3-bisaminocyclohexane adipamide) (polyamide BAC6) and poly(paraxylylene sebacamide) (polyamide PXD10). As more preferable polyamide, polyamide 6, polyamide MXD6 and polyamide MXD6I are mentioned.

As a component to be copolymerized with the polyamide, a polyether having at least one terminal amino group or terminal carboxyl group, and having a number average molecular weight of 2000 to 20000, an organic carboxylic acid salt of a polyether having at least one terminal amino group or an amino salt of a polyether having at least one terminal carboxyl group, can be used. Specific examples thereof include bis(aminopropyl)poly(ethylene oxide) (polyethylene glycol having a number average molecular weight of 2000 to 20000).

The partially aromatic polyamides may contain a constituent unit derived from a polyvalent carboxylic acid having 3 bases or more, such as trimellitic acid and pyromellitic acid, as long as they maintain a substantially linear chain.

<Ethylene-Vinyl Alcohol Copolymer>

As the ethylene vinyl alcohol copolymer to be used in layer B of the oxygen-absorbing multilayer injection-molded article of the embodiment, an ethylene vinyl alcohol copolymer, which contains an ethylene in an amount of 15 to 60 mole % and has a saponification degree of a vinyl acetate component of 90 mole % or more, is preferable. The content of ethylene is preferably 20 to 55 mole % and more preferably 29 to 44 mole %. The saponification degree of the vinyl acetate component is preferably 95 mole % or more. Note that the ethylene vinyl alcohol copolymer may further contain a small amount of comonomer of propylene, isobutene, an α-olefin such as α-octene, α-dodecene and α-octadecene, an unsaturated carboxylic acid or a salt thereof, a partial alkyl ester, a complete alkyl ester, a nitrile, an amide, an anhydride, and an unsaturated sulfonic acid or a salt thereof, etc.

<Vegetable-Derived Resin>

As the vegetable-derived resin to be used in layer B of the oxygen-absorbing multilayer injection-molded article of the embodiment, any vegetable-derived resin can be used as long as it is a resin containing a vegetable-derived substance as a raw material. The vegetable serving as a raw material thereof is not particularly limited. Specific examples of the vegetable-derived resin include aliphatic polyester based biodegradable resins. Furthermore, examples of the aliphatic polyester based biodegradable resins include poly(α-hydroxy acid) such as poly(glycolic acid) (PGA) and polylactic acid (PLA); and polyalkylene alkanoate such as polybutylenesuccinate (PBS) and polyethylenesuccinate (PES).

<Chlorine Resin>

The chlorine resin to be used in layer B of the oxygen-absorbing multilayer injection-molded article of the embodiment is not limited as long as it is a resin containing chlorine in a constituent unit and a known resin can be used. Specific examples of the chlorine resin include poly(vinyl chloride), poly(vinylidene chloride) and copolymers of these with vinyl acetate, a maleic acid derivative, a higher alkyl vinyl ether, and the like.

Layer B of the oxygen-absorbing multilayer injection-molded article of the embodiment may contain various types of additives known in the art other than a thermoplastic resin as mentioned above. Examples of such optional components include, but not particularly limited to, additives such as a drying agent, a pigment such as titanium oxide, a dye, an antioxidant, a slipping agent, an antistatic agent, a plasticizer, a stabilizer, a lubricant; fillers such as calcium carbonate, clay, mica and silica; and a deodorant. Particularly, in view of recycling and reprocessing offcuts generated during manufacturing, it is preferable to add an antioxidant to layer B.

The oxygen-absorbing multilayer injection-molded article of the embodiment may have an optional layer, which varies depending upon desired performance etc. other than the aforementioned oxygen-absorbing layer (layer A) and resin layer (layer B). Examples of such an optional layer include an adhesion layer.

For example, in view of more enhancing interlayer adhesion strength between adjacent two layers, an adhesion layer (layer AD) is preferably provided between the two layers. The adhesion layer preferably contains a thermoplastic resin having adhesiveness. Examples of the thermoplastic resin having adhesiveness include acid modified polyolefin resins obtained by modifying a polyolefin resin such as a polyethylene or a polypropylene with an unsaturated carboxylic acid such as acrylic acid, methacrylic acid, maleic acid, maleic anhydride, fumaric acid and itaconic acid; and polyester thermoplastic elastomers containing a polyester block copolymer as a main component. In view of enhancing adhesiveness with the aforementioned resin layer (layer B), a resin obtained by modifying the same type of resin as the thermoplastic resin used in layer B is preferable. Note that the thickness of the adhesion layer is not particularly limited; however, in view of ensuring molding processability while exerting substantial adhesion strength, the thickness of the adhesion layer is preferably 2 to 100 μm, more preferably 5 to 90 μm and further preferably 10 to 80 μm.

As a method for manufacturing the oxygen-absorbing multilayer injection-molded article of the embodiment, a known method, which varies depending upon the properties of materials, a desired shape, etc., can be applied. Thus, the manufacturing method is not particularly limited. Various types of injection molding methods can be used for manufacturing the multilayer injection-molded article. For example, using a molding machine having 2 or more injectors and an injection mold, a material for constituting layer A and a material for constituting layer B are injected from respective injection cylinders through a mold hot runner into a cavity. In this manner, a multilayer injection-molded article of a two-layer (A/B) structure having a shape in accordance with the cavity shape of the injection mold can be manufactured. Furthermore, first, a material for constituting layer B is injected from the injection cylinder, and then, a material for constituting layer A is injected from another injection cylinder simultaneously with a resin for constituting layer B, subsequently, the resin for constituting layer B is injected in a necessary amount to fill the cavity to manufacture a multilayer injection-molded article constituted of three layers (B/A/B). Furthermore, first, a material for constituting layer B is injected, then a material for constituting layer A is solely injected, and finally the material for constituting layer B is injected in a necessary amount to fill the cavity to manufacture a multilayer injection-molded article constituted of five layers (B/A/B/A/B). Moreover, first, a material for constituting layer B1 is injected from an injection cylinder and then a material for constituting layer B2 is injected from another injection cylinder simultaneously with a resin for constituting layer B1, subsequently a resin for constituting layer A is injected simultaneously with resins for constituting layer B1 and layer B2 and thereafter the resin for constituting layer B1 is injected in a necessary amount to fill the cavity to manufacture a multilayer injection-molded article constituted of five layers (B1/B2/A/B2/B1). To add heat resistance to the neck portion of the obtained molded article, a heat treatment may be applied to the neck portion in this stage to perform crystallization. In this case, the degree of crystallization, which may be appropriately specified depending upon the type of resin to be used and desired performance, is not particularly limited. Generally, the degree of crystallization is preferably about 30 to 50% and more preferably 35 to 45%. Note that the crystallization of the neck portion of a molded article may be performed after a secondary processing (described later) is applied.

The shape of the oxygen-absorbing multilayer injection-molded article of the embodiment may be appropriately specified depending upon the use and is not particularly limited. When injection molding using a mold is performed as described above, any shape can be obtained corresponding to the shape of cavity of the mold.

The thickness of the oxygen-absorbing multilayer injection-molded article of the embodiment is not particularly limited. In view of enhancing oxygen-absorbing performance; at the same time, ensuring physical properties such as flexibility, required for a multilayer injection-molded article, the thickness is preferably 3 to 5000 μm, more preferably, 5 to 4500 μm and further preferably 10 to 4000 μm.

By using the oxygen-absorbing multilayer injection-molded article of the embodiment as a part of the structure of a sealing container, oxygen within the container can be absorbed (even if the amount of oxygen transmitting or coming into the container from the outside through the wall of the container is small, transmitting or incoming oxygen is also absorbed) to prevent deterioration etc. of the content (the article to be packed) to be stored by oxygen. At this time, the injection-molded article of the embodiment itself may be molded in the shape of the container. In consideration that the oxygen-absorbing multilayer injection-molded article of the embodiment delivers oxygen-absorbing performance, the molded article is preferably a preservation container such as a cup container (injection cup) and a bottle container.

The multilayer injection-molded article of the embodiment can be molded into a container by applying a secondary processing (described later). For example, when a secondary processing is applied to form a PET bottle, the multilayer injection-molded article of the embodiment is preferably a test tube preform (parison). The container obtained by a secondary processing of the oxygen-absorbing multilayer injection-molded article of the embodiment can also absorb oxygen within the container (even if the amount of oxygen transmitting or coming into the container from the outside through the wall of the container is small, transmitting or incoming oxygen is also absorbed) to prevent deterioration etc. of the content (the article to be packed) stored therein by oxygen. Note that examples of the shape of a container after secondary processing include a bottle and a cup.

As a method for secondary processing the oxygen-absorbing multilayer injection-molded article of the embodiment, for example, blow-molding and stretch blow-molding are mentioned but not particularly limited to these and a known molding method can be applied.

For example, in the injection blow-molding, first, a preform (parison) in the form of a test tube is molded as the oxygen-absorbing multilayer injection-molded article of the embodiment. Then, the preform is heated and allowed to fit into a final-form mold with the mouth portion thereof immobilized by a jig. Thereafter, air is fed from the mouth portion to swollen the preform, with the result that the preform comes into contact with the mold. Then, the preform is cooled and solidified to mold a bottle.

For example, in the injection stretch blow-molding, first, a preform (parison) in the form of a test tube is molded as the oxygen-absorbing multilayer injection-molded article of the embodiment. Then, the preform is heated and allowed to fit into a final-form mold with the mouth portion thereof immobilized by a jig. Thereafter, air is fed from the mouth portion while stretching by a stretching rod to perform blow-drawing of the preform to allow the preform in contact with the mold. Then, the preform is cooled and solidified to mold a bottle.

The injection stretch blow-molding methods herein are in general roughly divided into a hot parison system and a cold parison system. In the former one, a preform is not completely cooled and a preform in a soft condition is blow-molded. In contrast, in the latter one, a preform with a bottom having a size considerably smaller than the size of a final shape and formed of an amorphous resin in a super cooling condition is formed, and the preform is pre-heated to a drawing temperature and molded in the axis direction by tensile stretching in a final-shape mold; at the same time, molded in the circumference direction by stretch blowing. Because of this, the latter one is suitable for large scale production. In either method, a preform is heated to a drawing temperature of a glass transition point (Tg) or more and thereafter stretched in the longitudinal direction by a stretching rod in a final-shape mold heated to a heat treatment (heat set) temperature; at the same time, stretched in the transverse direction by air blow. Herein, the draw ratio of final blow-molded article is not particularly limited; however, the draw ratio is preferably 1.2 to 6 times in the longitudinal direction and 1.2 to 4.5 times in the transverse direction.

Note that in the injection blow-molding, as a general technique, the final-shape mold is heated to a temperature at which crystallization of a resin is accelerated, for example, 120 to 230° C. and preferably 130 to 210° C. in the case of a PET resin. Thereafter, in the blowing step, a heat treatment is performed by bringing the outside wall of a molded article (container) into contact with the inner surface of the mold in a predetermined time. After the heat treatment is performed in a predetermined time, a fluid for blowing is changed to an internal cooling fluid to cool the inner layer. The heat treatment time at this time varies depending upon the thickness and temperature of a blow-molded article. The heat treatment time in the case of a PET resin, is generally 1.5 to 30 seconds and preferably 2 to 20 seconds. Whereas, the cooling time also varies depending upon the heat treatment temperature and the type of cooling fluid; however, the cooling time is generally 0.1 to 30 seconds and preferably 0.2 to 20 seconds. Owing to the heat treatment, each portions of the molded article is crystallized.

As the cooling fluid, air of normal temperature, cooled gases such as nitrogen, air, and carbon dioxide gas of −40° C. to +10° C. are used. Other than these, a chemically inactive liquefied gas such as liquefied nitrogen gas, liquefied carbonate gas, liquefied trichlorofluoromethane gas, liquefied dichlorodifluoromethane gas and other liquefied aliphatic hydrocarbon gases can be used. The cooling fluid may be used in combination with liquid mist requiring high heat of vaporization such as water. By using such a cooling fluid, significant cooling temperature can be provided. In stretch blow-molding, two molds are used. In the first mold, a heat treatment may be performed within a predetermined temperature and time and then the blow-molded article may be transferred to the second mold for cooling. The blow-molded article may be blow-molded again, simultaneously with being cooled. The outer layer of the blow-molded article taken out from the mold is allowed to stand still to cool it or cold air can be applied to cool the outer layer of the blow-molded article.

As another blow-molding method, a two-step blow-molding is exemplified, in which the aforementioned preform is processed into a primary blow-molded article, which is larger in size than a final blow-molded article, by use of a primary stretch-blow mold, and subsequently, the primary blow-molded article is heated to shrink, and then, processed into a final blow-molded article by stretch blow-molding using a secondary mold. According to the blow-molding method, the bottom of the blow-molded article is sufficiently stretched to reduce in thickness, with the result that a blow molded article with the bottom, which is rarely deformed during hot charging and heat sterilization and having excellent impact resistance can be obtained.

Note that the oxygen-absorbing multilayer injection-molded article of the embodiment and the multilayer container obtained by subjecting it to secondary processing may be coated with e.g., a vapor deposition film of an inorganic compound or an inorganic oxide or an amorphous carbon film.

Examples of the inorganic compound or inorganic oxide of the vapor deposition film include, but not particularly limited to, aluminum, alumina and silicon oxide. By virtue of the coating with a vapor deposition film of an inorganic compound or an inorganic oxide, it is possible to block elution of a low molecular weight organic compound from the multilayer injection-molded article of the embodiment and the container obtained by secondary processing of the article. Examples of the method for forming a vapor deposition film include a physical vapor deposition method such as a vacuum vapor deposition method, a sputtering method and an ion plating method, and chemical vapor deposition methods such as a plasma CVD method. However, the method for forming a vapor deposition film is not particularly limited to these and known methods can be applied. Note that the thickness of the vapor deposition film is not particularly limited; however, in view of gas barrier property, light-blocking property, flex resistance, etc., the thickness is preferably 5 to 500 nm and more preferable 5 to 200 nm.

An amorphous carbon film, which is known as a diamond carbon film, is a hard carbon film also called as an i carbon film or a hydrogenated amorphous carbon film. Examples of a method for forming such an amorphous carbon film include, but not particularly limited to, a method in which the interior portion of a hollow molded article is exhausted to a vacuum, and then a carbon source gas is supplied and energy for generating a plasma is supplied to convert the carbon source gas into a plasma. In this manner, an amorphous carbon film is formed on the inner surface of the container. Owing to the coating with an amorphous carbon film, the transmission rate of a low molecular weight inorganic gas such as oxygen and carbon dioxide can be significantly reduced as well as adsorption of low molecular weight organic compounds having odor to an oxygen-absorbing multilayer injection-molded article can be suppressed. Note that the thickness of such an amorphous carbon film is not particularly limited; however, in view of effect of suppressing adsorption of a low molecular weight organic compound, effect of improving a gas barrier property, adhesion property to a plastic, durability, transparency, etc., the thickness is preferably 50 to 5000 nm.

The multilayer injection-molded article of the embodiment can be preferably used for storing an article to be packed as explained in the first embodiment mentioned above. Note that before and after charging (packaging) of such an article to be packed, the container and the article to be packed can be sterilized by a method suitable for the article to be packed. Examples of the sterilization method include heat treatment such as a boiling treatment performed at 100° C. or less, a semi-retort treatment and a retort treat performed at 100° C. or more, and a high retort treatment performed at 130° C. or more; sterilization with an electromagnetic wave such as UV rays, microwave and gamma ray; gas treatment performed with ethylene oxide etc.; and sterilization with a chemical agent such as hydrogen peroxide and hypochlorite.

(Fourth Embodiment)

Now, the fourth embodiment of the present invention will be described below. Note that repetition of explanation with respect to the same content as in the first to third embodiments is avoided herein.

The oxygen-absorbing medical multilayer molded container of the embodiment has at least three layers, i.e., a first resin layer (layer B) at least containing a thermoplastic resin, an oxygen-absorbing layer (layer A) formed of an oxygen-absorbing resin composition, a second resin layer (layer B) at least containing a thermoplastic resin, in this order.

The oxygen-absorbing medical multilayer molded container of the embodiment can absorb oxygen within the container (even if the amount of oxygen transmitting or coming into the container from the outside through the wall of the container is small, transmitting or incoming oxygen is also absorbed) to prevent deterioration etc. of the content (the article to be packed) stored therein by oxygen.

The layer constitution of the oxygen-absorbing medical multilayer molded container of the embodiment is not particularly limited. More specifically, the numbers and types of oxygen-absorbing layers (layer A) and resin layers (layer B) are not particularly limited as long as these layers are arranged in the order of B/A/B. For example, a five-layer (B1/B2/A/B2/B1) structure, which is constituted of one layer A and two layers B1 and two layers B2, may be acceptable. Furthermore, the oxygen-absorbing medical multilayer molded container of the embodiment, may have an optional layer, if necessary, such as an adhesion layer (layer AD). For example, seven-layer (B1/AD/B2/A/B2/AD/B1) structure is acceptable.

[Oxygen-Absorbing Layer (Layer A)]

In the oxygen-absorbing medical multilayer molded container of the embodiment, the oxygen-absorbing layer (layer A) is formed of an oxygen-absorbing resin composition containing at least one tetralin ring-containing polyamide compound selected from the group consisting of the constituent units represented by the above general formulas (1) and (2) and a transition metal catalyst. The oxygen-absorbing resin composition is the same as that described in the first embodiment except the following matters particularly described. Furthermore, the oxygen-absorbing layer (layer A) is the same as that described in the second embodiment except the following matters particularly described.

In the oxygen-absorbing medical multilayer molded container of the embodiment, the thickness of the oxygen-absorbing layer (layer A), which can be appropriately specified depending upon use and desired performance, is not particularly limited. In view of having high oxygen-absorbing performance and ensuring physical properties required for a medical multilayer molded container, the thickness is preferably 1 to 1000 μm, more preferably 50 to 900 μm and further preferably 100 to 800 μm.

[Resin Layer (Layer B) Containing a Thermoplastic Resin]

In the oxygen-absorbing medical multilayer molded container of the embodiment, the resin layer (layer B) is a layer containing a thermoplastic resin. The content rate of the thermoplastic resin in layer B, which can be appropriately specified, is not particularly limited. The content rate is preferably 70 to 100 mass % based on the total amount of layer B, more preferably 80 to 100 mass % and further preferably 90 to 100 mass %.

The oxygen-absorbing medical multilayer molded container of the embodiment may have a plurality of layers B. The constitution of the plural layers B may be the same or different. The thickness of layer B, which can be appropriately determined depending upon the use, is not particularly limited. In view of ensuring physical properties required for a medical multilayer molded container, the thickness is preferably 50 to 10000 μm, more preferably 100 to 7000 μm and further preferably 300 to 5000 μm.

As thermoplastic resin to be used in layer B of the embodiment, any thermoplastic resin can be used and is not particularly limited. Specifically, thermoplastic resins described in the first embodiment are mentioned. In particular, the thermoplastic resin to be used in layer B of the embodiment is preferably at least one selected from the group consisting of a polyolefin, a polyester, a polyamide, an ethylene-vinyl alcohol copolymer, a vegetable-derived resin and a chlorine resin. Note that the thermoplastic resin to be used in layer B of the embodiment preferably contains a thermoplastic resin except the tetralin ring-containing polyamide compound according to the first embodiment in an amount of 50 to 100 mass %, more preferably 70 to 100 mass % and particularly preferably 90 to 100 mass %.

<Polyolefin>

Specific examples of the polyolefin to be used in layer B of the embodiment include, but not particularly limited to, polyethylenes (low-density polyethylene, medium-density polyethylene, high-density polyethylene, straight (linear) low-density polyethylene), polypropylenes, polybutene-1, poly-4-methylpentene-1, a copolymer between ethylene and an α-olefin, a copolymer between a propylene and an α-olefin, a copolymer between ethylene and an α,β-unsaturated carboxylic acid, and a copolymer between ethylene and an α,β-unsaturated carboxylic acid ester. As specific examples of these polyolefins, a ring opened polymer of a cycloolefin such as norbornene or tetracyclododecene or a derivatives thereof and a hydrogenated product thereof; and a copolymer (resin) having a cyclopentyl residue or a substituted cyclopentyl residue inserted in a molecular chain by polymerization between a cycloolefin such as norbornene or tetracyclododecene, or a derivative thereof and ethylene or propylene, are more preferable. Examples of the cycloolefin herein include monocyclic olefins and polycyclic olefins. Furthermore, a thermoplastic norbornene resin or a thermoplastic tetracyclododecene resin is one of more preferable resins. Examples of the thermoplastic norbornene resin include a ring opened polymer of a norbornene monomer and a hydrogenated product thereof; an addition polymer of a norbornene monomer; and an addition polymer of a norbornene monomer and an olefin. Examples of the thermoplastic tetracyclododecene resin include a ring opened polymer of a tetracyclododecene monomer and a hydrogenated product thereof; an addition polymer of a tetracyclododecene monomer; and an addition polymer of a tetracyclododecene monomer and an olefin. The thermoplastic norbornene resins are, for example, described in Japanese Patent Application Laid-Open No. 3-14882, Japanese Patent Application Laid-Open No. 3-122137, Japanese Patent Application Laid-Open No. 4-63807, etc.

Particularly preferable ones are a copolymer using norbornene and an olefin such as ethylene as raw materials and a cycloolefin copolymer (COC), which is a copolymer using tetracyclododecene and an olefin such as ethylene as raw materials. Furthermore, a cycloolefin polymer (COP), which is a polymer obtained by ring opening polymerization of a norbornene, followed by hydrogenating it, is particularly preferable. Such a COC and COP are, for example, described in Japanese Patent Application Laid-Open No. 5-300939 or Japanese Patent Application Laid-Open No. 5-317411.

COC is commercially available, for example, as APEL (registered trade mark) manufactured by Mitsui Chemicals Inc., whereas COP is commercially available, for example, as ZEONEX (registered trade mark) or ZEONOR (registered trade mark) manufactured by ZEON Corporation and as Daikyo Resin CZ (registered trade mark) manufactured by Daikyo Seko, Ltd. COC and COP exhibit chemical properties such as heat resistance and light resistance, chemical resistance (which are the feature derived from a polyolefin resin), and physical properties such as mechanical properties, fusion characteristics, flow properties and dimension accuracy (which are features derived from an amorphous resin). For this reason, COC and COP are most preferable.

<Polyester>

As specific examples of the polyester to be used in layer B of the embodiment, thermoplastic resins preferably used in layer B of the oxygen-absorbing multilayer injection-molded article in the third embodiment are mentioned.

In particular, as the polyester to be used in layer B of the embodiment, a polyester containing terephthalic acid or an ester-forming derivative thereof or a naphthalene dicarboxylic acid or an ester-forming derivative thereof as a main acid component and containing an alkylene glycol as a main glycol component, is preferable. Of the aforementioned dicarboxylic acids, particularly, use of terephthalic acid, isophthalic acid, 1,3-naphthalene dicarboxylic acid, 1,4-naphthalene dicarboxylic acid, 1,5-naphthalene dicarboxylic acid, 2,6-naphthalene dicarboxylic acid or 2,7-naphthalene dicarboxylic acid is preferable in view of physical properties etc. of the resultant polyester. Such polyester is preferably contained in an amount of 70 mole % or more. Of these dicarboxylic acids, particularly terephthalic acid and/or 2,6-naphthalene dicarboxylic acid are preferable. Furthermore, terephthalic acid and/or 2,6-naphthalene dicarboxylic acid are preferably contained in an amount of 70 mole % or more in view of physical properties etc., and more preferably in an amount of 90 mole % or more. If necessary, another dicarboxylic acid may be copolymerized. Furthermore, use of at least one copolymer component selected from the group consisting of isophthalic acid, diethylene glycol, neo-pentyl glycol, 1,4-cyclohexane dimethanol, 1,2-propanediol, 1,3-propanediol and 2-methyl-1,3-propanediol is preferable in view of obtaining transparency and moldability at the same time, particularly at least one selected from the group consisting of isophthalic acid, diethylene glycol, neopentyl glycol and 1,4-cyclohexanedimethanol is more preferable.

<Polyamide>

As specific examples of the polyamide to be used in layer B of the embodiment, the thermoplastic resins preferably used in layer B of the oxygen-absorbing multilayer injection-molded article in the third embodiment are mentioned.

<Ethylene-Vinyl Alcohol Copolymer>

As specific examples of the ethylene-vinyl alcohol copolymer to be used in layer B of the embodiment, the thermoplastic resins preferably used in layer B of the oxygen-absorbing multilayer injection-molded article in the third embodiment are mentioned.

<Vegetable-Derived Resin>

As specific examples of the vegetable-derived resin to be used in layer B of the embodiment, the thermoplastic resins preferably used in layer B of the oxygen-absorbing multilayer injection-molded article in the third embodiment are mentioned.

<Chlorine Resin>

As specific examples of the vegetable-derived resin to be used in layer B of the embodiment, the thermoplastic resins preferably used in layer B of the oxygen-absorbing multilayer injection-molded article in the third embodiment are mentioned.

As a preferable aspect of the oxygen-absorbing medical multilayer molded container of the embodiment, an aspect where the thermoplastic resin of the first resin layer (layer B) and the thermoplastic resin of the second resin layer (layer B) both are polyolefins; and an aspect where the thermoplastic resin of the first resin layer (layer B) and the thermoplastic resin of the second resin layer (layer B) both are polyesters are mentioned.

In an aspect where the thermoplastic resin of the first resin layer (layer B) and the thermoplastic resin of the second resin layer (layer B) are both polyesters, a polyester containing terephthalic acid or an ester-forming derivative thereof, or a naphthalene dicarboxylic acid or an ester-forming derivative thereof as a main acid component and an alkylene glycol as a main glycol component, is preferred among the aforementioned ones.

Note that the polyester containing terephthalic acid or an ester-forming derivative thereof as a main acid component is a polyester preferably containing the terephthalic acids or ester-forming derivatives thereof in total in an amount of 70 mole % or more based on the total of the acid components, more preferably in an amount of 80 mole % or more and further preferably in an amount of 90 mole % or more. Similarly, the polyester containing a naphthalene dicarboxylic acid or an ester-forming derivative thereof as a main acid component is a polyester preferably containing the naphthalene dicarboxylic acids or ester-forming derivatives thereof in total in an amount of 70 mole % or more, more preferably in an amount of 80 mole % or more and further preferably in an amount of 90 mole % or more.

Of the aforementioned naphthalene dicarboxylic acids or ester-forming derivatives of these, 1,3-naphthalene dicarboxylic acid, 1,4-naphthalene dicarboxylic acid, 1,5-naphthalene dicarboxylic acid, 2,6-naphthalene dicarboxylic acid and 2,7-naphthalene dicarboxylic acid, which are exemplified as dicarboxylic acids, or ester-forming derivatives of these, are preferred.

Another preferable example of the polyester to be used in layer B of the oxygen-absorbing multilayer injection-molded article of the embodiment includes poly(glycolic acid), which is obtained through polycondensation of a glycolic acid or methyl glycolate, or ring-opening polycondensation of glycolide. Note that the poly(glycolic acid) may be copolymerized with another component such as lactide.

In particular, as the polyester to be used in a resin layer (layer B) of the embodiment, a polyester containing terephthalic acid or an ester-forming derivative thereof or a naphthalene dicarboxylic acid or an ester-forming derivative thereof as a main acid component and containing an alkylene glycol as a main glycol component, is preferable. An alkylene glycol is preferably contained in an amount of 70 mole % or more in view of physical properties etc. and more preferably contained in an amount of 90 mole % or more. Of the aforementioned dicarboxylic acids, particularly, use of at least one element selected from the group consisting of terephthalic acid, isophthalic acid, 1,3-naphthalene dicarboxylic acid, 1,4-naphthalene dicarboxylic acid, 1,5-naphthalene dicarboxylic acid, 2,6-naphthalene dicarboxylic acid and 2,7-naphthalene dicarboxylic acid is preferable in view of physical properties etc. of the resultant polyester. These are preferably contained in an amount of 70 mole % or more. Of these dicarboxylic acids, particularly terephthalic acid and/or 2,6-naphthalene dicarboxylic acid are preferable. Furthermore, terephthalic acid and/or 2,6-naphthalene dicarboxylic acid are preferably contained in an amount of 70 mole % or more in view of physical properties etc., and more preferably in an amount of 90 mole % or more.

If necessary, another dicarboxylic acid may be copolymerized. Furthermore, use of at least one copolymer component selected from the group consisting of isophthalic acid, diethylene glycol, neo-pentyl glycol, 1,4-cyclohexane dimethanol, 1,2-propanediol, 1,3-propanediol and 2-methyl-1,3-propanediol is preferable in view of obtaining transparency and moldability at the same time, particularly at least one selected from the group consisting of isophthalic acid, diethylene glycol, neopentyl glycol and 1,4-cyclohexanedimethanol is more preferable.

The oxygen-absorbing medical multilayer molded container of the embodiment may have an optional layer, which varies depending upon desired performance etc., other than the aforementioned oxygen-absorbing layer (layer A) and resin layer (layer B) containing a thermoplastic resin. Examples of such an optional layer include an adhesion layer. The details of such an optional layer are the same as described in the third embodiment.

As a method for manufacturing the oxygen-absorbing medical multilayer molded container of the embodiment, a known method varying depending upon the properties of materials, a desired shape, etc. can be applied, but is not particularly limited. For example, a multilayer molded container can be manufactured by applying various types of injection molding methods. Note that the details of general injection molding of the multilayer body are the same as described in the third embodiment, and thus repetition of explanation is avoided herein.

The thickness of the oxygen-absorbing medical multilayer molded container of the embodiment is not particularly limited. In view of enhancing oxygen-absorbing performance; at the same time, ensuring physical properties required for a medical multilayer molded container, the thickness is preferably 3 to 5000 µm, more preferably 5 to 4500 µm and further preferably 10 to 4000 µm.

A multilayer molded article can be obtained by a method other than the injection molding method, for example, a compression molding method. To the resultant multilayer molded article, secondary processing is applied to mold the article into a container having a desired shape. For example, in a thermoplastic resin melt, an oxygen-absorbing resin composition is provided and a molten lump is supplied to a positive die and simultaneously compressed by a negative die and then compression molded product is cooled and solidified. In this manner, a multilayer molded article can be obtained. As the secondary processing, for example, extrusion molding, compression molding (sheet molding, blow-molding), etc. are applicable.

Usage of the oxygen-absorbing medical multilayer molded container of the embodiment is not particularly limited. The container can be used for various uses and in various forms. Examples of preferable usage thereof include, but not particularly limited to, vials, ampules, prefilled syringes and vacuum blood collection tubes. Now, preferable usage will be described in detail, below.

[Vial]

The oxygen-absorbing medical multilayer molded container of the embodiment can be used as a vial. Generally, a vial is constituted of a bottle, a rubber tap and a cap. The bottle is filled with a drug solution, stoppered by the rubber tap and further capped to hermetically close the bottle. The oxygen-absorbing medical multilayer molded container of the embodiment can be used as the bottle portion of the vial.

As a method for molding the oxygen-absorbing medical multilayer molded container of the embodiment into a bottle portion of a vial, for example, injection blow-molding and extrusion blow-molding are preferable. As a specific example thereof, an injection blow-molding method will be described below. For example, using a molding machine having two or more injectors and an injection mold, a material for constituting layer A and a material for constituting layer B are separately injected from respective injection cylinders through a mold hot runner into the cavity of the injection mold to manufacture a multilayer injection-molded article constituted of three layers (B/A/B) having a shape in accordance with a cavity shape of the injection mold. Furthermore, first, a material for constituting layer B is injected from the injection cylinder, and then, a material for constituting layer A is injected from another injection cylinder simultaneously with a resin for constituting layer B, subsequently, the resin for constituting layer B is injected in a necessary amount to fill the cavity to manufacture a multilayer injection-molded article constituted of three layers (B/A/B). Furthermore, first, a material for constituting layer B is injected, then a material for constituting layer A is solely injected, and finally the material for constituting layer B is injected in a necessary amount to fill the mold cavity to manufacture a multilayer injection-molded article constituted of five layers (B/A/B/A/B). Moreover, first, a material for constituting layer B1 is injected from an injection cylinder and then a material for constituting layer B2 is injected from another injection cylinder simultaneously with a resin for constituting layer B1, subsequently a resin for constituting layer A is injected simultaneously with resins for constituting layer B1 and layer B2 and thereafter the resin for constituting layer B1 is injected in a necessary amount to fill the cavity to manufacture a multilayer injection-molded article constituted of five layers (B1/B2/A/B2/B1). In the injection blow-molding, the multilayer injection-molded article obtained by the above method is heated to some extent. While keeping this state, the article is fit in a final-shape mold (blow mold) and air is fed to swollen the article, with the result that the article comes into contact with the mold. Then, the article was cooled and solidified to mold a bottle.

[Ampule]

The oxygen-absorbing medical multilayer molded container of the embodiment can be used as an ampule. Generally, an ampule is constituted of a small container having a narrow neck. The container is filled with a drug solution and the tip of the neck portion is welded to hermetically close the container. The oxygen-absorbing medical multilayer molded container of the embodiment can be used as the ampule (small container). As a method for molding the oxygen-absorbing medical multilayer molded container of the embodiment into an ampule, for example, injection blow-molding and extrusion blow-molding are preferred.

[Prefilled Syringe]

The oxygen-absorbing medical multilayer molded container of the embodiment can be used as a prefilled syringe. Generally, a prefilled syringe is at least constituted of a barrel to be filled with drug solution, a joint portion for joining an injection needle at an end of the barrel and a plunger for pushing the drug solution at the time of use. This is a syringe constituted in such a manner that a drug solution is stored in advance in a sealed condition in the barrel and the tip portion of the barrel is opened and an injection needle is fit to the barrel at the time of use. Owing to convenience, prefilled syringe is widely used. The oxygen-absorbing medical multilayer molded container of the embodiment can be used as the barrel.

As a method for molding the oxygen-absorbing medical multilayer molded container of the embodiment into a barrel of the prefilled syringe, for example, an injection molding method is preferred. To describe more specifically, first, a resin for constituting layer B is injected into the cavity of an injection mold in a predetermined amount. Then, a resin for constituting layer A is injected in a predetermined amount and the resin for constituting layer B is again injected in a predetermined amount to manufacture a multilayer injection-molded article serving as a barrel. Note that the barrel and the joint portion can be integrally molded or they are separately molded and then joined. After the barrel is filled with a drug solution, the tip portion of the joint portion must be sealed. As the sealing method, which is not particularly limited, a known method can be employed. For example, the resin of the joint tip portion is heated, melted and clipped by a pincher etc. to fuse.

The thickness of the barrel container of the prefilled syringe, which can be appropriately specified depending upon the purpose of use and size, is not particularly limited. Generally, in view of long-term storage stability of a drug solution, moldability and operability of the syringe, the thickness is preferably about 0.5 to 20 mm and more preferably about 0.5 to 5 mm. The thickness may be uniform or nonuniform. For the purpose of long-term storage stability, another gas barrier film and light blocking film may be further formed on the barrel surface. These optional films and a method for forming them are described, for example, in Japanese Patent Application Laid-Open No. 2004-323058.

[Vacuum Blood Collection Tube]

The oxygen-absorbing medical multilayer molded container of the embodiment can be used as a vacuum blood collection tube. Generally, a vacuum blood collection tube is constituted of a tubular body and a tap. The oxygen-absorbing medical multilayer molded container of the embodiment can be used as the tubular body.

As a method for molding the oxygen-absorbing medical multilayer molded container of the embodiment into a tubular body of a vacuum blood collection tube, for example, an injection molding method is preferred. To describe more specifically, first, a resin for constituting layer B is injected into the cavity of an injection mold in a predetermined amount and then a resin for constituting layer A is injected in a predetermined amount, and then, the resin for constituting layer B is injected again in a predetermined amount to manufacture a multilayer injection-molded article serving as the tubular body.

[Article to be Packed]

Examples of the article to be packed (filler) that is to be packed in the oxygen-absorbing medical multilayer molded container of the embodiment include, but not particularly limited to, arbitrary natural substances and compounds including vitamins such as vitamin A, vitamin B2, vitamin B12, vitamin C, vitamin D, vitamin E and vitamin K; alkaloids such as atropine; hormones such as adrenaline and insulin; sugars such as glucose and maltose; antibiotics such as ceftriaxone, cephalosporin and cyclosporine; and benzodiazepine medicinal agents such as oxazolam, flunitrazepam, clotiazepam and clobazam. When each of these natural substances and compounds is packed in the oxygen-absorbing medical multilayer molded container of the embodiment, the amount of natural substances and compounds adsorbed is small and deterioration of these by oxidation can be suppressed. In addition, evaporation of a solvent (for example moisture content) can be suppressed.

[Biopharmaceutical]

The oxygen-absorbing medical multilayer molded container of the embodiment can be preferably used as a storage container for biopharmaceutical. In view of the effect of the embodiment, as a biopharmaceutical that can be preferably used include protein preparations and nucleic acid pharmaceutical preparations. Specific examples thereof include, but not particularly limited to, monoclonal antibodies, vaccines, interferon, insulin, growth hormone, erythropoietin, colony stimulating factor, TPA, interleukin, blood coagulation factor VIII, blood coagulation factor IX, sodium diuresis hormone, somatomedin, glucagon, serum albumin, calcitonin, growth hormone-releasing factor, digestive enzymes, anti-inflammatory enzymes, antibiotics, antisense nucleic acids, antigene nucleic acids, decoy nucleic acids, aptamers, siRNA and microRNA. When each of these biopharmaceuticals is packed in a medical multilayer container, the amount of these biopharmaceuticals adsorbed is small and deterioration of these medicines by oxidation and reduction of drug efficacy can be suppressed. In addition, evaporation of a solvent (for example moisture content) can be suppressed.

Note that, before and after packing of these articles, sterilization treatment can be applied to medical multilayer containers and the articles by a method suitable for the articles. Examples of a sterilization method include a hot water treatment performed at 100° C. or less, a hot water treatment under application of pressure performed at 100° C. or more, thermal sterilization performed at a temperature as high as 121° C. or more, sterilization by electromagnetic wave such as UV ray, microwave and gamma ray, a treatment with a gas such as ethylene oxide and sterilization with a chemical agent such as hydrogen peroxide and hypochlorite.

EXAMPLES

The present invention will be more specifically described by use of Examples and Comparative Examples, below; however, the present invention is not limited by these. Unless otherwise specified, NMR measurement was performed at room temperature. In Examples and Comparative Examples, physical property values were obtained by using the following measurement methods and measurement apparatuses.

(Method for Measuring Glass Transition Temperature)

Glass transition temperature was measured in accordance with JIS K7122. As a measurement apparatus, "DSC-60", manufactured by Shimadzu Corporation was used.

(Method for Measuring Melting Point)

As the melting point, a DSC melting point peak temperature was measured in accordance with ISO11357. As a measurement apparatus, "DSC-60", manufactured by Shimadzu Corporation was used.

Synthesis Example 1 of Monomer

Synthesis Example 1-1

To an autoclave of 18 L (inner volume), dimethyl naphthalene-2,6-dicarboxylate (2.20 kg), 2-propanol (11.0 kg) and a catalyst (350 g containing 50 wt % of water) of 5% palladium immobilized on active carbon were supplied. Subsequently, the air within the autoclave was replaced with nitrogen and the nitrogen was further replaced with hydrogen. Thereafter, hydrogen was supplied until the interior pressure of the autoclave reached 0.8 MPa. Next, a stirrer was driven and a rotation speed was adjusted to be 500 rpm. After the interior temperature was increased up to 100° C. over 30 minutes, hydrogen was further supplied to set a pressure at 1 MPa. After that, hydrogen was continuously supplied in accordance with a reduction of pressure with the progression of a reaction so as to maintain 1 MPa. Seven hours later, since pressure reduction was stopped, the autoclave was cooled and unreacted residual hydrogen was released, and then the reaction solution was taken out from the autoclave. After the reaction solution was filtered and the catalyst was removed, 2-propanol was distilled away from the separated filtrate by an evaporator. To the crude product obtained, 2-propanol (4.40 kg) was added. Dimethyl tetralin-2,6-dicarboxylate was purified by recrystallization in a yield of 80%. Note that NMR analysis results are as follows. 1H-NMR (400 MHz CDCl$_3$) δ7.76-7.96 (2H m), 7.15 (1H d), 3.89 (3H s), 3.70 (3H s), 2.70-3.09 (5H m), 1.80-1.95 (1H m).

Subsequently, a 10 L flask was charged with the obtained dimethyl tetralin-2,6-dicarboxylate (1.00 kg), a 16 wt % aqueous ethanol solution (8.0 kg) and sodium hydroxide (360 g). The mixture was stirred at 80° C. for 4 hours to perform hydrolysis. Thereafter, to the mixture, 36% hydrochloric acid was added until pH reached to 7. The crude product was precipitated, separated by filtration and vacuum-dried to obtain tetralin-2,6-dicarboxylic acid in a yield of 90%. Note that NMR analysis results are as follows. 1H-NMR (400 MHz ((D$_3$C)$_2$S=O) δ12.41-12.75 (2Hbr), 7.65 (2Hm), 7.23 (1Hd), 3.70 (3Hs), 2.60-3.45 (5Hm), 2.05-2.13 (1Hm), 1.70-1.79 (1Hm).

Production Example 1 of Polymer

Production Example 1-1

To an autoclave having an inner volume of 200 mL and equipped with a thermometer, a pressure gage, a nitrogen introducing port and a pressure discharge hole, tetralin-2,6-dicarboxylic acid (17.18 g (78.0 mmol)) obtained in Synthesis Example 1-1, dodecamethylenediamine (15.63 g (78.0 mmol)) and distilled water (19 g) were supplied. The autoclave was purged with nitrogen, and then, the interior temperature of the autoclave was raised up to 220° C. over 2 hours and maintained at a pressure of 2 MPaG for 2 hours. Thereafter, the pressure was reduced to normal pressure while the interior temperature of the autoclave was raised up to 320° C. over one hour. After maintained at 320° C. and normal pressure for 30 minutes, the autoclave was cooled to obtain a tetralin ring-containing polyamide compound (1-1). The glass transition temperature of the obtained polyamide compound (1-1) was 111° C. and the melting point thereof was 262° C. The relative viscosity of the polyamide compound (1-1) was 3.7. The starting composition is shown in Table 1.

Production Example 1-2

To the same type of autoclave as used in Production Example 1-1, tetralin-2,6-dicarboxylic acid (11.64 g (52.9 mmol)) obtained in Synthesis Example 1-1, azelaic acid (2.48 g (13.2 mmol)), dodecamethylenediamine (13.24 g (66.1 mmol)) and distilled water (12 g) were supplied and a tetralin ring-containing polyamide compound (1-2) was synthesized in the same manner as in Production Example 1-1. The glass transition temperature of the polyamide compound (1-2) was 94° C. and the melting point thereof was 246° C. The relative viscosity thereof was 3.5. The starting composition is shown in Table 1.

Production Example 1-3

To the same type of autoclave as used in Production Example 1-1, tetralin-2,6-dicarboxylic acid (15.11 g (68.6 mmol)) obtained in Synthesis Example 1-1, sebacic acid (13.88 g (68.6 mmol)), hexamethylenediamine (15.95 g (137.2 mmol)) and distilled water (12 g) were supplied and a tetralin ring-containing polyamide compound (1-3) was synthesized in the same manner as in Production Example 1-1. The glass transition temperature of the polyamide compound (1-3) was 87° C. and the melting point thereof was 250° C. The relative viscosity thereof was 2.6. The starting composition is shown in Table 1.

Production Example 1-4

To the same type of autoclave as used in Production Example 1-1, tetralin-2,6-dicarboxylic acid (11.22 g (51.0 mmol)) obtained in Synthesis Example 1-1, hexamethylenediamine (5.93 g (50.9 mmol)), ε-caprolactam (11.54 g (102.0 mmol)) and distilled water (12 g) were supplied and a tetralin ring-containing polyamide compound (1-4) was synthesized in the same manner as in Production Example 1-1. The glass transition temperature of the polyamide compound (1-4) was 96° C. and the melting point thereof was 219° C. The relative viscosity thereof was 2.4. The starting composition is shown in Table 1.

TABLE 1

| Polyamide compound | Dicarboxylic acid | | Diamine | Aminocarboxylic acid |
|---|---|---|---|---|
| Polyamide compound (1-1) | Tetralin-2,6-dicarboxylic acid 50 | — | Dodecamethylenediamine 50 | — |
| Polyamide compound (1-2) | Tetralin-2,6-dicarboxylic acid 40 | Azelaic acid 10 | Dodecamethylenediamine 50 | — |
| Polyamide compound (1-3) | Tetralin-2,6-dicarboxylic acid 25 | Sebacic acid 25 | Hexamethylenediamine 50 | — |
| Polyamide compound (1-4) | Tetralin-2,6-dicarboxylic acid 25 | — | Hexamethylenediamine 25 | ε-caprolactam 50 |

A numerical value described under the name of a compound denotes starting molar ratio.

Example 1-1

With a polyamide compound (1-1) (100 parts by mass), cobalt stearate (II) (0.1 parts by mass in terms of cobalt) was dry-blended. The obtained mixture was formed into a film by use of a double-screw extruder having two screws of 15 mm in diameter at an extrusion temperature of 290° C., a screw rotation number of 20 rpm, a feed screw rotation number of 16 rpm and a haul-off speed of 0.3 m/min. In this manner, an oxygen-absorbing film having a width of 80 mm and a thickness of 95 to 105 μm was manufactured.

Next, two gas barrier bags formed of an aluminum foil laminate film were prepared. One test piece (50 mm in length×200 mm in width) of the obtained oxygen-absorbing film were put in the two gas barrier bags together with 300 cc of air. The relative humidity in one of the bags was adjusted to be 100%; whereas the relative humidity of the other bag was adjusted to be 30% and then the bags were separately sealed. The sealed bags thus obtained were stored at 40° C. for 14 days. The total amount of oxygen absorbed during this period was measured. Similarly, sealed bags were manufactured so as to have a relative humidity of 100% and stored at 40° C. and under a relative humidity of 100% for one month. The appearance of the film after the storage of one month was visually checked and odor after the bag was opened was checked. These results are shown in Table 2.

Example 1-2

An oxygen-absorbing film was manufactured in the same manner as in Example 1-1 except that a polyamide compound (1-2) was used in place of the polyamide compound (1-1) and the extrusion temperature was changed from 290° C. to 270° C. The amount of oxygen absorbed by the film was measured; appearance of the film was visually evaluated; and odor was checked. These results are shown in Table 2.

Example 1-3

An oxygen-absorbing film was manufactured in the same manner as in Example 1-1 except that a polyamide compound (1-3) was used in place of the polyamide compound (1-1) and the extrusion temperature was changed from 290° C. to 270° C. The amount of oxygen absorbed of the film was measured; appearance of the film was visually evaluated; and odor was checked. These results are shown in Table 2.

Example 1-4

An oxygen-absorbing film was manufactured in the same manner as in Example 1-1 except that a polyamide compound (1-4) was used in place of the polyamide compound (1-1) and the extrusion temperature was changed from 290° C. to 240° C. The amount of oxygen absorbed of the film was measured; appearance of the film was visually evaluated; and odor was checked. These results are shown in Table 2.

Comparative Example 1-1

An oxygen-absorbing film was manufactured in the same manner as in Example 1-1 except that N-MXD6 (trade name: MX nylon S6011, manufactured by Mitsubishi Gas Chemical Company Inc.) was used in place of the polyamide compound (1-1) and the extrusion temperature was changed from 290° C. to 250° C. The amount of oxygen absorbed of the film was measured, appearance of the film was visually observed, and odor was checked. These results are shown in Table 2.

TABLE 2

| | Resin used in oxygen-absorbing resin composition | Amount of oxygen absorbed[1] | | Appearance[2] | Odor[2] |
|---|---|---|---|---|---|
| | | Humidity 100% | Humidity 30% | | |
| Example 1-1 | Polyamide compound (1-1) | 12 cc | 6 cc | Shape was maintained | None |
| Example 1-2 | Polyamide compound (1-2) | 9 cc | 6 cc | Shape was maintained | None |
| Example 1-3 | Polyamide compound (1-3) | 12 cc | 7 cc | Shape was maintained | None |
| Example 1-4 | Polyamide compound (1-4) | 18 cc | 9 cc | Shape was maintained | None |
| Comparative Example 1-1 | N-MXD6 | 10 cc | 2 cc | Collapsed | None |

[1]Total amount of oxygen absorbed during 14 days from initiation of test
[2]Evaluated after one-month storage at 40° C. and a humidity of 100%

As is apparent from the result shown in Table 2, the oxygen-absorbing resin compositions of the present invention delivered satisfactory oxygen-absorbing performance both in high humidity and low humidity conditions and the shapes of films were maintained even after absorption of oxygen without collapse and no odor was sensed.

Production Example 2 of Polymer

Production Example 2-1

To an autoclave having an inner volume of 2 L and equipped with a thermometer, a pressure gage, a nitrogen introducing port and a pressure discharge hole, tetralin-2,6-dicarboxylic acid (171.8 g (780 mmol)) obtained in Synthesis Example 1-1, dodecamethylenediamine (156.3 g (780 mmol)) and distilled water (190 g) were supplied. The autoclave was purged with nitrogen, and then the interior temperature of the autoclave was raised up to 220° C. over 2 hours and maintained at a pressure of 2 MPaG for 2 hours. Thereafter, the pressure was reduced to normal pressure while the interior temperature of the autoclave was raised up to 320° C. over one hour. After maintained at 320° C. and normal pressure for 30 minutes, the autoclave was cooled to obtain a tetralin ring-containing polyamide compound (2-1). The glass transition temperature of the obtained polyamide compound (2-1) was 111° C. and the melting point thereof was 262° C. The relative viscosity of the polyamide compound (2-1) was 3.7. The starting composition is shown in Table 3.

Production Example 2-2

To the same type of autoclave as used in Production Example 2-1, tetralin-2,6-dicarboxylic acid (116.4 g (529 mmol)) obtained in Synthesis Example 1-1, azelaic acid (24.8 g (132 mmol)), dodecamethylenediamine (132.4 g (661 mmol)) and distilled water (120 g) were supplied and a tetralin ring-containing polyamide compound (2-2) was synthesized in the same manner as in Production Example 2-1. The glass transition temperature of the polyamide compound (2-2) was 94° C. and the melting point thereof was 246° C. The relative viscosity thereof was 3.5. The starting composition is shown in Table 3.

Production Example 2-3

To the same type of autoclave as used in Production Example 2-1, tetralin-2,6-dicarboxylic acid (151.1 g (686 mmol)) obtained in Synthesis Example 1-1, sebacic acid (138.8 g (686 mmol)), hexamethylenediamine (159.5 g (1372 mmol)) and distilled water (120 g) were supplied and a tetralin ring-containing polyamide compound (2-3) was synthesized in the same manner as in Production Example 2-1. The glass transition temperature of the polyamide compound (2-3) was 87° C. and the melting point thereof was 250° C. The relative viscosity thereof was 2.6. The starting composition is shown in Table 3.

Production Example 2-4

To the same type of autoclave as used in Production Example 2-1, tetralin-2,6-dicarboxylic acid (112.2 g (510 mmol)) obtained in Synthesis Example 1-1, hexamethylenediamine (59.3 g (509 mmol)), ε-caprolactam (115.4 g (1020 mmol)) and distilled water (120 g) were supplied and a tetralin ring-containing polyamide compound (2-4) was synthesized in the same manner as in Production Example 2-1. The glass transition temperature of the polyamide compound (2-4) was 96° C. and the melting point thereof was 219° C. The relative viscosity thereof was 2.4. The starting composition is shown in Table 3.

TABLE 3

| Polyamide compound | Dicarboxylic acid | | Diamine | Aminocarboxylic acid |
|---|---|---|---|---|
| Polyamide compound (2-1) | Tetralin-2,6-dicarboxylic acid 50 | — | Dodecamethylenediamine 50 | — |
| Polyamide compound (2-2) | Tetralin-2,6-dicarboxylic acid 40 | Azelaic acid 10 | Dodecamethylenediamine 50 | — |
| Polyamide compound (2-3) | Tetralin-2,6-dicarboxylic acid 25 | Sebacic acid 25 | Hexamethylenediamine 50 | — |
| Polyamide compound (2-4) | Tetralin-2,6-dicarboxylic acid 25 | — | Hexamethylenediamine 25 | ε-caprolactam 50 |

A numerical value described under the name of a compound denotes starting molar ratio.

Example 2-1

With a polyamide compound (2-1) (100 parts by mass), cobalt stearate (II) (0.05 parts by mass in terms of cobalt) was dry-blended. The obtained mixture was supplied to a single film manufacturing apparatus equipped with an extruder, a T die, a cooling roll and a winder, to manufacture a film having a thickness of 120 μm.

Subsequently, the film was simultaneously and biaxially stretched two fold lengthwise and two fold widthwise by a batch-system biaxial stretching machine (biaxial stretching machine of center stretching type, manufactured by Toyo Seiki Kogyo Co. Ltd.) under the conditions: heating temperature of 150° C., draw ratio of 2000 mm/min, heat fixation temperature of 200° C., and heat fixation time of 30 seconds, to manufacture a biaxially stretched film (a single-layer stretched film) having a thickness of 30 μm. Both surfaces of the obtained film were treated with corona discharge to manufacture an oxygen-absorbing film (OA1).

Next, using a urethane-base dry laminate adhesive (trade name: TAKELAC A505/TAKENATE A20, manufactured by Mitsui Chemicals, Inc.,) a silica vapor deposition PET film (trade name: Tech barrier TXR, manufactured by Mitsubishi Plastics Inc.,) was laminated with a linear low-density polyethylene film (trade name: T.U.X FC-S, hereinafter referred also to "LLDPE", manufactured by Mitsui Chemicals Tohcello, Inc.,) by a dry laminator to obtain an oxygen-absorbing multilayer film formed of an oxygen-absorbing multilayer body consisting of the silica vapor deposition PET film (thickness: 12 μm)/adhesive (thickness: 3 μm)/OA1 (thickness: 30 μm)/adhesive (thickness: 3 μm)/LLDPE (thickness: 40 μm).

Next, a three-side sealed bag of 10 cm×20 cm was manufactured from the obtained oxygen-absorbing multilayer film with the LLDPE layer faced inside and charged with vitamin C tablets (100 g) and then sealed. The sealed bag thus obtained was stored at 40° C. under 50% RH in a dark place. After storage for 7 days and 2 months, the oxygen concentration in the bag was measured. The sealed bag after storage of 2 months was opened and appearance of the vitamin C tablets and odor within the bag were checked. Furthermore, the sealing strength of bags before and after storage of 6 months was measured. These results are shown in Table 4. Note that the sealing strength of short side of the three-side sealed bag was measured in accordance with JIS 20238 (the same shall apply hereinafter).

Example 2-2

An oxygen-absorbing multilayer film was obtained in the same manner as in Example 2-1 except that a polyamide compound (2-2) was used in place of the polyamide compound (2-1), and then a three-side sealed bag was manufactured. The oxygen concentration measurement, appearance observation, odor evaluation and sealing strength measurement with respect to the three-side sealed bag were performed in the same manner as in Example 2-1. These results are shown in Table 4.

Example 2-3

An oxygen-absorbing multilayer film was obtained in the same manner as in Example 2-1 except that a polyamide compound (2-3) was used in place of the polyamide compound (2-1), and then a three-side sealed bag was manufactured. The oxygen concentration measurement, appearance observation, odor evaluation and sealing strength measurement with respect to the three-side sealed bag were performed in the same manner as in Example 2-1. These results are shown in Table 4.

Example 2-4

An oxygen-absorbing multilayer film was obtained in the same manner as in Example 2-1 except that a polyamide compound (2-4) was used in place of the polyamide compound (2-1), and then a three-side sealed bag was manufactured. The oxygen concentration measurement, appearance observation, odor evaluation and sealing strength measurement with respect to the three-side sealed bag were performed in the same manner as in Example 2-1. These results are shown in Table 4.

Comparative Example 2-1

An oxygen-absorbing multilayer film was obtained in the same manner as in Example 2-1 except that N-MXD6 (trade name: MX nylon S6007, manufactured by Mitsubishi Gas Chemical Company, Inc.) was used in place of the polyamide compound (2-1), and then a three-side sealed bag was manufactured. The oxygen concentration measurement, appearance observation, odor evaluation and sealing strength measurement with respect to the three-side sealed bag were performed in the same manner as in Example 2-1. These results are shown in Table 4.

Comparative Example 2-2

A multilayer film was obtained in the same manner as in Example 2-1 except that a single-layer stretched film was manufactured by using nylon 6 (trade name: UBE nylon6 1022B, manufactured by Ube Industries, Ltd.) in place of the polyamide compound (2-1) and adding no cobalt stearate, and then a three-side sealed bag was manufactured. The oxygen concentration measurement, appearance observation, odor evaluation and sealing strength measurement with respect to the three-side sealed bag were performed in the same manner as in Example 2-1. These results are shown in Table 4.

TABLE 4

| | Polyamide compound | Oxygen concentration (vol %) After 7 days | Oxygen concentration (vol %) After 2 months | Color tone of vitamin C tablets[1] | Odor in bag[1] | Sealing strength (kg/15 mm) Before storage | Sealing strength (kg/15 mm) After storage[2] |
|---|---|---|---|---|---|---|---|
| Example 2-1 | Polyamide compound (2-1) | 4.5 | 0.1 or less | Satisfactory | None | 4.2 | 3.9 |
| Example 2-2 | Polyamide compound (2-2) | 5.9 | 0.1 or less | Satisfactory | None | 4.5 | 4.0 |
| Example 2-3 | Polyamide compound (2-3) | 6.3 | 0.1 or less | Satisfactory | None | 4.3 | 3.8 |
| Example 2-4 | Polyamide compound (2-4) | 4.9 | 0.1 or less | Satisfactory | None | 4.5 | 4.1 |
| Comparative Example 2-1 | N-MXD6 | 20.1 | 16.2 | Yellow change | None | 4.4 | 4.1 |
| Comparative Example 2-2 | Nylon 6 single layer | 20.4 | 17.8 | Yellow change | None | 4.6 | 4.4 |

[1]Results after 2-month storage
[2]Results after 6-month storage

As is apparent from Examples 2-1 to 2-4, the oxygen-absorbing multilayer bodies of the present invention exhibit satisfactory oxygen-absorbing performance under low humidity condition and still maintain strength after oxygen absorption.

Example 2-5

The polyamide compound (2-1) and cobalt stearate (II) (0.05 parts by mass in terms of cobalt based on the polyamide compound (2-1) (100 parts by mass)) were supplied to a double-screw extruder having two screws of 37 mm in diameter and melt-kneading was performed to obtain an oxygen-absorbing resin composition.

Subsequently, using a multilayer film manufacturing apparatus equipped with three extruders, a feed block, a T die, a cooling roll, a winder, etc., nylon 6 (trade name: UBE nylon6 1022B, manufactured by Ube Industries, Ltd.) was extruded from first and third extruders, whereas the oxygen-absorbing resin composition obtained above was extruded from a second extruder and passed through the feed block to manufacture a multilayer film of a three-layer structure using two types of materials, i.e., constituted of nylon 6 (thickness: 90 µm)/an oxygen-absorbing resin composition (thickness: 180 µm)/nylon 6 (thickness: 90 µm).

Subsequently, the obtained multilayer film was simultaneously and biaxially stretched three fold lengthwise and three fold widthwise by a batch-system biaxial stretching machine (biaxial stretching machine of center stretching type, manufactured by Toyo Seiki Kogyo Co. Ltd.) under the conditions: heating temperature of 150° C., draw ratio of 2000 mm/min, heat fixation temperature of 190° C., and heat fixation time of 30 seconds, to manufacture a biaxially stretched film having a thickness of 30 µm. Both surfaces of the obtained film were treated with corona discharge to manufacture an oxygen-absorbing film (OA2). Note that the thickness of individual layers after stretched was 10/20/10 (µm).

Subsequently, an oxygen-absorbing multilayer film formed of an oxygen-absorbing multilayer body consisting of a silica vapor deposition PET film (thickness: 12 µm)/adhesive (thickness: 3 µm)/OA2 (thickness: 40 µm)/adhesive (thickness: 3 µm)/LLDPE (thickness: 40 µm) was obtained in the same manner as in Example 2-1 except that the oxygen-absorbing film (OA2) was used in place of the oxygen-absorbing film (OA1). A three-side sealed bag was manufactured in the same manner as in Example 2-1 except that the oxygen-absorbing multilayer film was used. The three-side sealed bag manufactured was charged with pineapple (80 g) and fruit syrup (80 g), sealed so as to have a head space air amount of 5 cc, boiled at 90° C. for 30 minutes and stored in a dark place at 40° C. under 80% RH. After storage for 7 days and 2 months, the oxygen concentration in the bag was measured. The sealed bag after storage of 2 months was opened and flavor of pineapple and odor within the bag were checked. Furthermore, the sealing strength of bags before and after storage of 6 months was measured. These results are shown in Table 5.

Example 2-6

An oxygen-absorbing multilayer film was obtained in the same manner as in Example 2-5 except that a polyamide compound (2-2) was used in place of the polyamide compound (2-1), and then a three-side sealed bag was manufactured. The oxygen concentration measurement, flavor and odor evaluation and sealing strength measurement with respect to the three-side sealed bag were performed in the same manner as in Example 2-5. These results are shown in Table 5.

Example 2-7

An oxygen-absorbing multilayer film was obtained in the same manner as in Example 2-5 except that a polyamide compound (2-3) was used in place of the polyamide compound (2-1), and then a three-side sealed bag was manufactured. The oxygen concentration measurement, flavor and odor evaluation and sealing strength measurement with respect to the three-side sealed bag were performed in the same manner as in Example 2-5. These results are shown in Table 5.

Example 2-8

An oxygen-absorbing multilayer film was obtained in the same manner as in Example 2-5 except that a polyamide compound (2-4) was used in place of the polyamide compound (2-1), and then a three-side sealed bag was manufactured. The oxygen concentration measurement, flavor and odor evaluation and sealing strength measurement with respect to the three-side sealed bag were performed in the same manner as in Example 2-5. These results are shown in Table 5.

Comparative Example 2-3

An oxygen-absorbing multilayer film was obtained in the same manner as in Example 2-5 except that N-MXD6 was used similarly to Comparative Example 2-1, in place of the polyamide compound (2-1), and then a three-side sealed bag was manufactured. The oxygen concentration measurement, flavor and odor evaluation and sealing strength measurement with respect to the three-side sealed bag were performed in the same manner as in Example 2-5. These results are shown in Table 5.

Comparative Example 2-4

A single-layer stretched film was manufactured in the same manner as in Comparative Example 2-2 by using Nylon 6 similarly to Comparative Example 2-2 in place of the polyamide compound (2-1) and adding no cobalt stearate. After a multilayer film was obtained in the same manner as in Example 2-5 except that the single-layer stretched film was used in place of the biaxially-stretched film, and then a three-side sealed bag was manufactured. The oxygen concentration measurement, flavor and odor evaluation and sealing strength measurement with respect to the three-side sealed bag were performed in the same manner as in Example 2-5. These results are shown in Table 5.

TABLE 5

| | Polyamide compound | Oxygen concentration (vol %) | | | | Sealing strength (kg/15 mm) | |
|---|---|---|---|---|---|---|---|
| | | After 7 days | After 2 months | Flavor[1] | Odor in bag[1] | Before storage | After storage[2] |
| Example 2-5 | Polyamide compound (2-1) | 3.0 | 0.1 or less | Satisfactory | None | 5.3 | 5.1 |
| Example 2-6 | Polyamide compound (2-2) | 3.9 | 0.1 or less | Satisfactory | None | 5.4 | 5.4 |
| Example 2-7 | Polyamide compound (2-3) | 4.1 | 0.1 or less | Satisfactory | None | 5.2 | 5.1 |
| Example 2-8 | Polyamide compound (2-4) | 3.3 | 0.1 or less | Satisfactory | None | 5.7 | 5.5 |
| Comparative Example 2-3 | N-MXD6 | 6.4 | 0.8 | Satisfactory | None | 5.3 | 1.8 |
| Comparative Example 2-4 | Nylon 6 single layer | 20.4 | 19.8 | Reduced | None | 5.6 | 5.2 |

[1]Results after 2-month storage
[2]Results after 6-month storage

As is apparent from Examples 2-5 to 2-8, the oxygen-absorbing multilayer bodies of the present invention exhibit satisfactory oxygen-absorbing performance under high humidity condition and still maintain strength after oxygen absorption.

Example 3-1

With the polyamide compound (1-1) (100 parts by mass), cobalt stearate (II) (0.03 parts by mass in terms of cobalt) was dry-blended. The obtained mixture was supplied to a double-screw extruder having two screws of 37 mm in diameter, at a rate of 15 kg/h. Melt-kneading was performed at a cylinder temperature of 280° C. and a strand was extruded from an extruder head. After cooling, the strand was pelletized to obtain an oxygen-absorbing resin composition.

Subsequently, under the following conditions, the thermoplastic resin for constituting layer B was injected from an injection cylinder and then the resin composition for constituting layer A was injected from another injection cylinder simultaneously with the thermoplastic resin for constituting layer B. Subsequently, the thermoplastic resin for constituting layer B was injected in a necessary amount to fill a cavity to form an injection-molded article (test tube-form parison) of three layers, i.e., constituted of layer B/layer A/layer B. The total mass of the parison was specified as 25 g and the mass of layer A was specified as 10 mass % based on the total mass of the parison. Note that polyethylene terephthalate (trade name: BK-2180, manufactured by Japan Unipet) was used as the thermoplastic resin for constituting layer B, and the above oxygen-absorbing resin composition was used as the resin composition for constituting layer A.

(Shape of Parison)

The whole length of a parison was specified as 95 mm, the outer diameter as 22 mm and the film thickness as 2.7 mm. Note that a parison was manufactured by use of an injection molding machine (Type: M200, proving 4 parisons, manufactured by Meiki Co., Ltd.).

(Molding Conditions for Parison)

Temperature of injection cylinder for layer A: 280° C.
Temperature of injection cylinder for layer B: 280° C.
Temperature of resin flow channel in mold: 280° C.
Temperature of cooling water for mold: 15° C.

The obtained parison was cooled and then subjected to a secondary processing, in which the parison was heated and shaped by biaxial stretching blow molding to manufacture a multilayer bottle (oxygen-absorbing multilayer container).

(Shape of Bottle Obtained by Secondary Processing)

The whole length of a bottle was specified as 160 mm, an outer diameter as 60 mm, an inner volume as 350 mL and a film thickness as 0.28 mm. The draw ratio was specified as 1.9 folds lengthwise and 2.7 folds widthwise. The shape of the bottom was a champagne-bottle type. The base of bottle has a dimple. Note that a blow molding machine (type: EFB 1000ET, manufactured by FRONTIER Inc.) was used for secondary processing.

(Secondary Processing Conditions)

Heating temperature of parison: 100° C.
Pressure of a stretching rod: 0.5 MPa
Primary blow pressure: 0.7 MPa
Secondary blow pressure: 2.5 MPa
Primary blow delayed time: 0.33 sec
Primary blow time: 0.35 sec
Secondary blow time: 2.0 sec
Blow discharge time: 0.6 sec
Mold temperature: 30° C.

Subsequently, the oxygen transmission rate of the obtained container was measured at 23° C. and under an atmosphere having a relative humidity of 50%, which was measured outside the container and a relative humidity of 100%, which was measured within the container. Measurement herein was performed by use of an oxygen transmission rate measurement apparatus (trade name: OX-TRAN 2-61, manufactured by MOCON). The lower the measurement value, the more satisfactory oxygen barrier property. The oxygen transmission rate after 14 days from initiation of measurement is shown in Table 6.

Example 3-2

An oxygen-absorbing resin composition, a parison and a multilayer bottle were manufactured in the same manner as Example 3-1 except that a polyamide compound (1-2) was used in place of the polyamide compound (1-1). The oxygen transmission rate of the multilayer bottle was measured. The evaluation results are shown in Table 6.

Example 3-3

An oxygen-absorbing resin composition, a parison and a multilayer bottle were manufactured in the same manner as in Example 3-1 except that a polyamide compound (1-3) was used in place of the polyamide compound (1-1). The oxygen transmission rate of the multilayer bottle was measured. The evaluation results are shown in Table 6.

Example 3-4

An oxygen-absorbing resin composition, a parison and a multilayer bottle were manufactured in the same manner as in Example 3-1 except that a polyamide compound (1-4) was used in place of the polyamide compound (1-1). The oxygen transmission rate of the multilayer bottle was measured. The evaluation results are shown in Table 6.

Comparative Example 3-1

A single-layer bottle having the same shape as in Example 3-1 was manufactured in the same manner as in Example 3-1 except that the polyamide compound (1-1) and cobalt stearate (II) were not added and polyethylene terephthalate (trade name: BK-2180, manufactured by Japan Unipet) (100 parts by mass) was used. The oxygen transmission rate of the single-layer bottle was measured in the same manner as in Example 3-1. The evaluation results are shown in Table 6.

TABLE 6

|  | Layer constitution of bottle | Oxygen transmission rate/14th day mL/ (0.21 atm · day · package) |
|---|---|---|
| Example 3-1 | PET/Polyamide compound (1-1)/PET | 0.021 |
| Example 3-2 | PET/Polyamide compound (1-2)/PET | 0.023 |
| Example 3-3 | PET/Polyamide compound (1-3)/PET | 0.025 |
| Example 3-4 | PET/Polyamide compound (1-4)/PET | 0.022 |
| Comparative Example 3-1 | PET | 0.040 |

As is apparent from Table 6, it was confirmed that the oxygen-absorbing containers of Examples 3-1 to 3-4, since oxygen is absorbed by the oxygen-absorbing layer, have low oxygen transmission rates compared to conventional PET bottle (Comparative Example 3-1) and thus these containers are excellent in oxygen barrier property.

Now, the oxygen-absorbing medical multilayer molded container of the present invention will be more specifically described below by way of Examples and Comparative Examples; however, the present invention is not limited by these. Note that vials are taken as an example and demonstrated in the following Examples. As is described in the specification of the present application, since characteristics demanded for ampules and prefilled syringes are the same as for vials, the present invention is not particularly limited by the following Examples.

Example 4-1

With a polyamide compound (1-1) (100 parts by mass), cobalt stearate (II) (0.1 parts by mass in terms of cobalt) was dry-blended. The obtained mixture was supplied to a double-screw extruder having two screws of 37 mm in diameter, at a rate of 15 kg/h. Melt-kneading was performed at a cylinder temperature of 290° C. and a strand was extruded from an extruder head. After cooling, the strand was pelletized to obtain an oxygen-absorbing resin composition (4-1). Subsequently, as shown below, a multilayer injection molded container, i.e., vial, was manufactured by using the oxygen-absorbing resin composition (4-1). Thereafter, performance of the obtained vial was evaluated as shown below. The evaluation results are shown in Table 7.

[Manufacturing of Vial]

Under the following conditions, the thermoplastic resin for constituting a resin layer (layer B) was injected from an injection cylinder and then the oxygen-absorbing resin composition (4-1) for constituting an oxygen-absorbing layer (layer A) was injected from another injection cylinder simultaneously with the thermoplastic resin for constituting layer B. Subsequently, a thermoplastic resin for constituting layer B was injected in a necessary amount to fill the cavity of an injection mold to obtain an injection molded article of a three-layer constitution (B/A/B). Thereafter, the obtained injection-molded article was cooled to a predetermined temperature and transferred to a mold for blow molding. Blow molding was performed to manufacture a vial (bottle portion). The total mass of the vial herein was specified as 24 g and the mass of layer A was specified as 30 mass % of the total mass of the vial. A cycloolefin copolymer (trade name: TOPAS6013, manufactured by Ticona GmbH) was used as the thermoplastic resin for constituting layer B.
(Shape of Vial)
The whole length of a vial was specified as 89 mm, the outer diameter as 40 mmφ and the film thickness as 1.8 mm. Note that a vial was manufactured by use of an integrated injection blow molding machine (Type: IBS 85, proving 4 vials, manufactured by UNILOY).
(Molding Conditions for Vial)
Temperature of injection cylinder for layer A: 280° C.
Temperature of injection cylinder for layer B: 280° C.
Temperature of resin flow channel in injection mold: 280° C.
Blowing temperature: 150° C.
Temperature of cooling water for blow mold: 15° C.
[Performance Evaluation of Vial]
Measurement of oxygen transmission rate, evaluation of appearance after molding, drop test and elution test of the obtained vials were performed in accordance with the following methods and evaluation was made based on the following criteria.
(1) Oxygen Transmission Rate of Vial (OTR)
At the 30th day from initiation of measurement, the oxygen transmission rate was measured at 23° C. and under an atmosphere having a relative humidity of 50%, which was measured outside the molded article and a relative humidity of 100%, which was measured within the molded article. Measurement was performed by use of an oxygen transmission rate measurement apparatus (trade name: OX-TRAN 2-21ML, manufactured by MOCON). The lower the measurement value, the more satisfactory the oxygen barrier property. Note that detection lower limit of oxygen transmission rate measured is $5 \times 10^{-5}$ mL/(0.21 atm·day·package).
(2) Appearance after Molding
Presence or absence of whitening of vial after molding was visually observed.
(3) Drop Test
After a vial was stored under the conditions of 40° C. and 90% RH for one month, the vial was filled up with pure water (50 mL) and then sealed by a rubber tap and an aluminum cap. The sealed container thus obtained was allowed to drop from a height of 2 m. The appearance of the container at this time was checked.

(4) Elution Test
After a vial was stored under the conditions of 40° C. and 90% RH for one month, the vial was filled up with pure water (50 mL) and then sealed by a rubber tap and an aluminum cap. The sealed container thus obtained was stored under the conditions of 40° C. and 60% RH for 4 months and then the total amount of carbon (hereinafter, TOC) in the pure water was measured.
(TOC Measurement)
Apparatus: TOC-$V_{CPH}$ manufactured by Shimadzu Corporation
Temperature of combustion furnace: 720° C.
Gas and flow rate: highly purified air, 150 mL/min in TOC meter
Injection amount: 150 μL
Detection limit: 1 μg/mL Examples 4-2 to 4-4

Oxygen-absorbing resin compositions and vials were manufactured in the same manner as in Example 4-1 except that each of the corresponding polyamide compounds shown in Table 7 was used in place of the polyamide compound (1-1). The performance of the obtained vials was individually evaluated in the same manner as in Example 4-1. The evaluation results are shown in Table 7.

Comparative Example 4-1

A single-layer vial having the same shape as in Example 4-1 was manufactured in the same manner as in Example 4-1 except that a cycloolefin copolymer (TOPAS 6013 manufactured by Ticona GmbH) (100 parts by mass) was used in place of the oxygen-absorbing resin composition (1-1). The performance of the obtained vial was evaluated in the same manner as in Example 4-1. The evaluation results are shown in Table 7.

Comparative Example 4-2

With nylon MXD6 (S7007, manufactured by Mitsubishi Gas Chemical Company, Inc.) (100 parts by mass), cobalt stearate (II) (0.04 parts by mass in terms of cobalt) was dry-blended. The obtained mixture was supplied to a double-screw extruder having two screws of 37 mm in diameter at a rate of 15 kg/h. Melt-kneading was performed at a cylinder temperature of 280° C. and a strand was extruded from an extruder head. After cooling, the strand was pelletized to obtain an oxygen-absorbing resin composition (M-1). A vial was manufactured in the same manner as in Example 4-1 except that the oxygen-absorbing resin composition (M-1) was used in place of the oxygen-absorbing resin composition (4-1). The performance of the obtained vial was evaluated in the same manner as in Example 4-1. The evaluation results are shown in Table 7.

TABLE 7

| | Resin used in Layer A | Layer constitution | Oxygen transmission rate[1] (30th day) mL/(0.21 atm · day · package) | Appearance after molding | Drop test | Elution test TOC amount[2] (μg/mL) |
|---|---|---|---|---|---|---|
| Example 4-1 | Polyamide compound (1-1) | Three layers | Detection limit or less | Transparent | No breakage was observed in all containers | Detection limit or less |

TABLE 7-continued

| | Resin used in Layer A | Layer constitution | Oxygen transmission rate[1] (30th day) mL/(0.21 atm · day · package) | Appearance after molding | Drop test | Elution test TOC amount[2] (μg/mL) |
|---|---|---|---|---|---|---|
| Example 4-2 | Polyamide compound (1-2) | Three layers | Detection limit or less | Transparent | No breakage was observed in all containers | Detection limit or less |
| Example 4-3 | Polyamide compound (1-3) | Three layers | Detection limit or less | Transparent | No breakage was observed in all containers | Detection limit or less |
| Example 4-4 | Polyamide compound (1-4) | Three layers | Detection limit or less | Transparent | No breakage was observed in all containers | Detection limit or less |
| Comparative Example 4-1 | — | Single layer | 0.0871 | Transparent | No breakage was observed in all containers | Detection limit or less |
| Comparative Example 4-2 | Nylon MXD6 | Three layers | Detection limit or less | Slightly whitened in whole | 14 out of 20 containers were broken | 15 |

[1]Detection lower limit is $5 \times 10^{-5}$ mL/(0.21 atm · day · package).
[2]Detection lower limit is 0.1 (μg/mL).

As is apparent from Table 7, it was confirmed that the vials of Examples 4-1 to 4-4 have satisfactory oxygen barrier property and maintain satisfactory strength even after long-term storage, and that the amount of elution from the container to the content is small. Furthermore, it was confirmed that the vials of Examples 4-1 to 4-4 each have sufficient visibility of the content in a container.

Example 5-1

With a polyamide compound (1-1) (100 parts by mass), cobalt stearate (II) (0.1 parts by mass in terms of cobalt) was dry-blended. The obtained mixture was supplied to a double-screw extruder having two screws of 37 mm in diameter, at a rate of 15 kg/h. Melt-kneading was performed at a cylinder temperature of 290° C. and a strand was extruded from an extruder head. After cooling, the strand was pelletized to obtain an oxygen-absorbing resin composition (5-1). Subsequently, as shown below, a multilayer injection molded container, i.e., vial, was manufactured by using the oxygen-absorbing resin composition (5-1). The performance of the obtained vial was evaluated in the same manner as in Example 4-1. Furthermore, the performance, i.e., water vapor transmission rate of the vial was evaluated in the following manner. The evaluation results are shown in Table 8.

[Manufacturing of Vial]

Under the following conditions, the polyolefin for constituting a resin layer (layer B) was injected from an injection cylinder and then the oxygen-absorbing resin composition (5-1) for constituting an oxygen-absorbing layer (layer A) was injected from another injection cylinder simultaneously with the thermoplastic resin for constituting layer B. Subsequently, a polyolefin for constituting layer B was injected in a necessary amount to fill the cavity of an injection mold to obtain an injection molded article of a three-layer constitution (B/A/B). Thereafter, the obtained injection-molded article was cooled to a predetermined temperature and transferred to a mold for blow molding. Blow molding was performed to manufacture a vial (bottle portion). The total mass of the vial herein was specified as 24 g and the mass of layer A was specified as 30 mass % of the total mass of the vial. A cycloolefin copolymer (trade name: TOPAS6013, manufactured by Ticona GmbH) was used as the polyolefin for constituting layer B.

(Shape of Vial)

The whole length of a vial was specified as 89 mm, the outer diameter as 40 mmφ and the film thickness as 1.8 mm. Note that a vial was manufactured by use of an integrated injection blow-molding machine (Type: IBS 85, proving 4 vials, manufactured by UNILOY).

(Molding Conditions for Vial)

Temperature of injection cylinder for layer A: 280° C.
Temperature of injection cylinder for layer B: 280° C.
Temperature of resin flow channel in injection mold: 280° C.
Blowing temperature: 150° C.
Temperature of cooling water for blow mold: 15° C.

[Performance Evaluation of Vial]

(5) Water Vapor Transmission Rate (WVTR) of Vial

The water vapor transmission rate of 10th day from initiation of measurement was measured at 40° C. and under an atmosphere having a relative humidity of 100%, which was measured outside a molded article. Measurement was performed by use of a water vapor transmission rate measurement apparatus (trade name: PERMATRAN-W 3/33G, manufactured by MOCON). The lower the measurement value, the more satisfactory the water vapor barrier property. Note that the detection lower limit of water vapor transmission rate measured is $5 \times 10^{-4}$ g/(day·package).

Examples 5-2 to 5-4

Oxygen-absorbing resin compositions and vials were manufactured in the same manner as in Example 5-1 except that each of the corresponding polyamide compounds shown in Table 8 was used in place of the polyamide compound (1-1). The performance of the obtained vials was individually evaluated in the same manner as in Example 5-1. The evaluation results are shown in Table 8.

Comparative Example 5-1

A single-layer vial having the same shape as in Example 5-1 was manufactured in the same manner as in Example 5-1 except that a cycloolefin copolymer (TOPAS 6013 manufactured by Ticona GmbH) (100 parts by mass) was used in place of the oxygen-absorbing resin composition (1-1). The performance of the obtained vial was evaluated in the same manner as in Example 5-1. The evaluation results are shown in Table 8.

Comparative Example 5-2

A vial was manufactured in the same manner as in Example 5-1 except that a polycarbonate (Lexan 144R, manufactured by Sabic) was used in place of the cycloolefin copolymer as the thermoplastic resin for constituting layer B. The performance of the obtained vial was evaluated in the same manner as in Example 5-1. The evaluation results are shown in Table 8.

Comparative Example 5-3

With nylon MXD6 (S7007, manufactured by Mitsubishi Gas Chemical Company, Inc.) (100 parts by mass), cobalt stearate (II) (0.04 parts by mass in terms of cobalt) was dry-blended. The obtained mixture was supplied to a double-screw extruder having two screws of 37 mm in diameter at a rate of 15 kg/h. Melt-kneading was performed at a cylinder temperature of 280° C. and a strand was extruded from an extruder head. After cooling, the strand was pelletized to obtain an oxygen-absorbing resin composition (M-2). A vial was manufactured in the same manner as in Example 5-1 except that the oxygen-absorbing resin composition (M-2) was used in place of the oxygen-absorbing resin composition (5-1). The performance of the obtained vial was evaluated in the same manner as in Example 5-1. The evaluation results are shown in Table 8.

As is apparent from Table 8, it was confirmed that the vials of Examples 5-1 to 5-4 have satisfactory oxygen barrier property and water vapor barrier property and maintain satisfactory strength even after long-term storage, and that the amount of elution from the container to the content is small. Furthermore, it was confirmed that the vials of Examples 5-1 to 5-4 each have sufficient visibility of the content in a container.

Example 6-1

With a polyamide compound (1-1) (100 parts by mass), cobalt stearate (II) (0.1 parts by mass in terms of cobalt) was dry-blended. The obtained mixture was supplied to a double-screw extruder having two screws of 37 mm in diameter, at a rate of 30 kg/h. Melt-kneading was performed at a cylinder temperature of 290° C. and a strand was extruded from an extruder head. After cooling, the strand was pelletized to obtain an oxygen-absorbing resin composition (6-1). Subsequently, as shown below, a multilayer injection molded container, i.e., vial, was manufactured by using the oxygen-absorbing resin composition (6-1). The performance of the obtained vial was evaluated in the same manner as in Example 5-1. In this case, in place of evaluation of appearance after molding, the performance of the vial, i.e., visibility of the content, was evaluated as shown below. The evaluation results are shown in Table 9.

(6) Content Visibility of Vial

The content of a vial was visually observed. The vial, which was transparent and the content thereof was visible without any problem, was determined as being acceptable. The vial, which was hazy but the content thereof was visible without any problem was also accepted.

TABLE 8

| | Resin used in Layer A | Resin used in Layer B | Layer constitution | Oxygen transmission rate (30th day)[1] | Appearance after molding | Drop test | Elution test TOC amount[2] (µg/mL) | Water vapor transmission rate (10th day) g/(day · package) |
|---|---|---|---|---|---|---|---|---|
| Example 5-1 | Polyamide compound (1-1) | COC | Three layers | Detection limit or less | Transparent | No breakage was observed in all containers | Detection limit or less | 0.0007 |
| Example 5-2 | Polyamide compound (1-2) | COC | Three layers | Detection limit or less | Transparent | No breakage was observed in all containers | Detection limit or less | 0.0008 |
| Example 5-3 | Polyamide compound (1-3) | COC | Three layers | Detection limit or less | Transparent | No breakage was observed in all containers | Detection limit or less | 0.0007 |
| Example 5-4 | Polyamide compound (1-4) | COC | Three layers | Detection limit or less | Transparent | No breakage was observed in all containers | Detection limit or less | 0.0008 |
| Comparative Example 5-1 | | COC | Single layer | Single layer | 0.0871 | Transparent | No breakage was observed in all containers | Detection limit or less | 0.0007 |
| Comparative Example 5-2 | Polyamide compound (1-1) | PC | Three layers | Detection limit or less | Transparent | No breakage was observed in all containers | Detection limit or less | 0.0198 |
| Comparative Example 5-3 | Nylon MXD6 | COC | Three layers | Detection limit or less | Slightly whitened in whole | 14 out of 20 containers were broken | 15 | 0.0009 |

[1] Unit is mL/(0.21 atm · day · package) and the detection lower limit is $5 \times 10^{-5}$ mL/(0.21 atm · day · package).
[2] Detection lower limit is 0.1 (µg/mL).

[Manufacturing of Vial]

Under the following conditions, a polyester for constituting a resin layer (layer B) was injected from an injection cylinder and then the oxygen-absorbing resin composition (6-1) for constituting an oxygen-absorbing layer (layer A) was injected from another injection cylinder simultaneously with a polyester for constituting layer B. Subsequently, a polyester for constituting layer B was injected in a necessary amount to fill the cavity of an injection mold to obtain an injection molded article of a three-layer constitution (B/A/B). Thereafter, the obtained injection-molded article was cooled to a predetermined temperature and transferred to a mold for blow molding. Blow molding was performed to manufacture a vial (bottle portion). The total mass of the vial herein was specified as 24 g and the mass of layer A was specified as 30 mass % of the total mass of the vial. Polyethylene terephthalate (trade name: RT-553C, manufactured by Japan Unipet) was used as a polyester for constituting layer B.

(Shape of Vial)

The whole length of a vial was specified as 89 mm, the outer diameter as 40 mmϕ and the film thickness as 1.8 mm. Note that a vial was manufactured by use of an integrated injection blow molding machine (Type: IBS 85, proving 4 vials, manufactured by UNILOY).

(Molding Conditions for Vial)

Temperature of injection cylinder for layer A: 280° C.
Temperature of injection cylinder for layer B: 280° C.
Temperature of resin flow channel in injection mold: 280° C.
Blowing temperature: 150° C.
Temperature of cooling water for blow mold: 15° C.

Examples 6-2 to 6-4

Oxygen-absorbing resin compositions and vials were manufactured in the same manner as in Example 6-1 except that each of the corresponding polyamide compounds shown in Table 9 was used in place of the polyamide compound (1-1). The performance of the obtained vials was individually evaluated in the same manner as in Example 6-1. The evaluation results are shown in Table 9.

Comparative Example 6-1

A single-layer vial having the same shape as in Example 6-1 was manufactured in the same manner as in Example 6-1 except that a cycloolefin copolymer (TOPAS 6013 manufactured by Ticona GmbH) (100 parts by mass) was used in place of the oxygen-absorbing resin composition (6-1). The performance of the obtained vial was evaluated in the same manner as in Example 6-1. The evaluation results are shown in Table 9.

Comparative Example 6-2

A vial was manufactured in the same manner as in Example 6-1 except that a polycarbonate (LEXAN 144R, manufactured by Sabic) was used in place of polyethylene terephthalate serving as the thermoplastic resin constituting layer B. The performance of the obtained vial was evaluated in the same manner as in Example 6-1. The evaluation results are shown in Table 9.

Comparative Example 6-3

With nylon MXD6 (S7007, manufactured by Mitsubishi Gas Chemical Company, Inc.) (100 parts by mass), cobalt stearate (II) (0.04 parts by mass in terms of cobalt) was dry-blended. The obtained mixture was supplied to a double-screw extruder having two screws of 37 mm in diameter at a rate of 30 kg/h. Melt-kneading was performed at a cylinder temperature of 280° C. and a strand was extruded from an extruder head. After cooling, the strand was pelletized to obtain an oxygen-absorbing resin composition (M-3). A vial was manufactured in the same manner as in Example 6-1 except that the oxygen-absorbing resin composition (M-3) was used in place of the oxygen-absorbing resin composition (6-1). The performance of the obtained vial was evaluated in the same manner as in Example 6-1. The evaluation results are shown in Table 9.

TABLE 9

|  | Resin used in Layer A | Resin used in Layer B | Layer constitution | Oxygen transmission rate (30th day)[1] | Visibility of content | Drop test | Elution test TOC amount[2] (μg/mL) | Water vapor transmission rate (10th day) g/(day · package) |
|---|---|---|---|---|---|---|---|---|
| Example 6-1 | Polyamide compound (1-1) | PET | Three layers | Detection limit or less | Transparent (acceptable) | No breakage was observed in all containers | Detection limit or less | 0.0074 |
| Example 6-2 | Polyamide compound (1-2) | PET | Three layers | Detection limit or less | Transparent (acceptable) | No breakage was observed in all containers | Detection limit or less | 0.0069 |
| Example 6-3 | Polyamide compound (1-3) | PET | Three layers | Detection limit or less | Transparent (acceptable) | No breakage was observed in all containers | Detection limit or less | 0.0072 |

TABLE 9-continued

| | Resin used in Layer A | Resin used in Layer B | Layer constitution | Oxygen transmission rate (30th day)[1] | Visibility of content | Drop test | Elution test TOC amount[2] (μg/mL) | Water vapor transmission rate (10th day) g/(day · package) |
|---|---|---|---|---|---|---|---|---|
| Example 6-4 | Polyamide compound (1-4) | PET | Three layers | Detection limit or less | Transparent (acceptable) | No breakage was observed in all containers | Detection limit or less | 0.0078 |
| Comparative Example 6-1 | COC | Single layer | Single layer | 0.0871 | Transparent (acceptable) | No breakage was observed in all containers | Detection limit or less | 0.0007 |
| Comparative Example 6-2 | Polyamide compound (1-1) | PC | Three layers | Detection limit or less | Transparent (acceptable) | No breakage was observed in all containers | Detection limit or less | 0.0198 |
| Comparative Example 6-3 | Nylon MXD6 | PET | Three layers | Detection limit or less | Hazy (acceptable) | 11 out of 20 containers were broken | 15 | 0.0009 |

[1]Unit is mL/(0.21 atm · day · package) and the detection lower limit is $5 \times 10^{-5}$ mL/(0.21 atm · day · package).
[2]Detection lower limit is 0.1 (μg/mL).

As is apparent from Table 9, it was confirmed that vials of Examples 6-1 to 6-4 each have satisfactory oxygen barrier property and water vapor barrier property and maintain satisfactory strength even after long-term storage; and that the amount of elution from the container to the content was small. Furthermore, it was confirmed that vials of Examples 6-1 to 6-4 have visibility of the content and are excellent in transparency.

Example 7-1

With a polyamide compound (1-1) (100 parts by mass), cobalt stearate (II) (0.1 parts by mass in terms of cobalt) was dry-blended. The obtained mixture was supplied to a double-screw extruder having two screws of 37 mm in diameter, at a rate of 30 kg/h. Melt-kneading was performed at a cylinder temperature of 290° C. and a strand was extruded from an extruder head. After cooling, the strand was pelletized to obtain an oxygen-absorbing resin composition (7-1). Subsequently, as shown below, a multilayer injection molded container, i.e., syringe, was manufactured by using the oxygen-absorbing resin composition (7-1). Thereafter, performance of the obtained syringe was evaluated as shown below. The evaluation results are shown in Table 10.

[Manufacturing of Syringe]

Under the following conditions, the thermoplastic resin for constituting a resin layer (layer B) was injected from an injection cylinder and then the oxygen-absorbing resin composition (7-1) for constituting an oxygen-absorbing layer (layer A) was injected from another injection cylinder simultaneously with the thermoplastic resin for constituting layer B. Subsequently, the thermoplastic resin for constituting layer B was injected in a necessary amount to fill the cavity of an injection mold to manufacture a syringe constituted of three layers (B/A/B). The total mass of the syringe herein was specified as 1.95 g and the mass of layer A was specified as 30 mass % of the total mass of the syringe. A cycloolefin copolymer (trade name: TOPAS 6013, manufactured by Ticona GmbH) was used as the thermoplastic resin for constituting layer B.

(Shape of Syringe)

The volume (1 cc) of the content was used as a standard in accordance with ISO11040-6. Note that a syringe was manufactured by use of an injection molding machine (type: ASB-12N/10, manufactured by Nissei ASB Machine Co., Ltd).

(Conditions for Molding Syringe)

Temperature of injection cylinder for layer A: 280° C.
Temperature of injection cylinder for layer B: 280° C.
Temperature of resin flow channel in injection mold: 280° C.
Mold temperature: 18° C.

[Performance Evaluation of Syringe]

Measurement of oxygen transmission rate, evaluation of appearance after molding, impact resistance test and elution test of the obtained syringes were performed in accordance with the following methods and evaluation was made based on the following criteria.

(1) Oxygen Transmission Rate (OTR) of Syringe

At the 30th day from initiation of measurement, the oxygen transmission rate was measured at 23° C. and under an atmosphere having a relative humidity of 50%, which was measured outside the molded article, and a relative humidity of 100%, which was measured within the molded article. Measurement was performed by use of an oxygen transmission rate measurement apparatus (trade name: OX-TRAN 2-21ML, manufactured by MOCON). The lower the measurement value, the more satisfactory the oxygen barrier property. Note that detection lower limit of oxygen transmission rate measured is $5 \times 10^{-5}$ mL/(0.21 atm·day·package).

(2) Visibility of Content in Syringe

The content in a syringe was visually observed. The visibility of a content in the syringe was evaluated. If the content was visible without any problem, the syringe was determined to come up to the standard.

(3) Impact Resistance Test

After a syringe was stored under the conditions of 40° C. and 90% RH for one month, a metal ball (50 g) was dropped on the body of the syringe from a height of 2 m. At this time, the presence or absence of breakage was checked with respect to 20 samples.

(4) Elution Test

After a syringe was stored under the conditions of 40° C. and 90% RH for one month, the syringe was filled with pure water (1 cc) and sealed with a plunger equipped with a top cap and a gasket. The syringe thus obtained was stored under the conditions of 40° C. and 60% RH for 4 months and thereafter, the total amount of carbon (hereinafter, TOC) in the pure water was measured.

(TOC Measurement)

Apparatus: TOC-V$_{CPH}$ manufactured by Shimadzu Corporation

Temperature of combustion furnace: 720° C.

Gas/flow rate: highly purified air, 150 mL/min measured by TOC meter

Injection amount: 150 μL

Detection limit: 1 μg/mL evaluated in the same manner as in Example 7-1. The evaluation results are shown in Table 10.

Comparative Example 7-2

With nylon MXD6 (S7007, manufactured by Mitsubishi Gas Chemical Company, Inc.) (100 parts by mass), cobalt stearate (II) (0.04 parts by mass in terms of cobalt) was dry-blended. The obtained mixture was supplied to a double-screw extruder having two screws of 37 mm in diameter at a rate of 15 kg/h. Melt-kneading was performed at a cylinder temperature of 280° C. and a strand was extruded from an extruder head. After cooling, the strand was pelletized to obtain an oxygen-absorbing resin composition (M-4). A syringe was manufactured in the same manner as in Example 7-1 except that the oxygen-absorbing resin composition (M-4) was used in place of the oxygen-absorbing resin composition (7-1). The performance of the obtained syringe was evaluated in the same manner as in Example 7-1. The evaluation results are shown in Table 10.

TABLE 10

| | Resin used in Layer A | Layer constitution | Oxygen transmission rate[1] (30th day) | Visibility of content | Impact resistance test | Elution test TOC amount[2] (μg/mL) |
|---|---|---|---|---|---|---|
| Example 7-1 | Polyamide compound (1-1) | Three layers | Detection limit or less | Transparent (acceptable) | No breakage was observed in all containers | Detection limit or less |
| Example 7-2 | Polyamide compound (1-2) | Three layers | Detection limit or less | Transparent (acceptable) | No breakage was observed in all containers | Detection limit or less |
| Example 7-3 | Polyamide compound (1-3) | Three layers | Detection limit or less | Transparent (acceptable) | No breakage was observed in all containers | Detection limit or less |
| Example 7-4 | Polyamide compound (1-4) | Three layers | Detection limit or less | Transparent (acceptable) | No breakage was observed in all containers | Detection limit or less |
| Comparative Example 7-1 | COC Single layer | Single layer | 0.024 | Transparent (acceptable) | No breakage was observed in all containers | Detection limit or less |
| Comparative Example 7-2 | Nylon MXD6 | Three layers | Detection limit or less | Hazy (acceptable) | 7 out of 20 containers were broken | 38 |

[1]Unit is mL/(0.21 atm · day · package) and the detection lower limit is 5 × 10$^{-5}$ mL/(0.21 atm · day · package).
[2]Detection lower limit is 0.1 (μg/mL).

Examples 7-2 to 7-4

Oxygen-absorbing resin compositions and syringes were manufactured in the same manner as in Example 7-1 except that each of the corresponding polyamide compounds shown in Table 10 was used in place of the polyamide compound (1-1). The performance of the obtained syringes was individually evaluated in the same manner as in Example 7-1. The evaluation results are shown in Table 10.

Comparative Example 7-1

A single-layer syringe having the same shape as in Example 7-1 was manufactured in the same manner as in Example 7-1 except that a cycloolefin copolymer (TOPAS 6013 manufactured by Ticona GmbH) (100 parts by mass) was used in place of the oxygen-absorbing resin composition (7-1). The performance of the obtained syringe was As is apparent from Table 10, it was confirmed that syringes of Examples 7-1 to 7-4 each have satisfactory oxygen barrier property and maintain satisfactory strength even after long-term storage; and that the amount of elution from the container to the content was small. Furthermore, it was confirmed that syringes of Examples 7-1 to 7-4 have visibility of the content and are excellent in transparency.

Example 8-1

With a polyamide compound (1-1) (100 parts by mass), cobalt stearate (II) (0.1 parts by mass in terms of cobalt) was dry-blended. The obtained mixture was supplied to a double-screw extruder having two screws of 37 mm in diameter, at a rate of 15 kg/h. Melt-kneading was performed at a cylinder temperature of 220° C. and a strand was extruded from an extruder head. After cooling, the strand was pelletized to obtain an oxygen-absorbing resin composition (8-1). Subsequently, as shown below, a multilayer injection molded container, i.e., vial, was manufactured by using the oxygen-absorbing resin composition (8-1). Thereafter, the performance of the obtained vial was evaluated in the same manner as in Example 4-1. Furthermore, a storage test of biopharmaceutical of vials was performed in the following manner. The evaluation results are shown in Table 11.
[Manufacturing of Vial]

Under the following conditions, the thermoplastic resin for constituting a resin layer (layer B) was injected from an injection cylinder and then the oxygen-absorbing resin composition (8-1) for constituting an oxygen-absorbing layer (layer A) was injected from another injection cylinder simultaneously with the thermoplastic resin for constituting layer B. Subsequently, a thermoplastic resin for constituting layer B was injected in a necessary amount to fill the cavity of an injection mold to obtain an injection-molded article of a three layer constitution (B/A/B). Thereafter, the obtained injection-molded article was cooled to a predetermined temperature and transferred to a mold for blow molding. Blow molding was performed to manufacture a vial (bottle portion). The total mass of the vial herein was specified as 24 g and the mass of layer A was specified as 30 mass % of the total mass of the vial. A cycloolefin copolymer (trade name: TOPAS6013, manufactured by Ticona GmbH) was used as the thermoplastic resin for constituting layer B.
(Shape of Vial)

The whole length of a vial was specified as 89 mm, the outer diameter as 40 mmϕ and the film thickness as 1.8 mm. Note that a vial was manufactured by use of an integrated injection blow molding machine (Type: IBS 85, proving 4 vials, manufactured by UNILOY).
(Molding Conditions for Vial)
Temperature of injection cylinder for layer A: 280° C.
Temperature of injection cylinder for layer B: 280° C.
Temperature of resin flow channel in injection mold: 280° C.
Blowing temperature: 150° C.
Temperature of cooling water for blow mold: 15° C.
[Performance Evaluation of Vial]
(7) Storage Test of Biopharmaceutical
(Binding-Rate Measurement Method)

Using an isothermal titration calorimetry, a cell was filled with an antigen solution (5 μm) (FGF1-Mouse, manufactured by BIOLOGICAL Industries Ltd.). While adding an antibody solution (10 μL) dropwise to the cell, the binding rate was measured at 25° C.
(Storage Test)

A vial was filled with 1 cc of ANTI FGF1 monoclonal antibody (mAb1) (manufactured by Wako Pure Chemical Industries Ltd.), of which the concentration was adjusted to be 50 μm, and stored under the conditions of 8° C. and 50% RH for 180 days. As a solvent, a phosphate buffer (PBS pH 7.4) manufactured by Invitrogen was used. The binding rates in the antibody solution before and after the storage test (for 180 days) were measured by the method mentioned above and an antibody activity retention rate was obtained from the binding rates before and after the storage in accordance with the following expression:

Antibody activity retention rate (%)=(Binding rate in the antibody solution after storage of 180 days/ Binding rate in the antibody solution before storage)×100

Examples 8-2 to 8-4

Oxygen-absorbing resin compositions and vials were manufactured in the same manner as in Example 8-1 except that each of the corresponding polyamide compounds shown in Table 11 was used in place of the polyamide compound (1-1). The performance of the obtained vials was individually evaluated in the same manner as in Example 8-1. The evaluation results are shown in Table 11.

Comparative Example 8-1

A single-layer vial having the same shape as in Example 8-1 was manufactured in the same manner as in Example 8-1 except that a cycloolefin copolymer (TOPAS 6013 manufactured by Ticona GmbH) (100 parts by mass) was used in place of the oxygen-absorbing resin composition (8-1). The performance of the obtained vial was evaluated in the same manner as in Example 8-1. The evaluation results are shown in Table 11.

Comparative Example 8-2

With nylon MXD6 (S7007, manufactured by Mitsubishi Gas Chemical Company, Inc.) (100 parts by mass), cobalt stearate (II) (0.04 parts by mass in terms of cobalt) was dry-blended. The obtained mixture was supplied to a double-screw extruder having two screws of 37 mm in diameter at a rate of 15 kg/h. Melt-kneading was performed at a cylinder temperature of 280° C. and a strand was extruded from an extruder head. After cooling, the strand was pelletized to obtain an oxygen-absorbing resin composition (M-5). A vial was manufactured in the same manner as in Example 8-1 except that the oxygen-absorbing resin composition (M-5) was used in place of the oxygen-absorbing resin composition (8-1). The performance of the obtained vial was evaluated in the same manner as in Example 8-1. The evaluation results are shown in Table 11.

TABLE 11

| | Resin used in Layer A | Resin used in Layer B | Layer constitution | Oxygen transmission rate[1] (30th day) | Appearance after molding | Drop test | Elution test TOC amount[2] (μg/mL) | Antibody activity retention rate (%) |
|---|---|---|---|---|---|---|---|---|
| Example 8-1 | Polyamide compound (1-1) | COC | Three layers | Detection limit or less | Transparent | No breakage was observed in all containers | Detection limit or less | 77 |

TABLE 11-continued

|  | Resin used in Layer A | Resin used in Layer B | Layer constitution | Oxygen transmission rate[1] (30th day) | Appearance after molding | Drop test | Elution test TOC amount[2] (μg/mL) | Antibody activity retention rate (%) |
|---|---|---|---|---|---|---|---|---|
| Example 8-2 | Polyamide compound (1-2) | COC | Three layers | Detection limit or less | Transparent | No breakage was observed in all containers | Detection limit or less | 70 |
| Example 8-3 | Polyamide compound (1-3) | COC | Three layers | Detection limit or less | Transparent | No breakage was observed in all containers | Detection limit or less | 69 |
| Example 8-4 | Polyamide compound (1-4) | COC | Three layers | Detection limit or less | Transparent | No breakage was observed in all containers | Detection limit or less | 78 |
| Comparative Example 8-1 |  | COC | Single layer | Single layer | 0.0871 | Transparent | No breakage was observed in all containers | Detection limit or less | 35 |
| Comparative Example 8-2 | Nylon MXD6 | COC | Three layers | Detection limit or less | Slightly whitened in whole | 14 out of 20 containers were broken | 15 | 79 |

[1] Unit is mL/(0.21 atm · day · package) and the detection lower limit is $5 \times 10^{-5}$ mL/(0.21 atm · day · package).
[2] Detection lower limit is 0.1 (μg/mL).

As is apparent from Table 11, it was confirmed that when a biopharmaceutical is stored in the vials of Examples 8-1 to 8-4, satisfactory strength was maintained even after long-term storage and that the amount of elution from the container to the content is small and thus reduction of drug efficacy after storage was suppressed.

As described in the foregoing, the present invention is not limited to the above embodiments and Examples and can be appropriately modified within the gist of the invention.

Note that the present application claims a priority right based on the following 10 Japanese Patent Applications, the contents of which are incorporated herein by reference.

Japanese Patent Application No. 2011-275861 filed with the Japanese Patent Office on Dec. 16, 2011.

Japanese Patent Application No. 2012-178270 filed with the Japanese Patent Office on Aug. 10, 2012.

Japanese Patent Application No. 2012-264590 filed with the Japanese Patent Office on Dec. 3, 2012.

Japanese Patent Application No. 2012-265119 filed with the Japanese Patent Office on Dec. 4, 2012.

Japanese Patent Application No. 2012-265120 filed with the Japanese Patent Office on Dec. 4, 2012.

Japanese Patent Application No. 2012-267218 filed with the Japanese Patent Office on Dec. 6, 2012.

Japanese Patent Application No. 2012-268338 filed with the Japanese Patent Office on Dec. 7, 2012.

Japanese Patent Application No. 2012-269379 filed with the Japanese Patent Office on Dec. 10, 2012.

Japanese Patent Application No. 2012-269380 filed with the Japanese Patent Office on Dec. 10, 2012.

Japanese Patent Application No. 2012-270356 filed with the Japanese Patent Office on Dec. 11, 2012.

INDUSTRIAL APPLICABILITY

The oxygen-absorbing resin composition etc. of the present invention, since they have excellent oxygen-absorbing performance in a wide range of humidity conditions from low humidity to high humidity, can be widely and effectively used in general technical fields requiring oxygen absorption. Furthermore, since the composition etc. can absorb oxygen regardless of the presence or absence of the moisture content of an article to be packed and produce no odor after absorption of oxygen, they can be particularly effectively used in e.g., foods, cooking foods, beverages, medicinal products and health foods. Moreover, since an oxygen-absorbing resin composition etc. not responsive to a metal detector can also be provided, they can be widely and effectively applied to uses requiring external inspection of metals, metal pieces, etc. by a metal detector, for example, packaging materials and containers.

The invention claimed is:

1. An oxygen-absorbing resin composition comprising a polyamide compound and a transition metal catalyst, wherein the polyamide compound has at least one constituent unit having a tetralin ring selected from the group consisting of constituent units represented by the following general formulas (1) and (2):

$$\left[ \begin{array}{c} \underset{H}{N} - \underset{O}{\overset{\|}{C}} - \underset{(R)_m}{\bigcirc\!\!\!\bigcirc} - \underset{(R)_n}{\overset{\|}{C}} - \underset{H}{N} - X \end{array} \right] \quad (1)$$

$$\left[ \begin{array}{c} \underset{O}{\overset{\|}{C}} - \underset{H}{N} - \underset{(R)_m}{\bigcirc\!\!\!\bigcirc} - \underset{(R)_n}{N} - \underset{H}{\overset{\|}{C}} - X \end{array} \right] \quad (2)$$

where R each independently represents a monovalent substituent, the monovalent substituent being at least one selected from the group consisting of a halogen atom, an alkyl group, an alkenyl group, an alkynyl group, an aryl group, a heterocyclic group, a cyano group, a hydroxy group, a carboxyl group, an ester group, an amido group, a nitro group, an alkoxy group, an aryloxy group, an acyl group, an amino group, a mercapto group, an alkylthio group, an arylthio group, a heterocyclic thio group and an imido group, these of which may further have a substituent; where m each independently represents an integer of 0 to 3; where n each independently represents an integer of 0 to 6, and at least one hydrogen atom is bound to a benzyl position of the tetralin ring; where X each independently represents a divalent group containing at least one group selected from the group consisting of an aromatic hydrocarbon group, a saturated or unsaturated alicyclic hydrocarbon group, a linear or branched, saturated or unsaturated aliphatic hydrocarbon group, and a heterocyclic group, wherein the transition metal catalyst comprises at least one transition metal selected from the group consisting of manganese, iron, cobalt, nickel and copper.

2. The oxygen-absorbing resin composition according to claim 1, wherein the transition metal catalyst is contained in an amount of 0.001 to 10 parts by mass in terms of a transition metal based on 100 parts by mass of the polyamide compound.

3. The oxygen-absorbing resin composition according to claim 1, wherein the constituent unit represented by the general formula (1) is at least one selected from the group consisting of the constituent units represented by the following formulas (3) to (6):

4. An oxygen-absorbing multilayer injection-molded article comprising an oxygen-absorbing layer formed of the oxygen-absorbing resin composition according to claim 1 and a resin layer comprising a thermoplastic resin.

5. An oxygen-absorbing multilayer container obtained by molding the oxygen-absorbing multilayer injection-molded article according to claim 4 into a cup or bottle form.

6. The oxygen-absorbing multilayer container according to claim 5, wherein the molding is stretch blow molding.

7. An oxygen-absorbing multilayer body comprising at least three layers comprising a sealant layer comprising a thermoplastic resin, an oxygen-absorbing layer formed of the oxygen-absorbing resin composition according to claim 1 and a gas barrier layer comprising a gas barrier substance, in this order.

8. An oxygen-absorbing multilayer container comprising the oxygen-absorbing multilayer body according to claim 7.

9. An oxygen-absorbing medical multilayer molded container comprising at least three layers comprising a first resin layer at least comprising a thermoplastic resin, an oxygen-absorbing layer formed of the oxygen-absorbing resin composition according to claim 1 and a second resin layer at least comprising a thermoplastic resin in this order.

10. The oxygen-absorbing medical multilayer molded container according to claim 9, wherein each of the thermoplastic resin of the first resin layer and the thermoplastic resin of the second resin layer is a polyolefin.

11. The oxygen-absorbing medical multilayer molded container according to claim 9, wherein each of the thermoplastic resin of the first resin layer and the thermoplastic resin of the second resin layer is a polyester.

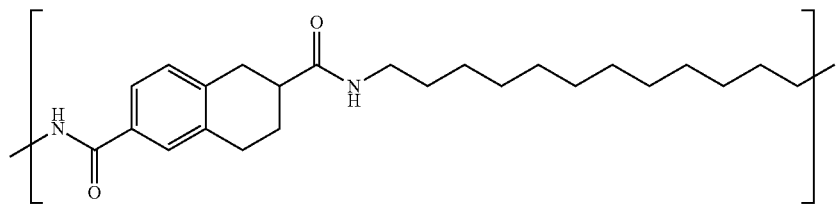

(3)

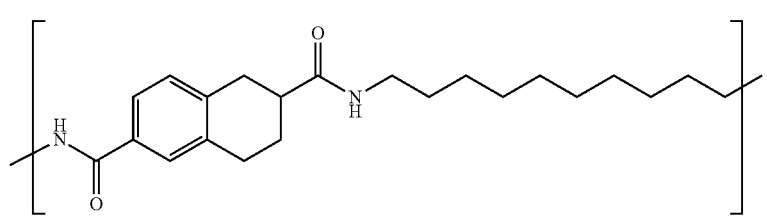

(4)

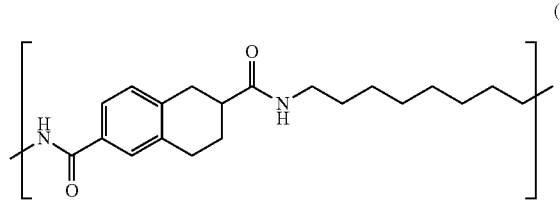

(5)

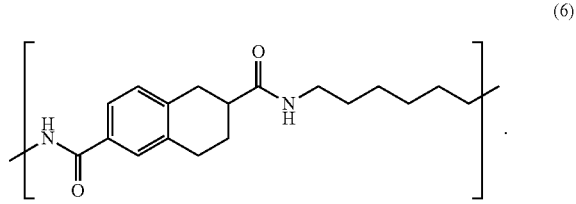

(6)

12. A method for storing a biopharmaceutical, comprising storing the biopharmaceutical in the oxygen-absorbing medical multilayer molded container according to claim 9.

13. An oxygen-absorbing prefilled syringe made capable of storing a medicinal agent in advance in a sealed condition, and releasing the sealed condition to eject the medical agent at a time of use, wherein the prefilled syringe is formed of a multilayer structure comprising at least three layers comprising a first resin layer comprising a thermoplastic resin, an oxygen-absorbing layer formed of the oxygen-absorbing resin composition according to claim 1 and a second resin layer comprising a thermoplastic resin in this order.

14. A method for storing a biopharmaceutical, comprising storing the biopharmaceutical in the oxygen-absorbing prefilled syringe according to claim 13.

* * * * *